(12) United States Patent
Lin et al.

(10) Patent No.: US 7,435,385 B2
(45) Date of Patent: Oct. 14, 2008

(54) LABEL-FREE HIGH-THROUGHPUT OPTICAL TECHNIQUE FOR DETECTING BIOMOLECULAR INTERACTIONS

(75) Inventors: Bo Lin, Lexington, MA (US); Peter Li, Andover, MA (US)

(73) Assignee: SRU Biosystems, Inc., Woburn, MA (US)

( * ) Notice: Subject to any disclaimer, the term of this patent is extended or adjusted under 35 U.S.C. 154(b) by 1006 days.

(21) Appl. No.: 10/415,037

(22) PCT Filed: Oct. 23, 2001

(86) PCT No.: PCT/US01/50723

§ 371 (c)(1),
(2), (4) Date: Jan. 20, 2004

(87) PCT Pub. No.: WO02/059602

PCT Pub. Date: Aug. 1, 2002

(65) Prior Publication Data

US 2004/0132172 A1  Jul. 8, 2004

Related U.S. Application Data

(60) Provisional application No. 60/303,028, filed on Jul. 3, 2001, provisional application No. 60/283,314, filed on Apr. 12, 2001, provisional application No. 60/244,312, filed on Oct. 30, 2000.

(51) Int. Cl.
*G01N 21/00* (2006.01)
*G01N 33/53* (2006.01)
*G01N 15/06* (2006.01)
*G01N 24/00* (2006.01)

(52) U.S. Cl. .................. 422/82.05; 422/68.1; 435/7.1; 436/173

(58) Field of Classification Search ............. None
See application file for complete search history.

(56) References Cited

U.S. PATENT DOCUMENTS

| 3,689,346 A | 9/1972 | Rowland ............ 156/245 |
| 3,810,688 A | 5/1974 | Ballman et al. ...... 350/96 |
| 3,856,404 A | 12/1974 | Hershler et al. |
| 3,856,604 A | 12/1974 | Hershler et al. ...... 156/361 |
| 4,009,933 A | 3/1977 | Firester |
| 4,050,895 A | 9/1977 | Hardy et al. ........ 436/527 |

(Continued)

FOREIGN PATENT DOCUMENTS

CA  2394966  2/2001

(Continued)

OTHER PUBLICATIONS

Brecht, et al., "Optical Probes and Transducers", vol. 10, Biosensors & Bioelectronics, pp. 923-936 (1995).

(Continued)

*Primary Examiner*—Jill Warden
*Assistant Examiner*—Neil Turk
(74) *Attorney, Agent, or Firm*—McDonnell Boehnen Hulbert & Berghoff LLP

(57) ABSTRACT

Methods and compositions are provided for detecting biomolecular interactions. The use of labels is not required and the methods can be performed in a high-throughput manner. The invention also provides optical devices useful as narrow band filters.

8 Claims, 52 Drawing Sheets

U.S. PATENT DOCUMENTS

| | | |
|---|---|---|
| 4,240,751 A | 12/1980 | Linnecke et al. ............. 356/409 |
| 4,289,371 A | 9/1981 | Kramer ...................... 350/3.71 |
| 4,344,438 A | 8/1982 | Schultz ........................ 128/633 |
| 4,420,502 A | 12/1983 | Conley ........................ 427/54.1 |
| 4,536,608 A | 8/1985 | Sheng et al. |
| 4,560,248 A | 12/1985 | Cramp et al. .................. 385/12 |
| 4,576,850 A | 3/1986 | Martens |
| 4,608,344 A | 8/1986 | Carter et al. .................. 436/34 |
| 4,650,329 A | 3/1987 | Barrett et al. ............... 356/481 |
| 4,652,290 A | 3/1987 | Cho et al. ........................ 65/31 |
| 4,668,558 A | 5/1987 | Barber |
| 4,701,008 A | 10/1987 | Richard et al. ............... 385/132 |
| 4,810,658 A | 3/1989 | Shanks et al. ................ 436/172 |
| 4,815,843 A | 3/1989 | Tiefenthaler et al. ......... 356/128 |
| 4,818,710 A | 4/1989 | Sutherland et al. ........... 436/527 |
| 4,857,273 A | 8/1989 | Stewart ........................ 422/68 |
| RE33,064 E | 9/1989 | Carter ........................... 436/34 |
| 4,876,208 A | 10/1989 | Gustafson et al. ............ 436/531 |
| 4,882,288 A | 11/1989 | North et al. .................. 436/525 |
| 4,888,260 A | 12/1989 | Cowen ............................. 430/1 |
| 4,931,384 A | 6/1990 | Layton et al. |
| 4,952,056 A | 8/1990 | Tiefenthaler ................. 356/73.1 |
| 4,958,895 A | 9/1990 | Wells et al. ................ 350/96.12 |
| 4,992,385 A | 2/1991 | Godfrey ....................... 436/525 |
| 4,999,234 A | 3/1991 | Cowan |
| 5,071,248 A | 12/1991 | Tiefenthaler et al. ......... 356/128 |
| 5,118,608 A | 6/1992 | Layton et al. |
| 5,155,785 A | 10/1992 | Holland et al. ................. 385/89 |
| 5,156,785 A | 10/1992 | Zdrahala ....................... 264/108 |
| 5,170,448 A | 12/1992 | Ackley et al. .................. 385/31 |
| 5,175,030 A | 12/1992 | Lu et al. |
| 5,210,404 A | 5/1993 | Cush et al. ................... 250/216 |
| 5,229,614 A | 7/1993 | Andersson et al. |
| 5,242,828 A | 9/1993 | Bergström et al. ........... 435/291 |
| 5,268,782 A | 12/1993 | Wenz et al. |
| 5,310,686 A | 5/1994 | Sawyers et al. |
| 5,337,183 A | 8/1994 | Rosenblatt ................... 359/248 |
| 5,395,587 A * | 3/1995 | Brigham-Burke et al. .. 422/68.1 |
| 5,413,884 A | 5/1995 | Koch et al. |
| 5,442,169 A | 8/1995 | Kunz |
| 5,455,178 A | 10/1995 | Fattinger ..................... 436/164 |
| 5,475,780 A | 12/1995 | Mizrahi ........................ 385/37 |
| 5,478,527 A | 12/1995 | Gustafson et al. .............. 422/82 |
| 5,478,756 A | 12/1995 | Gizeli et al. |
| 5,492,840 A | 2/1996 | Malmqvist et al. |
| 5,496,701 A | 3/1996 | Pollard-Knight |
| 5,559,338 A | 9/1996 | Elliott et al. |
| 5,598,267 A | 1/1997 | Sambles et al. |
| 5,598,300 A | 1/1997 | Magnusson et al. |
| 5,606,170 A | 2/1997 | Saaski et al. ................ 250/458.1 |
| 5,615,052 A | 3/1997 | Doggett |
| 5,629,214 A | 5/1997 | Crosby ........................ 436/518 |
| 5,631,171 A | 5/1997 | Sandstrom et al. ........... 436/518 |
| 5,690,894 A | 11/1997 | Pinkel et al. |
| 5,691,846 A | 11/1997 | Benson, Jr. et al. |
| 5,732,173 A | 3/1998 | Bylander et al. |
| 5,738,825 A | 4/1998 | Rudigier et al. ................ 422/82 |
| 5,768,461 A | 6/1998 | Svetkoff et al. .............. 385/116 |
| 5,771,328 A | 6/1998 | Wortman et al. |
| 5,792,411 A | 8/1998 | Morris et al. |
| 5,801,390 A | 9/1998 | Shiraishi ................... 250/559.3 |
| 5,804,453 A | 9/1998 | Chen |
| 5,814,516 A | 9/1998 | Vo-Dinh .................... 435/287.2 |
| 5,814,524 A | 9/1998 | Walt et al. .................... 436/514 |
| 5,821,343 A | 10/1998 | Keogh |
| 5,846,843 A | 12/1998 | Simon |
| 5,864,641 A | 1/1999 | Murphy et al. ................. 385/12 |
| 5,922,550 A | 7/1999 | Everhart et al. ............. 435/7.21 |
| 5,925,878 A | 7/1999 | Challener |
| 5,955,335 A | 9/1999 | Thust et al. |
| 5,955,378 A | 9/1999 | Challener |
| 5,955,729 A * | 9/1999 | Nelson et al. ................ 250/282 |
| 5,986,762 A | 11/1999 | Challener |
| 5,991,480 A | 11/1999 | Kunz et al. |
| 5,994,150 A | 11/1999 | Challener et al. |
| 5,998,298 A | 12/1999 | Fleming et al. .............. 438/692 |
| 6,035,089 A | 3/2000 | Grann et al. |
| 6,042,998 A | 3/2000 | Brueck et al. ................ 430/316 |
| 6,052,213 A | 4/2000 | Burt et al. .................... 359/237 |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch ................. 385/147 |
| 6,146,593 A | 11/2000 | Pinkel et al. |
| 6,174,677 B1 | 1/2001 | Vo-Dinh ......................... 435/6 |
| 6,185,019 B1 | 2/2001 | Hobbs et al. |
| 6,200,737 B1 | 3/2001 | Walt et al. .................... 430/320 |
| 6,215,928 B1 | 4/2001 | Friesem et al. ................. 385/37 |
| 6,218,194 B1 | 4/2001 | Lyndin et al. ................ 436/518 |
| 6,235,488 B1 | 5/2001 | Tom-Moy et al. |
| 6,303,179 B1 | 10/2001 | Koulik et al. |
| 6,316,153 B1 | 11/2001 | Goodman et al. ............... 430/8 |
| 6,320,991 B1 | 11/2001 | Challener et al. |
| RE37,473 E | 12/2001 | Challener |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. ...................... 385/12 |
| 6,404,554 B1 | 6/2002 | Lee et al. ..................... 359/576 |
| 6,449,097 B1 | 9/2002 | Zhu et al. ..................... 359/576 |
| 6,558,957 B1 | 5/2003 | Roinestad et al. ............ 436/164 |
| 6,570,657 B1 | 5/2003 | Hoppe et al. ................. 356/445 |
| 6,579,673 B2 | 6/2003 | McGrath et al. ................. 435/5 |
| 6,587,276 B2 | 7/2003 | Daniell ........................ 359/622 |
| 6,661,952 B2 | 12/2003 | Simpson et al. ................ 385/37 |
| 6,707,561 B1 | 3/2004 | Budach et al. ................ 356/521 |
| 6,748,138 B2 | 6/2004 | Wang et al. .................... 385/37 |
| 6,902,703 B2 | 6/2005 | Marquiss et al. |
| 6,951,715 B2 | 10/2005 | Cunningham |
| 7,023,544 B2 | 4/2006 | Cunningham |
| 7,070,987 B2 | 7/2006 | Cunningham |
| 7,094,595 B2 | 8/2006 | Cunningham |
| 7,118,710 B2 | 10/2006 | Cunningham |
| 7,153,702 B2 | 12/2006 | Lin |
| 7,267,993 B2 | 9/2007 | Pentrenko |
| 2002/0018610 A1 | 2/2002 | Challener et al. |
| 2002/0127565 A1 | 9/2002 | Cunningham et al. |
| 2002/0135752 A1 | 9/2002 | Sokolov et al. |
| 2002/0168295 A1 | 11/2002 | Cunningham et al. |
| 2002/0171045 A1 | 11/2002 | Perraut |
| 2003/0003599 A1 | 1/2003 | Wagner et al. |
| 2003/0017580 A1 | 1/2003 | Cunningham et al. |
| 2003/0017581 A1 | 1/2003 | Li et al. |
| 2003/0026891 A1 | 2/2003 | Qiu et al. |
| 2003/0027327 A1 | 2/2003 | Cunningham et al. |
| 2003/0027328 A1 | 2/2003 | Cunningham et al. |
| 2003/0032039 A1 | 2/2003 | Cunningham et al. |
| 2003/0059855 A1 | 3/2003 | Cunningham et al. |
| 2003/0068657 A1 | 4/2003 | Lin et al. |
| 2003/0077660 A1 | 4/2003 | Pien et al. |
| 2003/0092075 A1 | 5/2003 | Pepper |
| 2003/0113766 A1 | 6/2003 | Pepper et al. |
| 2003/0148542 A1 | 8/2003 | Pawlak et al. ................ 436/518 |
| 2003/0210396 A1 | 11/2003 | Hobbs et al. ................. 356/416 |
| 2004/0005540 A1 | 1/2004 | Pentreko |
| 2004/0011965 A1 | 1/2004 | Hodgkinson |
| 2004/0132172 A1 | 7/2004 | Cunningham et al. |
| 2004/0132214 A1 | 7/2004 | Lin et al. |
| 2004/0151626 A1 | 8/2004 | Cunningham et al. |
| 2005/0227374 A1 | 10/2005 | Cunningham |
| 2006/0030033 A1 | 2/2006 | Cunningham |
| 2006/0040376 A1 | 2/2006 | Cunningham et al. |
| 2006/0057707 A1 | 3/2006 | Lin et al. |
| 2006/0181705 A1 | 8/2006 | Cunningham et al. |

| | | | |
|---|---|---|---|
| 2006/0193550 | A1 | 8/2006 | Wawro et al. |
| 2006/0281077 | A1 | 12/2006 | Lin |
| 2006/0286663 | A1 | 12/2006 | Cunningham et al. |
| 2007/0041012 | A1 | 2/2007 | Cunningham et al. |
| 2007/0054339 | A1 | 3/2007 | Lin |
| 2007/0070355 | A1 | 3/2007 | Cunningham et al. |
| 2007/0141231 | A1 | 6/2007 | Cunningham et al. |

FOREIGN PATENT DOCUMENTS

| | | |
|---|---|---|
| CA | 2395318 | 2/2001 |
| CA | 2394966 | 8/2001 |
| CA | 2395318 | 8/2001 |
| CH | 669050 A5 | 2/1989 |
| CH | 670521 A5 | 6/1989 |
| EP | 0 112 721 | 7/1987 |
| EP | 0326219 | 1/1989 |
| EP | 0326291 | 2/1989 |
| EP | 0 517 777 | 12/1992 |
| EP | 0 660 924 | 7/1995 |
| FR | 2801977 | 2/1999 |
| FR | 2801977 | 12/1999 |
| GB | 2156970 A | 10/1985 |
| GB | 2 227 089 | 7/1990 |
| WO | 8100912 | 4/1981 |
| WO | 0075353 | 3/1983 |
| WO | 8 402 578 | 7/1984 |
| WO | 8607149 | 12/1986 |
| WO | 9 008 831 | 7/1990 |
| WO | 9 113 339 | 9/1991 |
| WO | 9204653 | 3/1992 |
| WO | 9 221 768 | 12/1992 |
| WO | 9 314 392 | 7/1993 |
| WO | 9 503 538 | 2/1995 |
| WO | 9 857 200 | 12/1998 |
| WO | 9 909 392 | 2/1999 |
| WO | 9 909 396 | 2/1999 |
| WO | 9954714 | 10/1999 |
| WO | 9 966 330 | 12/1999 |
| WO | 0 023 793 | 4/2000 |
| WO | 0029830 | 5/2000 |
| WO | 0 104 697 | 1/2001 |
| WO | WO 01/79559 | 10/2001 |
| WO | WO 02/061429 | 8/2002 |

OTHER PUBLICATIONS

Challener, et al., "A multilayer grating-based evanescent wave sensing technique", Elsevier Science B.V., pp. 42-46.

Cowan, "Aztec Surface-Relief Volume Diffractive Structure", vol. 7, No. 8, J. Opt. Soc. Am., pp. 1529-1544 (1990).

Cowan, "Holographic honeycomb microlens", vol. 24, No. 5, Optical Engineering, pp. 796-802 (1985).

Cowan, "The Recording and Large Scale Replication of Crossed Holographic Grating Arrays using Multiple Beam Interometry", SPIE vol. 503, Application, Theory, and Fabrication of Periodic Structures, pp. 120-129 (1984).

Cowan, et al., "The Recording and Replication of Holographic Micropatterns for the Ordering of Photographic Emulsion Grains in Film Systems", vol. 31, No. 3, J. Imaging Sci., pp. 100-107 (1987).

Cunningham, et al., "Introduction to Bioanalytical Sensors", Techniques in Analytical Chemistry, pp. 260-291.

Cunningham, et al., "Resonant Reflection Microarray", U.S. Appl. No. 60/244,312, filed Oct. 30, 2000.

Cunningham, et al., "Resonant Reflection Microarray", U.S. Appl. No. 60/283,314, filed Apr. 12, 2001.

Cunningham, et al., "Resonant Reflection Microarray", U.S. Appl. No. 60/303,028, filed Jul. 3, 2001.

Hobbs, et al., "Automated Interference Lithography Systems for Generation of Sub-Micron Feature Size Patterns", SPIE, vol. 3879, pp. 124-135, Sep. 1999.

Huber, et al., "Direct Optical Immunosensing (Sensitivity and Selectivity)", Sensors and Actuators B, 6, pp. 122-126, (1992).

Jenison, et al., "Interference-Based Detection of Nucleic Acid Targets on Optically Coated Silicon", vol. 19, Nature Biotechnology, pp. 62-64 (2001).

Jin, et al., "A Biosensor Concept Based on Imaging Ellipsometry for Visualization of Biomolecular Interactions", 232, Analytical Biochemistry, pp. 69-72 (1995).

Jordon, et al., "Surface Plasmon Resonance Imaging Measurements of Electrostatic Biopolymer Adsorption onto Chemically Modified Gold Surfaces", vol. 69, No. 7, Analytical Chemistry, pp. 1449-1456 (1997).

Lin, et al., "A Porous Silicon-Based Optical Interferometric Biosensor", vol. 278, Science, pp. 840-843 (1997).

Magnusson, et al., "New Principle for Optical Filters", vol. 61, No. 9, Appl. Phys. Lett., pp. 1022-1024 (1992).

Magnusson, et al., "Transmission Bandpass Guided-Mode Resonance Filters", vol. 34, No. 35, Applied Optics, pp. 8106-8109 (1995).

Morhard, et al., "Immobilization of Antibodies in Micropatterns Detection for Cell Detection by Optical Diffraction", Sensors and Actuators B 70, pp. 232-242 (2000).

Patel, et al., "Electrically Tunable and Polarization Insensitive Fabry-Perot Etalon with a Liquid-Crystal Film", vol. 58, No. 22, American Institute of Physics, pp. 2491-2493 (1991).

Patel, et al., "Multiwavelength Tunable Liquid-Crystal Etalon Filter", vol. 3, No. 7, IEEE Photonics Technology Letters, pp. 643-644 (1991).

Peng, et al., "Experimental Demonstration of Resonant Anomalies in Diffraction from Two-Dimensional Gratings", vol. 21, No. 8, Optics Letters, pp. 549-551 (1996).

Peng, et al., "Resonant Scattering from Two-Dimensional Gratings", vol. 13, No. 5, J. Opt. Soc. Am. A., pp. 993-1005 (1996).

Raguin, et al., "Structured Surfaces Mimic Coating Performance", Laser Focus World, pp. 113-117 (1997).

Sigal, et al., "A Self-Assembled Monolayer for the Binding and Study of Histidine-Tagged Proteins by Surface Plasmon Resonance", vol. 68, No. 3, Analytical Chemistry, pp. 490-497 (1996).

Wang, et al., "Design of Waveguide-Grating Filters with Symmetrical Line Shapes and Low Sidebands", vol. 19, No. 12, Optical Society of America, pp. 919-921 (1994).

Wang, et al., "Guided-mode Resonances in Planar Dielectric-Layer Diffraction Gratings", vol. 7, No. 8, J. Opt. Soc. Am., pp. 1470-1474 (1990).

Wang, et al., "Theory and Applications of Guided-Mode Resonance Filters", vol. 32, No. 14, Applied Optics, pp. 2606-2613 (1993).

Invitation to Pay Additional Fees in forgeign counterpart application PCT/US01/50723.

International Search Report for foreign counterpart application PCT/US01/50723.

Cunningham et al., Sensors and Actuators B 85; pp. 219-226 (2002).

Cunningham et al., Sensors and Actuators B 81; pp. 316-328 (2002).

Pandey, A. and Mann, M., Nature. 405(6788):837-46 (2000).

Patterson, S.D., Current Opinions in Biotechnology, 11(4):413-8 (2000).

International Search Report for foreign counterpart application PCT/US03/01175.

Lenau, Torben; Material, Silicon Nitride, 1996, 97, 98.

Cerac, Technical publications: Tantalum Oxide, $Ta_2O_5$ for Optical Coating, 2000, Cerac, Inc.

Bertoni, et al., "Frequency-Selective Reflection and Transmission by a Periodic Dielectric Layer", IEEE Transactions on Antennas and Propagation, vol. 37, No. 1, pp. 78-83 (1989).

Brundrett, et al., "Normal-incidence guided-mode resonant grating filters: design and experimental demonstration", Optics Letters, vol. 23, No. 9, pp. 700-702 (1998).

Peng, "Polarization-control Components and Narrow-band Filters Based on Subwavelength Grating Structures" 1996.

Statement of Applicants dated Jun. 7, 2004.

U.S. Appl. No. 09/929,957, filed Aug. 15, 2001*.

U.S. Appl. No. 09/930,352, filed Aug. 15, 2001*.

U.S. Appl. No. 10/415,037, filed Oct. 23, 2001*.

U.S. Appl. No. 10/399,940, filed Oct. 23, 2001*.

U.S. Appl. No. 10/059,060, filed Jan. 28, 2002.

U.S. Appl. No. 10/201,818, filed Jul. 23, 2002*.

U.S. Appl. No. 10/237,641, filed Sep. 9, 2002*.
U.S. Appl. No. 10/277,908, filed Aug. 26, 2002*.
U.S. Appl. No. 10/233,730, filed Sep. 3, 2002*.
U.S. Appl. No. 10/180,374, filed Jun. 26, 2002*.
U.S. Appl. No. 10/180,647, filed Jun. 26, 2002*.
U.S. Appl. No. 10/253,846, filed Sep. 25, 2002*.
U.S. Appl. No. 10/196,058, filed Jul. 15, 2002*.
U.S. Appl. No. 10/667,696, filed Sep. 22, 2003*.
U.S. Appl. No. 10/058,626, filed Jan. 28, 2002*.
U.S. Appl. No. 10/415,037, filed Oct. 23, 2001.
U.S. Appl. No. 10/059,060, filed Jan. 28, 2002*.
U.S. Appl. No. 10/180,647, filed Jun.26, 2002*.
Anderson, et al., "Proteomics: applications in basic and applied biology", *Current Opinion in Biotechnology*, 2000, 11:408-412.
MacBeath, et al., "Printing Proteins as Microarrays for High-Throughput Function Determination",*Science*, vol. 289, pp. 1760-1763, 2000
deWildt, et a., "Antibody arrays for high-throughput screening of antibody-antigen interactions", *Nature Biotechnology*, vol. 18, pp. 989-994, 2000.
Cunningham, et al., "A plastic colorimetric resonant optical biosensor for multiparallel detection of label-free biochemical interactions", *Sensors and Actuators B*, 85 (2002) 219-226.
Caruso, et al., "Quartz Crystal Microbalance Study of DNA Immobilization and Hybridization for Nucleic Acid Sensor Development", *Analytical Chemistry*, vol. 69, No. 11, pp. 2043-2049, 1997.
Hefti, et al, "Sensitive detection method of dielectric dispersions in aqueous-based, surface-bound macromolecular structures using microwave spectroscopy", *Applied Physics Letters*, vol. 75, No. 12, pp. 1802-1804, 1999.
Wu, et al., "Bioassay of prostate-specific antigen (PSA) using microcantilevers", *Nature Biotechnology*, vol. 19, pp. 856-860, 2001.
Wasserman, et al., "Structure and Reactivity of Alkylsiloxane Monolayers Formed by Reaction of Alkyltrichlorosilanes on Silicon Substrates", *Langmuir*, 5, 1074-1087, 1989.
Kallury, et al., "X-ray Photoelectron Spectroscopy of Silica Surfaces Treated with Polyfunctional Silanes", *Anal. Chem.*, 60, 169-172, 1988.
Cunningham, et al., "Colorimetric resonant reflection as a direct biochemical assay technique", *Sensors and Actuators B*, 81 (2002) 316-328.
Mullaney, et al., "Epitope Mapping of Neutralizing Botulinum Neurotoxin A Antibodies by Phage Display", *Infection and Immunity*, vol. 69, No. 10, pp. 6511-6514, 2001.
Neuschafer et al., "Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
Nellen, et al., "Integrated Optical Input Grating Couplers as Biochemical Sensors", *Sensors and Actuators*, 15 (1988) 285-295.
W. Lukosz and K. Tiefenthaler, "Embossing technique for fabricating integrated optical components in hard inorganic waveguiding materials," *Optical Letters*, vol. 8, pp. 537-539 (1983).
K. Tiefenthaler and W. Lukosz, "Integrated optical switches and gas sensors," *Optics Letters*, vol. 10, pp. 137-139 (1984).
Chabay, "Optical Waveguides," *Analytical Chemistry*, vol. 54, pp. 1071A-1080A (1982).
Sutherland et al., "Optical Detection of Antibody-Antigen Reactions at a Glass-Liquid Interface," *Clin. Chem.*, vol. 30, pp. 1533-1538 (1984).
Ronald T. Holm and Edward D. Palik, "Internal-reflection spectroscopy," *Laser Focus*, vol. 15, pp. 60-65 (Aug. 1979).
N.J. Harrick and George I. Loeb, "Multiple Internal Reflection Fluorescence Spectrometry," *Analytical Chemistry*, vol. 45, pp. 687-691 (1973).
P.K. Tien, "Light Waves in Thim Films and Integrated Optics," *Applied Optics*, vol. 10, pp. 2395-2413 (1971).
Dakss, et al., "Grating Coupler for Efficient Excitation of Optical Guided Waves in Thin Films," *Applied Physics Letters*, vol. 16, pp. 523-525 (1970).
Sutherland et al., "Immunoassays at a Quartz-Liquid Interface: Theory, Instrumentation and Preliminary Application to the Fluorescent Immunoassay of Human Immunoglobulin G," *Journal of Immunological Methods*, vol. 74, pp. 253-265 (1984).
English translation of CH 670 521 A5.
English translation of CH 669 050 A5.
Haidner, "Zero-Order Gratings Used as an Artifical Distributed Index Medium", *Optik, Wissenschaftlich Verlag GmbH, Stuttgart, DE*, vol. 89, No. 3, pp. 107-112, 1992.
Peng, et al., "Experimental Demonstration of Resonant Anomalies in Diffraction from two-Dimensional Gratings", *Optics Letters, Optical Society of America*, vol. 21, No. 9, pp. 549-551, 1996.
Wilson, et al., "The Optical Properties 1-19 of 'Moth Eye' Antireflection Surfaces", *Optical ACTA*, vol. 29, No. 7, pp. 993-1009, 1982.
Bagnich, et al., "*Tunable Optical Filter*", SU 1465855, Derwent Publications, English Translation, Abstract Only, Derwent Publications Ltd.
Huber, et al., "Direct Optical immunosensing (Sensitivity and Selectivity)", *Snesors and Actuators B*, 6, p. 122-126 (1992).
Liu, et al., "Development of an optical fiber lactate sensor", Mikrochimica Acta, 1999, 131(1-2), pp. 129-135.
Cunningham, et al. "Label-Free Assays on the BIND System", The Society for Biomolecular Screening, p. 481490 (2004).
Cunningham, "Label-Free Detection with the BIND System", Presented at Screentech General, Mar. 24, 2003.
Baird, "Beyond Elisa's: Label-free Detection with BIND", Presented at Interphex Meeting in Europe, Mar. 16-18, 2004.
Cunningham, et al., "Colorimetric Resonant Reflection as a Direct Biochemical Assay Technique", Presented at the Pittsburgh Conference and Exposition on Anayltical Chemistry and Applied Spectroscopy, Morial Convention Center in New Orleans, LA, Mar. 17-22, 2002.
Cekaite, et al., "Analysis of the humoral immune response to immunoselected phage-displayed peptides by a microarray-based method", Proteomics 2004, 4, 2572-2582.
Sun, et al., "Use of bioluminescent *Salmonella* for assessing the efficiency of constructed phage-based biosorbent", Journal of Industrial Microbiology & Biotechnology, 2000, 25, 273-275.
Wan, et al., "Landscape phage-based magnetostrictive biosensor for detecting *Bacillus anthracis* spores", Proc. IEEE Sens., 2005, 1308-1311.
European Search Report for EP 07 11 8355 dated Feb. 5, 2003.
Nelson, et al., "BIA/MS of Epitope-Tagged Peptides Directly from *E. Coli* Lysate: Multiplex Detection and Protein Identification at Low-Femtomole to Subfemtomole Levels" Anal. Chem. 1999, 71, 2858-2865.
Moffatt, "Optical Probes May Hasten Shift of Diagnostics from Lab to Doc's Office" Genetic Engineering News, vol. 18 (1986) p. 18.
Williams, et al., "The integration of SPR biosensors with mass spectrometry: possible applications for proteome analysis", Trends in Microbiology, Elsevier, vol. 18, No. 2, (2000) pp. 45-48.
U.S. Appl. No. 11/635,934, filed Dec. 8, 2006.
U.S. Appl. No. 11/566,818, filed Dec. 5, 2006.
U.S. Appl. No. 11/506,639, filed Aug. 18, 2007.
U.S. Appl. No. 11/749,073, filed May. 15, 2007.
U.S. Appl. No. 11/828,076, filed Jul. 25, 2007.

* cited by examiner

Amine
- Sulfo-succinimidyl-6-(biotinamido)hexanoate (Sulfo-NHS-LC-Biotin)
  - Streptavidin / avidin then biotinylated molecule
- N,N'-disuccinimidyl carbonate (DSC); • -NH$_2$, non-cleavable
- Dimethyl pimelimidate (DMP); • -NH$_2$, non-cleavable
- Dimethyl 3,3'-dithiobispropionimidate (DTBP); • -NH$_2$, cleavable
- 1-Ethyl-3-(3-Dimethylaminopropyl)carbodiimide Hydrochloride (EDC) and N-Hydroxysulfosuccinimide (Sulfo-NHS); • -COOH
- Sulfo-succinimidyl 6-[a-methyl-a-(2-pyridyl-dithio)toluamido] hexanoate (Sulfo-LC-SMPT); • -SH, cleavable
- N-(B-Maleimidopropyloxy)succinimide ester (BMPS)
  - -SH$_2$, non-cleavable
- Sulfo-succinimidyl 4-[N-maleimidomethyl)cyclohexane-1-carboxylate (Sulfo-SMCC); • -SH, non-cleavable Aldehyde
- Directly with aldehyde or first amino then aldehyde
  - -NH$_2$ Ni(II)
- Using Nitrilotriacetic acid (NTA) group, which forms a chelate with Ni(II)
  - His-tagged molecules

Figure 6

Measured shifting of the resonant wavelength caused by the binding of various biomolecular layers.

Material 1 = Electrical Insulator (photoresist, epoxy, glass)
Material 2 = Indium tin oxide conductor
Substrate = Glass

Concentric Circle Design

Hexagonal Grid Design

LABEL-FREE HIGH-THROUGHPUT OPTICAL TECHNIQUE FOR DETECTING BIOMOLECULAR INTERACTIONS

TECHNICAL AREA OF THE INVENTION

The invention relates to compositions and methods for detecting biomolecular interactions. The detection can occur without the use of labels and can be done in a high-throughput manner. The invention also relates to optical devices.

BACKGROUND OF THE INVENTION

With the completion of the sequencing of the human genome, one of the next grand challenges of molecular biology will be to understand how the many protein targets encoded by DNA interact with other proteins, small molecule pharmaceutical candidates, and a large host of enzymes and inhibitors. See e.g., Pandey & Mann, "Proteomics to study genes and genomes," *Nature*, 405, p. 837-846, 2000; Leigh Anderson et al., "Proteomics: applications in basic and applied biology," *Current Opinion in Biotechnology*, 11, p. 408-412, 2000; Patterson, "Proteomics: the industrialization of protein chemistry," *Current Opinion in Biotechnology*, 11, p. 413-418, 2000; MacBeath & Schreiber, "Printing Proteins as Microarrays for High-Throughput Function Determination," *Science*, 289, p. 1760-1763, 2000; De Wildt et al., "Antibody arrays for high-throughput screening of antibody-antigen interactions," *Nature Biotechnology*, 18, p. 989-994, 2000. To this end, tools that have the ability to simultaneously quantify many different biomolecular interactions with high sensitivity will find application in pharmaceutical discovery, proteomics, and diagnostics. Further, for these tools to find widespread use, they must be simple to use, inexpensive to own and operate, and applicable to a wide range of analytes that can include, for example, polynucleotides, peptides, small proteins, antibodies, and even entire cells.

Biosensors have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence, interferometry (Jenison et al., "Interference-based detection of nucleic acid targets on optically coated silicon," *Nature Biotechnology*, 19, p. 62-65; Lin et al., "A porous silicon-based optical interferometric biosensor," *Science*, 278, p. 840-843, 1997), and gravimetry (A. Cunningham, Bioanalytical Sensors, John Wiley & Sons (1998)).

Of the optically-based transduction methods, direct methods that do not require labeling of analytes with fluorescent compounds are of interest due to the relative assay simplicity and ability to study the interaction of small molecules and proteins that are not readily labeled. Direct optical methods include surface plasmon resonance (SPR) (Jordan & Corn, "Surface Plasmon Resonance Imaging Measurements of Electrostatic Biopolymer Adsorption onto Chemically Modified Gold Surfaces," *Anal. Chem.*, 69:1449-1456 (1997), (grating couplers (Morhard et al., "Immobilization of antibodies in micropatterns for cell detection by optical diffraction," *Sensors and Actuators B*, 70, p. 232-242, 2000), ellipsometry (Jin et al., "A biosensor concept based on imaging ellipsometry for visualization of biomolecular interactions," *Analytical Biochemistry*, 232, p. 69-72, 1995), evanescent wave devices (Huber et al., "Direct optical immunosensing (sensitivity and selectivity)," *Sensors and Actuators B*, 6, p. 122-126, 1992), and reflectometry (Brecht & Gauglitz, "Optical probes and transducers," *Biosensors and Bioelectronics*, 10, p. 923-936, 1995). Theoretically predicted detection limits of these detection methods have been determined and experimentally confirmed to be feasible down to diagnostically relevant concentration ranges. However, to date, these methods have yet to yield commercially available high-throughput instruments that can perform high sensitivity assays without any type of label in a format that is readily compatible with the microtiter plate-based or microarray-based infrastructure that is most often used for high-throughput biomolecular interaction analysis. Therefore, there is a need in the art for compositions and methods that can achieve these goals.

SUMMARY OF THE INVENTION

It is an object of the invention to provide compositions and methods for detecting binding of one or more specific binding substances to their respective binding partners. This and other objects of the invention are provided by one or more of the embodiments described below.

One embodiment of the invention provides a biosensor comprising: a two-dimensional grating comprised of a material having a high refractive index, a substrate layer that supports the two-dimensional grating, and one or more specific binding substances immobilized on the surface of the two-dimensional grating opposite of the substrate layer. When the biosensor is illuminated a resonant grating effect is produced on the reflected radiation spectrum. The depth and period of the two-dimensional grating are less than the wavelength of the resonant grating effect.

Another embodiment of the invention provides an optical device comprising a two-dimensional grating comprised of a material having a high refractive index and a substrate layer that supports the two-dimensional grating. When the optical device is illuminated a resonant grating effect is produced on the reflected radiation spectrum. The depth and period of the two-dimensional grating are less than the wavelength of the resonant grating effect.

A narrow band of optical wavelengths can be reflected from the biosensor or optical device when the biosensor is illuminated with a broad band of optical wavelengths. The substrate can comprise glass, plastic or epoxy. The two-dimensional grating can comprise a material selected from the group consisting of zinc sulfide, titanium dioxide, tantalum oxide, and silicon nitride.

The substrate and two-dimensional grating can optionally comprise a single unit. The surface of the single unit comprising the two-dimensional grating is coated with a material having a high refractive index, and the one or more specific binding substances are immobilized on the surface of the material having a high refractive index opposite of the single unit. The single unit can be comprised of a material selected from the group consisting of glass, plastic, and epoxy.

The biosensor or optical device can optionally comprise a cover layer on the surface of the two-dimensional grating opposite of the substrate layer. The one or more specific binding substances are immobilized on the surface of the cover layer opposite of the two-dimensional grating. The cover layer can comprise a material that has a lower refractive index than the high refractive index material of the two-dimensional grating. For example, a cover layer can comprise glass, epoxy, and plastic.

A two-dimensional grating can be comprised of a repeating pattern of shapes selected from the group consisting of lines, squares, circles, ellipses, triangles, trapezoids, sinusoidal waves, ovals, rectangles, and hexagons. The repeating pattern of shapes can be arranged in a linear grid, i.e., a grid of parallel lines, a rectangular grid, or a hexagonal grid. The two-dimensional grating can have a period of about 0.01 microns to about 1 micron and a depth of about 0.01 microns to about 1 micron.

The one or more specific binding substances can be arranged in an array of distinct locations and can be immobilized on the two-dimensional grating by physical adsorption or by chemical binding. The distinct locations can define a microarray spot of about 50-500 or 150-200 microns in diameter. The one or more specific binding substances can be bound to their binding partners. The one or more specific binding substances can be selected from the group consisting of nucleic acids, polypeptides, antigens, polyclonal antibodies, monoclonal antibodies, single chain antibodies (scFv), F(ab') fragments, F(ab')$_2$ fragments, Fv fragments, small organic molecules, cells, viruses, bacteria, and biological samples. The biological sample can be selected from the group consisting of blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatic fluid. The binding partners can be selected from the group consisting of nucleic acids, polypeptides, antigens, polyclonal antibodies, monoclonal antibodies, single chain antibodies (scFv), F(ab) fragments, F(ab')$_2$ fragments, Fv fragments, small organic molecules, cells, viruses, bacteria, and biological samples. The biosensor can further comprise an antireflective dielectric coating on a surface of the substrate opposite of the two-dimensional grating. The biosensor can comprise an antireflective physical structure that is embossed into a surface of the substrate opposite of the two-dimensional grating, such as a motheye structure. The biosensor can comprise an internal surface of a liquid-containing vessel. The vessel is selected from the group consisting of a microtiter plate, a test tube, a petri dish and a microfluidic channel. The biosensor can be attached to a bottomless microtiter plate by a method selected from the group consisting of adhesive attachment, ultrasonic welding and laser welding.

Another embodiment of the invention provides a detection system comprising a biosensor or optical device of the invention, a light source that directs light to the biosensor or optical device, and a detector that detects light reflected from the biosensor. The detection system can comprise a fiber probe comprising one or more illuminating optical fibers that are connected at a first end to the light source, and one or more collecting optical fibers connected at a first end to the detector, wherein the second ends of the illuminating and collecting fibers are arranged in line with a collimating lens that focuses light onto the biosensor or optical device. The illuminating fiber and the collecting fiber can be the same fiber. The light source can illuminate the biosensor from its top surface or from its bottom surface.

Even another embodiment of the invention provides a method of detecting the binding of one or more specific binding substances to their respective binding partners. The method comprises applying one or more binding partners to a biosensor of the invention, illuminating the biosensor with light, and detecting a maxima in reflected wavelength, or a minima in transmitted wavelength of light from the biosensor. Where one or more specific binding substances have bound to their respective binding partners, the reflected wavelength of light is shifted.

Still another embodiment of the invention provides a method of detecting the binding of one or more specific binding substances to their respective binding partners. The method comprises applying one or more binding partners to a biosensor of the invention, wherein the biosensor comprises a two-dimensional grating that is coated with an array of distinct locations containing the one or more specific binding substances. Each distinct location of the biosensor is illuminated with light, and maximum reflected wavelength or minimum transmitted wavelength of light is detected from each distinct location of the biosensor. Where the one or more specific binding substances have bound to their respective binding partners at a distinct location, the reflected wavelength of light is shifted.

Yet another embodiment of the invention provides a method of detecting activity of an enzyme. The method comprises applying one or more enzymes to a biosensor of the invention, washing the biosensor, illuminating the biosensor with light, and detecting reflected wavelength of light from the biosensor. Where the one or more enzymes have altered the one or more specific binding substances of the biosensor by enzymatic activity, the reflected wavelength of light is shifted.

Another embodiment of the invention provides a biosensor comprising a sheet material having a first and second surface, wherein the first surface defines relief volume diffraction structures, a reflective material coated onto the first surface of the sheet material, and one or more specific binding substances immobilized on the reflective material. Still another embodiment of the invention provides an optical device comprising a sheet material having a first and second surface, wherein the first surface defines relief volume diffraction structures, and a reflective material coated onto the first surface of the sheet material. The biosensor or optical device reflects light predominantly at a first single optical wavelength when illuminated with a broad band of optical wavelengths. The biosensor reflects light at a second single optical wavelength when the one or more specific binding substances are immobilized on the reflective surface. The reflection at the first and second optical wavelengths results from optical interference. The biosensor can reflect light at a third single optical wavelength when the one or more specific binding substances are bound to their respective binding partners. The reflection at the third optical wavelength results from optical interference. The depth and period of the relief volume diffraction structures can be less than the resonance wavelength of the light reflected from the biosensor. The depth of the relief volume diffraction structures can be about 0.01 microns to about 1 micron. The period of the relief volume diffraction structures can be about 0.01 microns to about 1 micron. The relief volume diffraction structures can be about 0.5 microns to about 5 microns in diameter.

Even another embodiment of the invention provides a biosensor comprising a two-dimensional grating having a first and a second surface comprised of an optically transparent material that conducts electricity. The first surface of the grating is coated with an electrical insulator, and the second surface of the grating is deposited on a substrate. When the biosensor is illuminated, a resonant grating effect is produced on the reflected radiation spectrum. The depth and the period of the grating are less than the wavelength of the resonant grating effect. Two or more separate grating regions can be present on the same substrate. An electrically conducting trace to each separate grating region of the substrate can be present. The conducting trace can be connected to a voltage source. One or more specific binding substances can be bound to each separate grating region of the substrate.

Yet another embodiment of the invention provides a method of measuring the amount of binding partners in a test sample. One or more binding partners are immobilized to the biosensor described above. An electrical charge is applied to the electrically conducting traces. The biosensor is illuminated with light and the reflected wavelength of light is detected from the biosensor. Where the one or more specific binding substances have bound to their respective binding partners, the reflected wavelength of light is shifted. A reversed electrical charge can be applied to the electrically conducting traces before illuminating the biosensor with light.

Still another embodiment of the invention provides a method of detecting the binding of one or more specific binding substances to their respective binding partners. The method comprises illuminating a biosensor of the invention with light, detecting reflected wavelength of light from the biosensor, applying a test sample comprising one or more binding partners to the biosensor, illuminating the biosensor with light, and detecting reflected wavelength of light from the biosensor. The difference in wavelength of light is a measurement of the amount of one or more binding partners in the test sample.

Another embodiment of the invention provides a detection system comprising a biosensor of the invention, a light source that directs light at the biosensor, and a detector that detects light reflected from the biosensor. A first illuminating fiber probe having two ends is connected at its first end to the detector. A second collection fiber probe having two ends is connected at its first end to the light source. The first and second fiber probes are connected at their second ends to a third fiber probe, which acts as an illumination and collection fiber probe. The third fiber probe is oriented at a normal angle of incidence to the biosensor and supports counter-propagating illuminating and reflecting optical signals.

Even another embodiment of the invention provides a detection system comprising a biosensor of the invention, a light source that directs light at the biosensor, and a detector that detects light reflected from the biosensor. An illuminating fiber probe is connected to the light source and is oriented at a 90 degree angle to a collecting fiber probe. The collecting fiber probe is connected to the detector, wherein light is directed through the illuminating fiber probe into a beam splitter that directs the light to the biosensor. Reflected light is directed into the beam splitter that directs the light into the collecting fiber.

Still another embodiment of the invention comprises a method of immobilizing one or more specific binding substances onto a biosensor of the invention. The method comprises activating the biosensor with amine, attaching linker groups to the amine-activated biosensor, and attaching one or more specific binding substances to the linker groups. The biosensor can be activated with amine by a method comprising immersing the biosensor into a piranha solution, washing the biosensor, immersing the biosensor in 3% 3-aminopropyltriethoxysilane solution in dry acetone, washing the biosensor in dry acetone, and washing the biosensor with water. A linker can be selected from the group consisting of amine, aldehyde, N,N'-disuccinimidyl carbonate, and nickel.

Yet another embodiment of the invention provides a method of detecting the binding of one or more specific binding substances to their respective binding partners. The method comprises applying one or more binding partners comprising one or more tags to a biosensor of the invention, illuminating the biosensor with light, and detecting reflected wavelength of light from the biosensor. Where the one or more specific binding substances have bound to their respective binding partners, the reflected wavelength of light is shifted. The one or more tags can be selected from the group consisting of biotin, SMPT, DMP, NNDC, and histidine. The one or more tags can be reacted with a composition selected from the group consisting of streptavidin, horseradish peroxidase, and streptavidin coated nanoparticles, before the step of illuminating the biosensor with light.

Another embodiment of the invention provides a biosensor composition comprising two or more biosensors of the invention, where the biosensors are associated with a holding fixture. The biosensor composition can comprise about 96, about 384, or about 50 to about 1,000 individual biosensors. Each of the two or more biosensors can comprise about 25 to about 1,000 distinct locations. Each biosensor can be about 1 $mm^2$ to about 5 $mm^2$, or about 3 $mm^2$. The holding fixture can hold each biosensor such that each biosensor can be placed into a separate well of a microtiter plate.

Even another embodiment of the invention provides a biosensor composition comprising one or more biosensors of the invention on a tip of a multi-fiber optic probe. The one or more biosensors can be fabricated into the tip of the probe or can be attached onto the tip of the probe.

Still another embodiment of the invention provides a method of detecting binding of one or more specific binding substances to their respective binding partners in vivo. The method comprises inserting the tip of the fiber optic probe described above into the body of a human or animal, illuminating the biosensor with light, and detecting reflected wavelength of light from the biosensor. If the one or more specific binding substances have bound to their respective binding partners, then the reflected wavelength of light is shifted.

Yet another embodiment of the invention provides a detection system comprising a biosensor of the invention, a laser source that directs a laser beam to a scanning mirror device, wherein the scanning mirror device is used to vary the laser beam's incident angle, an optical system for maintaining columination of the incident laser beam, and a light detector. The scanning mirror device can be a linear galvanometer. The linear galvanometer can operate at a frequency of about 2 Hz to about 120 Hz and a mechanical scan angle of about 10 degrees to about 20 degrees. The laser can be a diode laser with a wavelength selected from the group consisting of 780 nm, 785 nm, 810 nm, and 830 nm.

Another embodiment of the invention provides a method for determining a location of a resonant peak for a binding partner in a resonant reflectance spectrum with a colorimetric resonant biosensor. The method comprises selecting a set of resonant reflectance data for a plurality of colorimetric resonant biosensor distinct locations. The set of resonant reflectance data is collected by illuminating a colorimetric resonant diffractive grating surface with a light source and measuring reflected light at a pre-determined incidence. The colorimetric resonant diffractive grating surface is used as a surface binding platform for one or more specific binding substances and binding partners can be detected without the use of a molecular label. The set of resonant reflectance data includes a plurality of sets of two measurements, where a first measurement includes a first reflectance spectra of one or more specific binding substances that are attached to the colorimetric resonant diffractive grating surface and a second measurement includes a second reflectance spectra of the one or more specific binding substances after one or more binding partners are applied to colorimetric resonant diffractive grating surface including the one or more specific binding substances. A difference in a peak wavelength between the first and second measurement is a measurement of an amount of binding partners that bound to the one or more specific binding substances. A maximum value for a second measurement from the plurality of sets of two measurements from the set of resonant reflectance data for the plurality of binding partners is determined, wherein the maximum value includes inherent noise included in the resonant reflectance data. Whether the maximum value is greater than a pre-determined threshold is determined, and if so, a curve-fit region around the determined maximum value is determined and a curve-fitting procedure is performed to fit a curve around the curve-fit region, wherein the curve-fitting procedure removes a pre-determined amount of inherent noise included in the resonant reflectance data. A location of a maximum resonant peak on the fitted curve is determined. A value of the maximum resonant peak is determined, wherein the value of the maximum resonant peak is used to identify an amount of biomolecular binding of the one or more specific binding substances to the one or more binding partners.

The sensitivity of a colorimetric resonant biosensor can be determined by a shift in a location of a resonant peak in the plurality of sets of two measurements in the set of resonant reflectance data. The step of selecting a set of resonant reflectance data can include selecting a set of resonant reflectance data:

$x_i$ and $y_i$ for $i=1, 2, 3, \ldots n$, wherein $x_i$ is where a first measurement includes a first reflectance spectra of one or more specific binding substance attached to the colorimetric resonant diffractive grating surface, $y_i$ a second measurement includes a second reflectance spectra of the one or more specific binding substances after a plurality of binding partners are applied to colorimetric resonant diffractive grating surface including the one or more specific binding substances, and n is a total number of measurements collected. The step of determining a maximum value for a second measurement can include determining a maximum value $y_k$ such that:

$(y_k >= y_i)$ for all $i \ne k$.

The step of determining whether the maximum value is greater than a pre-determined threshold can include computing a mean of the set of resonant reflectance data, computing a standard deviation of the set of resonant reflectance data, and determining whether $((y_k-\text{mean})/\text{standard deviation})$ is greater than a pre-determined threshold. The step of defining a curve-fit region around the determined maximum value can include defining a curve-fit region of $(2w+1)$ bins, wherein w is a pre-determined accuracy value, extracting $(x_i, k-w<=i<=k+w)$, and extracting $(y_i, k-w<=i<=k+w)$. The step of performing a curve-fitting procedure can include computing $g_i = \ln y_i$, performing a $2^{nd}$ order polynomial fit on $g_i$ to obtain $g'_i$ defined on $(x_i, k-w<=i<=k+w)$, determining from the $2^{nd}$ order polynomial fit coefficients a, b and c of for $(ax^2+bx+c)$–, and computing $y'_i = e^{g'_i}$. The step of determining a location of a maximum resonant peak on the fitted curve can include determining location of maximum resonant peak $(x_p = (-b)/2a)$. The step of determining a value of the maximum resonant peak can include determining the value with of $x_p$ at $y'_p$.

Even another embodiment of the invention comprises a computer readable medium having stored therein instructions for causing a processor to execute the methods for determining a location of a resonant peak for a binding partner in a resonant reflectance spectrum with a colorimetric resonant biosensor, as described above.

Another embodiment of the invention provides a resonant reflection structure comprising a two-dimensional grating arranged in a pattern of concentric rings. The difference between an inside diameter and an outside diameter of each concentric ring is equal to about one-half of a grating period, wherein each successive ring has an inside diameter that is about one grating period greater than an inside diameter of a previous ring. When the structure is illuminated with an illuminating light beam, a reflected radiation spectrum is produced that is independent of an illumination polarization angle of the illuminating light beam. A resonant grating effect can be produced on the reflected radiation spectrum, wherein the depth and period of the two-dimensional grating are less than the wavelength of the resonant grating effect, and wherein a narrow band of optical wavelengths is reflected from the structure when the structure is illuminated with a broad band of optical wavelengths. One or more specific binding substances can be immobilized on the two-dimensional grating. The two-dimensional grating can have a period of about 0.01 microns to about 1 micron and a depth of about 0.1 micron to about 1 micron.

Even another embodiment of the invention provides a transmission filter structure comprising a two-dimensional grating arranged in a pattern of concentric rings. The difference between an inside diameter and an outside diameter of each concentric ring is equal to about one-half of a grating period, wherein each successive ring has an inside diameter that is about one grating period greater than an inside diameter of a previous ring. When the structure is illuminated with an illuminating light beam, a transmitted radiation spectrum is produced that is independent of an illumination polarization angle of the illuminating light beam. The structure of can be illuminated to produce a resonant grating effect on the reflected radiation spectrum, wherein the depth and period of the two-dimensional grating are less than the wavelength of the resonant grating effect, and wherein a narrow band of optical wavelengths is reflected from the structure when the structure is illuminated with a broad band of optical wavelengths. One or more specific binding substances can be immobilized on the two-dimensional grating. The two-dimensional grating can have a period of about 0.01 microns to about 1 micron and a depth of about 0.01 microns to about 1 micron.

Still another embodiment of the invention provides a resonant reflection structure comprising an array of holes or posts arranged such that the holes or posts are centered on the corners in the center of hexagons, wherein the hexagons are arranged in a closely packed array. When the structure is illuminated with an illuminating light beam, a reflected radiation spectrum is produced that is independent of an illumination polarization angle of the illuminating light beam. A resonant grating effect can be produced on the reflected radiation spectrum when the structure is illuminated, wherein the depth or height and period of the array of holes or posts are less than the wavelength of the resonant grating effect, and wherein a narrow band of optical wavelengths is reflected from the structure when the structure is illuminated with a broad band of optical wavelengths. The resonant reflection structure can be incorporated into a biosensor wherein one or more specific binding substances are immobilized on the array of holes or posts. The holes or posts can have a period of about 0.01 microns to about 1 micron and a depth or height of about 0.01 microns to about 1 micron.

Yet another embodiment of the invention provides a transmission filter structure comprising an array of holes or posts arranged such that the holes or posts are centered on the corners and in the center of hexagons, wherein the hexagons are arranged in a closely packed array. When the structure is illuminated with an illuminating light beam, a transmitted radiation spectrum is produced that is independent of an illumination polarization angle of the illuminating light beam. When the structure is illuminated a resonant grating effect is produced on the reflected radiation spectrum, wherein the depth or height and period of the array of holes or posts are less than the wavelength of the resonant grating effect, and wherein a narrow band of optical wavelengths is reflected from the structure when the structure is illuminated with a broad band of optical wavelengths. The transmission filter structure can be incorporated into a biosensor, wherein one or more specific binding substances are immobilized on the array of holes or posts. The holes or posts can have a period of about 0.01 microns to about 1 micron and a depth or height of about 0.01 microns to about 1 micron.

Another embodiment of the invention provides a biosensor or optical device comprising a first two-dimensional grating comprising a high refractive index material and having a top surface and a bottom surface; and a second two-dimensional grating comprising a high refractive index material and having a top surface and a bottom surface, wherein the top surface of the second two-dimensional grating is attached to the bottom surface of the first two-dimensional grating. When the biosensor or optical device is illuminated two resonant grating effects are produced on the reflected radiation spectrum and the depth and period of both of the two-dimensional gratings are less than the wavelength of the resonant grating effects. A substrate layer can support the bottom surface of the second two-dimensional grating. The biosensor can further comprise one or more specific binding substances or one or more specific binding substances bound to their binding partners immobilized on the top surface of the first two-dimensional grating. The biosensor or optical device can further comprising a cover layer on the top surface of the first two-dimensional grating, wherein the one or more specific binding substances are immobilized on the surface of the cover layer opposite of the two-dimensional grating. The top surface of the first two-dimensional grating can be in physical contact with a test sample, and the second two dimensional grating may not be in physical contact with the test sample. A peak resonant reflection wavelength can be measured for the first and second two-dimensional gratings, the difference between the two measurements indicates the amount of one or more specific binding substances, binding partners or both deposited on the surface of the first two-dimensional grating.

Even another embodiment of the invention provides a biosensor or optical device comprising: a first two-dimensional grating comprising a high refractive index material and having a top surface and a bottom surface, a substrate layer comprising a high refractive index material and having a top surface and a bottom surface, wherein the top surface of the substrate supports the bottom surface of the first two-dimensional grating, and a second two-dimensional grating comprising a top surface and a bottom surface, wherein the bottom surface of the second two-dimensional grating is attached to the bottom surface of the substrate. When the biosensor or optical device is illuminated two resonant grating effects are produced on the reflected radiation spectrum, and wherein the depth and period of both of the two-dimensional gratings are less than the wavelength of the resonant grating effects. The biosensor can comprise one or more specific binding substances or one or more specific binding substances bound to their binding partners immobilized on the top surface of the first two-dimensional grating. The biosensor or optical device can further comprise a cover layer on the top surface of the first two-dimensional grating, wherein the one or more specific binding substances are immobilized on the surface of the cover layer opposite of the two-dimensional grating. The top surface of the first two-dimensional grating can be in physical contact with a test sample, and the second two dimensional grating may not be in physical contact with the test sample. When a peak resonant reflection wavelength is measured for the first and second two-dimensional gratings, the difference between the two measurements can indicate the amount of one or more specific binding substances, binding partners or both deposited on the surface of the first two-dimensional grating.

Still another embodiment of the invention provides a method of detecting an interaction of a first molecule with a second test molecule. The method comprises applying a mixture of the first and second molecules to a distinct location on a biosensor, wherein the biosensor comprises a two-dimensional grating and a substrate layer that supports the two-dimensional grating; and wherein, when the biosensor is illuminated a resonant grating effect is produced on the reflected radiation spectrum, and wherein the depth and period of the two-dimensional grating are less than the wavelength of the resonant grating effect; applying a mixture of the first molecule with a third control molecule to a distinct location on the biosensor or a similar biosensor, wherein the third control molecule does not interact with the first molecule, and wherein the third control molecule is about the same size as the first molecule; and detecting a shift in the reflected wavelength of light from the distinct locations. Wherein, if the shift in the reflected wavelength of light from the distinct location to which a mixture of the first molecule and the second test molecule was applied is greater than the shift in the reflected wavelength from the distinct location to which a mixture of the first molecule with the third control molecule was applied, then the first molecule and the second test molecule interact. The first molecule can be selected from the group consisting of a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, and bacteria. The second test molecule can be selected from the group consisting of a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, and bacteria Therefore, unlike surface plasmon resonance, resonant mirrors, and waveguide biosensors, the described compositions and methods enable many thousands of individual binding reactions to take place simultaneously upon the biosensor surface. This technology is useful in applications where large numbers of biomolecular interactions are measured in parallel, particularly when molecular labels will alter or inhibit the functionality of the molecules under study. High-throughput screening of pharmaceutical compound libraries with protein targets, and microarray screening of protein-protein interactions for proteomics are examples of applications that require the sensitivity and throughput afforded by this approach. A biosensor of the invention can be manufactured, for example, in large areas using a plastic embossing process, and thus can be inexpensively incorporated into common disposable laboratory assay platforms such as microtiter plates and microarray slides.

BRIEF DESCRIPTION OF THE DRAWINGS

$n_1$ represents the refractive index of a cover layer. $n_2$ represents the refractive index of a two-dimensional grating. $n_{bio}$ represents the refractive index of one or more specific binding substances. $t_1$ represents the thickness of the cover layer. $t_2$ represents the thickness of the grating. $t_{bio}$ represents the thickness of the layer of one or more specific binding substances. FIG. 1A shows a cross-sectional view of a biosensor. FIG. 1B shows a diagram of a biosensor.

FIG. 6 shows three types of surface activation chemistry (Amine, Aldehyde, and Nickel) with corresponding chemical linker molecules that can be used to covalently attach various types of biomolecule receptors to a biosensor.

FIG. 10A shows a biosensor that is incorporated into a microtitre plate. FIG. 10B shows a biosensor in a microarray slide format.

FIG. 37A shows a measurement of peak resonant wavelength shift caused by attachment of a streptavidin receptor layer and subsequent detection of a biotinylated IgG. FIG. 37B shows a schematic demonstration of molecules bound to a biosensor.

FIG. 38A shows results of streptavidin detection at various concentrations for a biosensor that has been activated with $NH_2$ surface chemistry linked to a biotin receptor molecule. FIG. 38B shows a schematic demonstration of molecules bound to a biosensor.

FIG. 39A shows an assay for detection of anti-goat IgG using a goat antibody receptor molecule. BSA blocking of a detection surface yields a clearly measurable background signal due to the mass of BSA incorporated on the biosensor. A 66 nM concentration of anti-goat IgG is easily measured above the background signal. FIG. 39B shows a schematic demonstration of molecules bound to a biosensor.

FIG. 40A shows a nonlabeled ELISA assay for interferon-gamma (INF-gamma) using an anti-human IgG INF-gamma receptor molecule, and a neural growth factor (NGF) negative control. FIG. 40B shows a schematic demonstration of molecules bound to a biosensor.

FIG. 41A shows detection of a 5-amino acid peptide (MW=860) and subsequent cleavage of a pNA label (MW=130) using enzyme caspase-3. FIG. 41B shows a schematic demonstration of molecules bound to a biosensor.

FIG. 42A shows resonant peak in liquid during continuous monitoring of the binding of three separate protein layers. FIG. 42B shows a schematic demonstration of molecules bound to a biosensor.

FIG. 43A shows endpoint resonant frequencies mathematically determined from the data shown in FIG. 42. FIG. 43B shows a schematic demonstration of molecules bound to a biosensor.

FIG. 44A shows kinetic binding measurement of IgG binding. FIG. 44B shows a schematic demonstration of molecules bound to a biosensor.

FIG. 45A shows kinetic measurement of a protease that cleaves bound protein from a biosensor surface. FIG. 45B shows a schematic demonstration of molecules bound to a biosensor.

DETAILED DESCRIPTION OF THE INVENTION

Subwavelength Structured Surface (SWS) Biosensor

Figure 1:
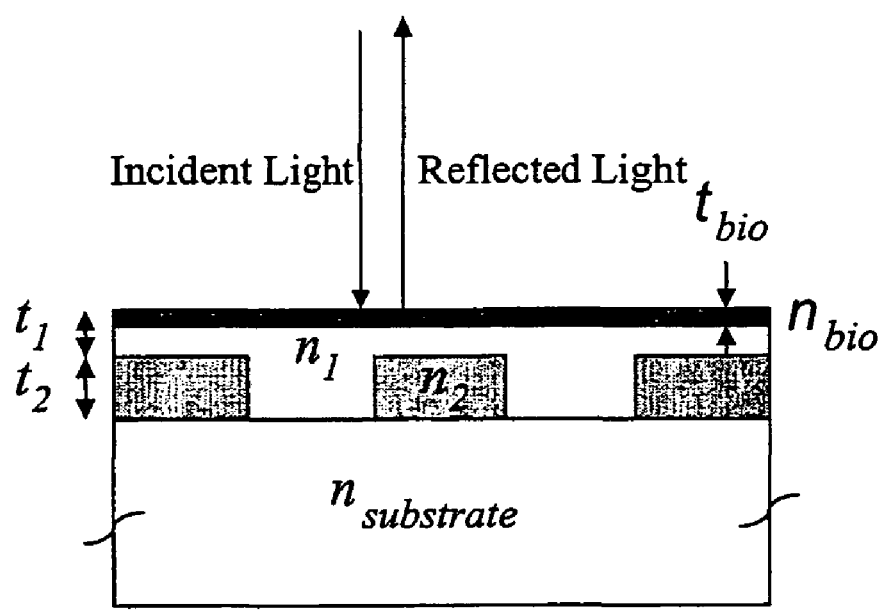
FIGS. 1A-B show schematic diagrams of one embodiment of an optical grating structure used for a colorimetric resonant reflectance biosensor. $n_{substrate}$ represents substrate material.
Figure 1:
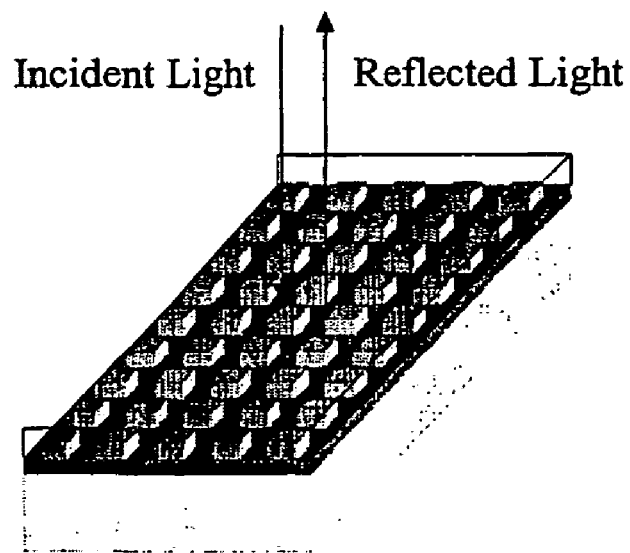

In one embodiment of the invention, a subwavelength structured surface (SWS) is used to create a sharp optical resonant reflection at a particular wavelength that can be used to track with high sensitivity the interaction of biological materials, such as specific binding substances or binding partners or both. A colorimetric resonant diffractive grating surface acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," *J. Opt. Soc. Am. A,* Vol. 13, No. 5, p. 993, May; Magnusson, & Wang, "New principle for optical filters," *Appl. Phys. Lett.,* 61, No. 9, p. 1022, August, 1992; Peng & Morris, "Experimental demonstration of resonant anomalies in diffraction from two-dimensional gratings," *Optics Letters,* Vol. 21, No. 8, p. 549, April, 1996). A SWS structure contains a surface-relief, two-dimensional grating in which the grating period is small compared to the wavelength of incident light so that no diffractive orders other than the reflected and transmitted zeroth orders are allowed to propagate. A SWS surface narrowband filter can comprise a two-dimensional grating sandwiched between a substrate layer and a cover layer that fills the grating grooves. Optionally, a cover layer is not used. When the effective index of refraction of the grating region is greater than the substrate or the cover layer, a waveguide is created. When a filter is designed properly, incident light passes into the waveguide region and propagates as a leaky mode. A two-dimensional grating structure selectively couples light at a narrow band of wavelengths into the waveguide. The light propagates only a very short distance (on the order of 10-100 micrometers), undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the two-dimensional grating are less than the wavelength of the resonant grating effect.

The reflected or transmitted color of this structure can be modulated by the addition of molecules such as specific binding substances or binding partners or both to the upper surface of the cover layer or the two-dimensional grating surface. The added molecules increase the optical path length of incident radiation through the structure, and thus modify the wavelength at which maximum reflectance or transmittance will occur.

In one embodiment, a biosensor, when illuminated with white light, is designed to reflect only a single wavelength. When specific binding substances are attached to the surface of the biosensor, the reflected wavelength (color) is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, ~0.1 nm thickness of protein binding, and can be performed with the biosensor surface either immersed in fluid or dried.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microfilter plates and microarray slides. A single spectrometer reading can be performed in several milliseconds, thus it is possible to quickly measure a large number of molecular interactions taking place in parallel upon a biosensor surface, and to monitor reaction kinetics in real time.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

A schematic diagram of an example of a SWS structure is shown in FIG. 1. In FIG. 1, $n_{substrate}$ represents a substrate material. $n_1$ represents the refractive index of an optional cover layer. $n_2$ represents the refractive index of a two-dimensional grating. $N_{bio}$ represents the refractive index of one or more specific binding substances. $t_1$ represents the thickness of the cover layer above the two-dimensional grating structure. $t_2$ represents the thickness of the grating. $t_{bio}$ represents the thickness of the layer of one or more specific binding substances. In one embodiment, are n2<n1 (see FIG. 1). Layer thicknesses (i.e. cover layer, one or more specific binding substances, or a two-dimensional grating) are selected to achieve resonant wavelength sensitivity to additional molecules on the top surface The grating period is selected to achieve resonance at a desired wavelength.

One embodiment of the invention provides a SWS biosensor. A SWS biosensor comprises a two-dimensional grating, a substrate layer that supports the two-dimensional grating, and one or more specific binding substances immobilized on the surface of the two-dimensional grating opposite of the substrate layer.

A two-dimensional grating can be comprised of a material, including, for example, zinc sulfide, titanium dioxide, tantalum oxide, and silicon nitride. A cross-sectional profile of a two-dimensional grating can comprise any periodically repeating function, for example, a "square-wave." A two-dimensional grating can be comprised of a repeating pattern of shapes selected from the group consisting of lines, squares, circles, ellipses, triangles, trapezoids, sinusoidal waves, ovals, rectangles, and hexagons. A sinusoidal cross-sectional profile is preferable for manufacturing applications that require embossing of a grating shape into a soft material such as plastic. In one embodiment of the invention, the depth of the grating is about 0.01 micron to about 1 micron and the period of the grating is about 0.01 micron to about 1 micron.

Figure 3A:
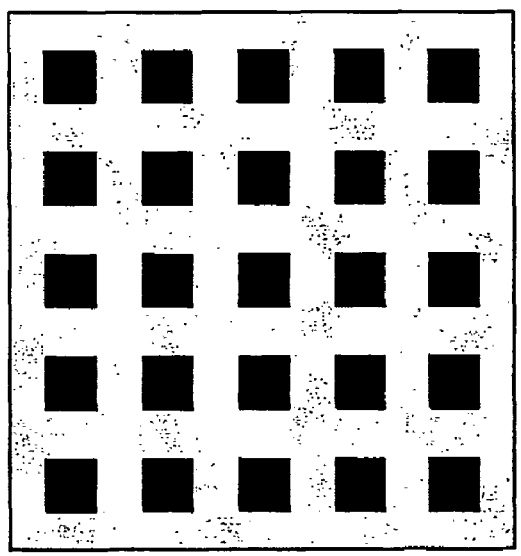
FIGS. 3A-B shows a grating comprising a rectangular grid of squares (FIG. 3A) or holes (FIG. 3B).
Figure 3B:
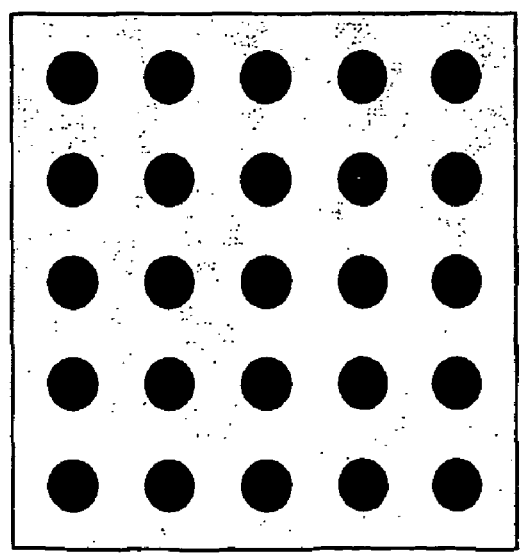

Linear gratings have resonant characteristics where the illuminating light polarization is oriented perpendicular to the grating period. However, a hexagonal grid of holes has better polarization symmetry than a rectangular grid of holes. Therefore, a colorimetric resonant reflection biosensor of the invention can comprise, for example, a hexagonal array of holes (see FIG. 3B) or a grid of parallel lines (see FIG. 3A). A linear grating has the same pitch (i.e. distance between regions of high and low refractive index), period, layer thicknesses, and material properties as the hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

Figure 2:
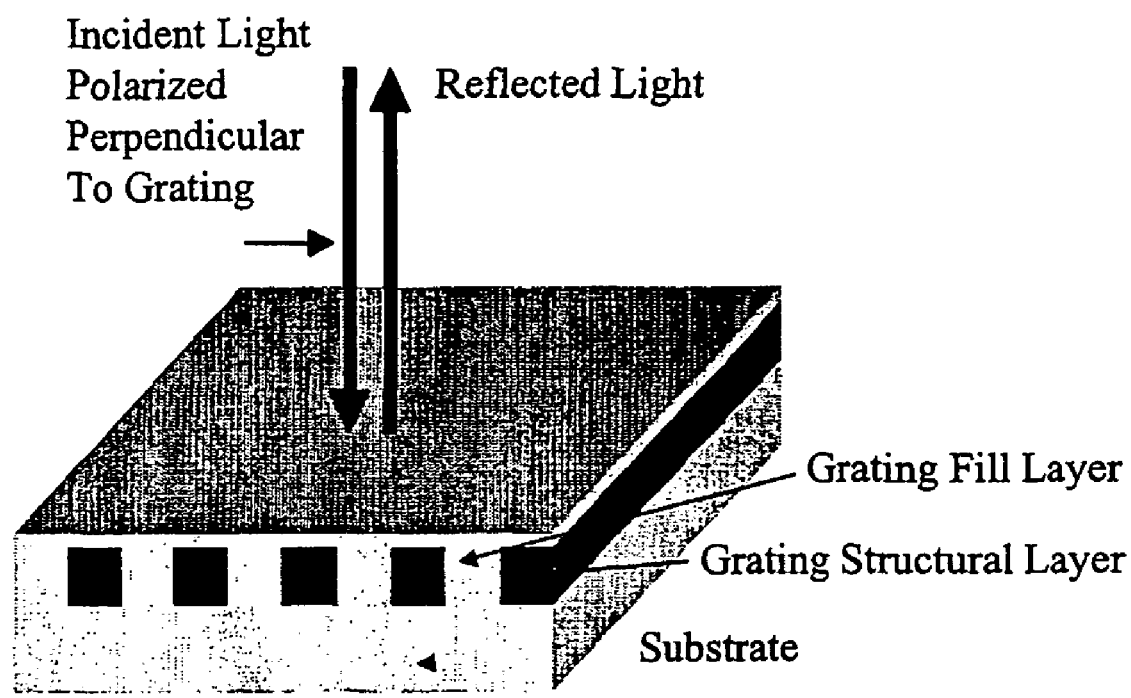
FIG. 2 shows a schematic drawing of a linear grating structure.

While a linear grating can require either a higher intensity illumination source or a longer measurement integration time compared to a hexagonal grating, the fabrication requirements for the linear structure are simpler. A hexagonal grating pattern is produced by holographic exposure of photoresist to three mutually interfering laser beams. The three beams are precisely aligned in order to produce a grating pattern that is symmetrical in three directions. A linear grating pattern requires alignment of only two laser beams to produce a holographic exposure in photoresist, and thus has a reduced alignment requirement. A linear grating pattern can also be produced by, for example, direct writing of photoresist with an electron beam. Also, several commercially available sources exist for producing linear grating "master" templates for embossing a grating structure into plastic. A schematic diagram of a linear grating structure is shown in FIG. 2.

A rectangular grid pattern can be produced in photoresist using an electron beam direct-write exposure system. A single wafer can be illuminated as a linear grating with two sequential exposures with the part rotated 90-degrees between exposures.

A two-dimensional grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor. See FIG. 5.

For manufacture, a stepped structure is etched or embossed into a substrate material such as glass or plastic. See FIG. 5. A uniform thin film of higher refractive index material, such as silicon nitride or zinc sulfide is deposited on this structure. The deposited layer will follow the shape contour of the embossed or etched structure in the substrate, so that the deposited material has a surface relief profile that is identical to the original embossed or etched profile. The structure can be completed by the application of an optional cover layer comprised of a material having a lower refractive index than the higher refractive index material and having a substantially flat upper surface. The covering material can be, for example, glass, epoxy, or plastic.

This structure allows for low cost biosensor manufacturing, because it can be mass produced. A "master" grating can be produced in glass, plastic, or metal using, for example, a three-beam laser holographic patterning process, See e.g., Cowan, The recording and large scale production of crossed holographic grating arrays using multiple beam interferometry, *Proc. Soc. Photo-optical Instum. Eng.* 503:120 (1984). A master grating can be repeatedly used to emboss a plastic substrate. The embossed substrate is subsequently coated with a high refractive index material and optionally, a cover layer.

Figure 4:
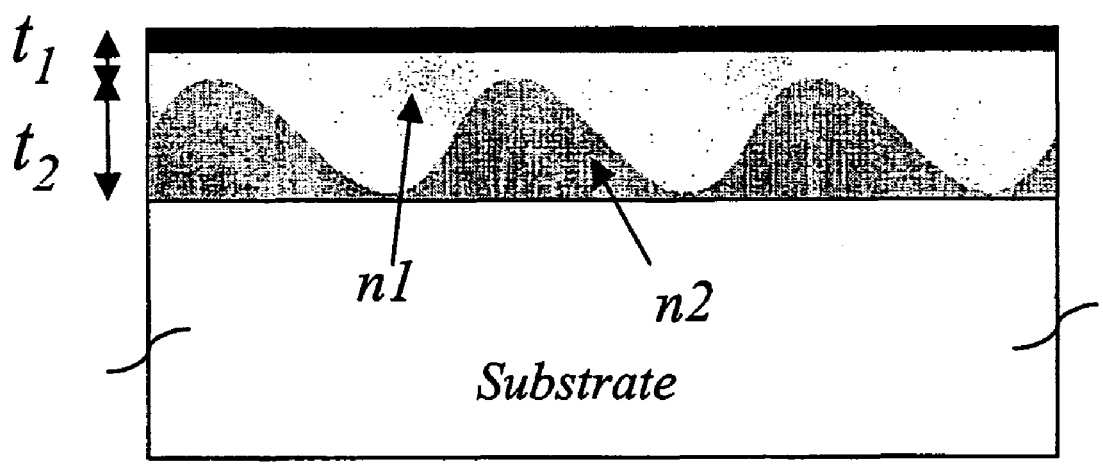
FIG. 4 shows a biosensor cross-section profile utilizing a sinusoidally varying grating profile.

While a stepped structure is simple to manufacture, it is also possible to make a resonant biosensor in which the high refractive index material is not stepped, but which varies with lateral position. FIG. 4 shows a profile in which the high refractive index material of the two-dimensional grating, $n_2$, is sinusoidally varying in height. To produce a resonant reflection at a particular wavelength, the period of the sinusoid is identical to the period of an equivalent stepped structure. The resonant operation of the sinusoidally varying structure and its functionality as a biosensor has been verified using GSOLVER (Grating Solver Development Company, Allen, Tex., USA) computer models.

Figure 5:
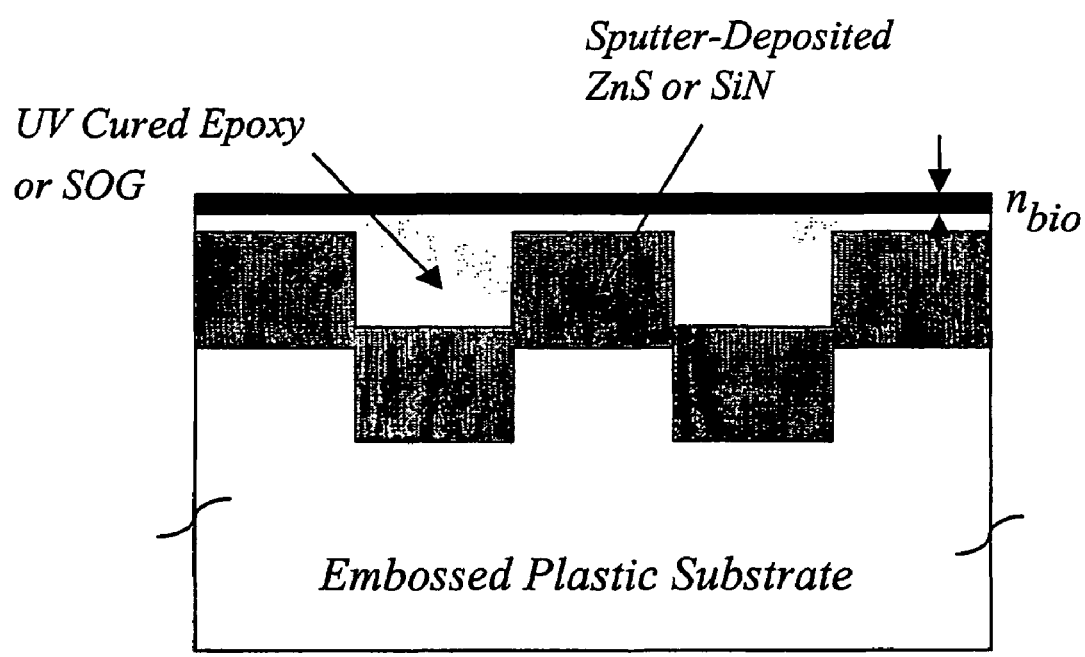
FIG. 5 shows a biosensor cross-section profile in which an embossed substrate is coated with a higher refractive index material such as ZnS or SiN. A cover layer of, for example, epoxy or SOG is layered on top of the higher refractive index material and one or more specific binding substances are immobilized on the cover layer.

Techniques for making two-dimensional gratings are disclosed in Wang, J. Opt. Soc. Am No. 8, Aug. 1990, pp. 1529-44. Biosensors of the invention can be made in, for example, a semiconductor microfabrication facility. Biosensors can also be made on a plastic substrate using continuous embossing and optical coating processes. For this type of manufacturing process, a "master" structure is built in a rigid material such as glass or silicon, and is used to generate "mother" structures in an epoxy or plastic using one of several types of replication procedures. The "mother" structure, in turn, is coated with a thin film of conducive material, and used as a mold to electroplate a thick film of nickel. The nickel "daughter" is released from the plastic "mother" structure. Finally, the nickel "daughter" is bonded to a cylindrical drum, which is used to continuously emboss the surface relief structure into a plastic film. A device structure that uses an embossed plastic substrate is shown in FIG. 5. Following embossing, the plastic structure is overcoated with a thin film of high refractive index material, and optionally coated with a planarizing, cover layer polymer, and cut to appropriate size.

A substrate for a SWS biosensor can comprise, for example, glass, plastic or epoxy. Optionally, a substrate and a two-dimensional grating can comprise a single unit. That is, a two dimensional grating and substrate are formed from the same material, for example, glass, plastic, or epoxy. The surface of a single unit comprising the two-dimensional grating is coated with a material having a high refractive index, for example, zinc sulfide, titanium dioxide, tantalum oxide, and silicon nitride. One or more specific binding substances can be immobilized on the surface of the material having a high refractive index or on an optional cover layer.

A biosensor of the invention can further comprise a cover layer on the surface of a two-dimensional grating opposite of a substrate layer. Where a cover layer is present, the one or more specific binding substances are immobilized on the surface of the cover layer opposite of the two-dimensional grating. Preferably, a cover layer comprises a material that has a lower refractive index than a material that comprises the two-dimensional grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over a two-dimensional grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces a two-dimensional grating exposed to the specific binding substances, rather than only on an upper surface.

In general, a biosensor of the invention will be illuminated with white light that will contain light of every polarization angle. The orientation of the polarization angle with respect to repeating features in a biosensor grating will determine the resonance wavelength. For example, a "linear grating" biosensor structure consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor structure can generally be designed to optimize the properties of only one polarization (the s-polarization), and the non-optimize polarization is easily removed by a polarizing filter.

Figure 49:
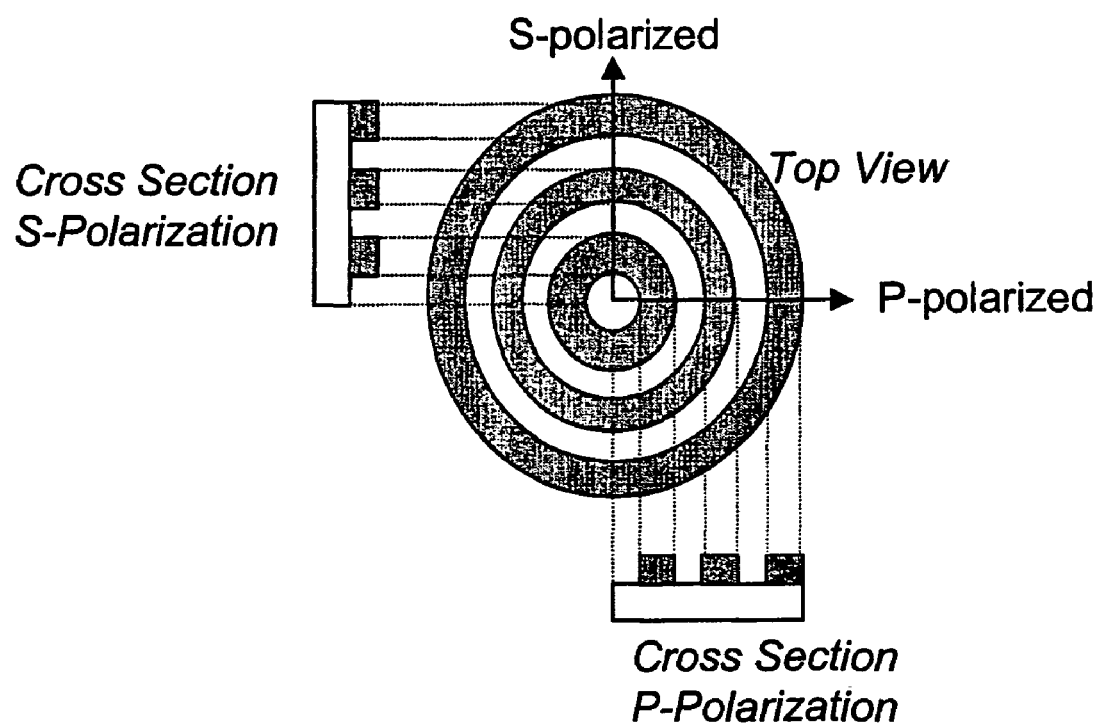
FIG. 49 shows a resonant reflection or transmission filter structure consisting of a set of concentric rings.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtiter plate well. Each separate microarray spot or microtiter plate well has a separate concentric ring pattern centered within it e.g., FIG. 49. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

Figure 50:
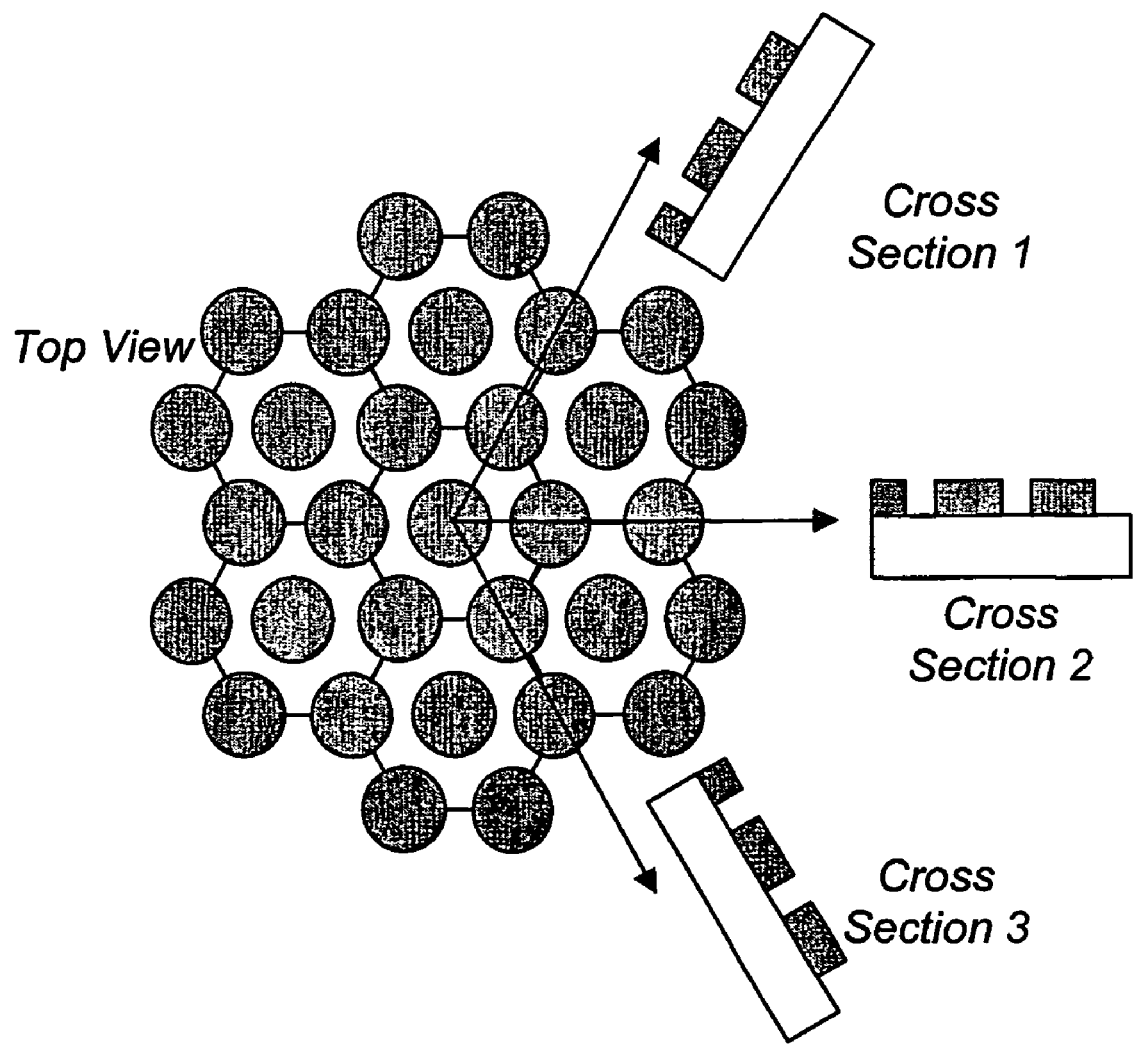
FIG. 50 shows a resonant reflective or transmission filter structure comprising a hexagonal grid of holes (or a hexagonal grid of posts) that closely approximates the concentric circle structure of FIG. 49 without requiring the illumination beam to be centered upon any particular location of the grid.

In another embodiment, an array of holes or posts are arranged to closely approximate the concentric circle structure described above without requiring the illumination beam to be centered upon any particular location of the grid. See e.g. FIG. 50. Such an array pattern is automatically generated by the optical interference of three laser beams incident on a surface from three directions at equal angles. In this pattern, the holes (or posts) are centered upon the corners of an array of closely packed hexagons as shown in FIG. 50. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

The invention provides a resonant reflection structures and transmission filter structures comprising concentric circle gratings and hexagonal grids of holes or posts. For a resonant reflection structure, light output is measured on the same side of the structure as the illuminating light beam. For a transmission filter structure, light output is measured on the opposite side of the structure as the illuminating beam. The reflected and transmitted signals are complementary. That is, if a wavelength is strongly reflected, it is weakly transmitted. Assuming no energy is absorbed in the structure itself, the reflected+transmitted energy at any given wavelength is constant. The resonant reflection structure and transmission filters are designed to give a highly efficient reflection at a specified wavelength. Thus, a reflection filter will "pass" a narrow band of wavelengths, while a transmission filter will "cut" a narrow band of wavelengths from incident light.

A resonant reflection structure or a transmission filter structure can comprise a two-dimensional grating arranged in a pattern of concentric circles. A resonant reflection structure or transmission filter structure can also comprise a hexagonal grid of holes or posts. When these structure are illuminated with an illuminating light beam, a reflected radiation spectrum is produced that is independent of an illumination polarization angle of the illuminating light beam. When these structures are illuminated a resonant grating effect is produced on the reflected radiation spectrum, wherein the depth and period of the two-dimensional grating or hexagonal grid of holes or posts are less than the wavelength of the resonant grating effect. These structures reflect a narrow band of light when the structure is illuminated with a broadband of light.

Resonant reflection structures and transmission filter structures of the invention can be used as biosensors. For example, one or more specific binding substances can be immobilized on the hexagonal grid of holes or posts or on the two-dimensional grating arranged in concentric circles.

In one embodiment of the invention, a reference resonant signal is provided for more accurate measurement of peak resonant wavelength shifts. The reference resonant signal can cancel out environmental effects, including, for example, temperature. A reference signal can be provided using a resonant reflection superstructure that produces two separate resonant wavelengths. A transparent resonant reflection superstructure can contain two sub-structures. A first sub-structure comprises a first two-dimensional grating with a top and a bottom surface. The top surface of a two-dimensional grating comprises the grating surface. The first two-dimensional grating can comprise one or more specific binding substances immobilized on its top surface. The top surface of the first two-dimensional grating is in contact with a test sample. An optional substrate layer can be present to support the bottom surface of the first two-dimensional grating. The substrate layer comprises a top and bottom surface. The top surface of the substrate is in contact with, and supports the bottom surface of the first two-dimensional grating.

A second sub-structure comprises a second two-dimensional grating with a top surface and a bottom surface. The second two-dimensional grating is not in contact with a test sample. The second two-dimensional grating can be fabricated onto the bottom surface of the substrate that supports the first two-dimensional grating. Where the second two-dimensional grating is fabricated on the substrate that supports the first two-dimensional grating, the bottom surface of the second two-dimensional grating can be fabricated onto the bottom surface of the substrate. Therefore, the top surface of the second two-dimensional grating will face the opposite direction of the top surface of the first two-dimensional grating.

The top surface of the second two-dimensional grating can also be attached directly to the bottom surface of the first sub-structure. In this embodiment the top surface of the second two-dimensional grating will face the same direction as the top surface of the first two-dimensional grating. A substrate can support the bottom surface of the second two-dimensional grating in this embodiment.

Because the second sub-structure is not in physical contact with the test sample, its peak resonant wavelength is not subject to changes in the optical density of the test media, or deposition of specific binding substances or binding partners on the surface of the first two-dimensional grating. Therefore, such a superstructure produces two resonant signals. Because the location of the peak resonant wavelength in the second sub-structure is fixed, the difference in peak resonant wavelength between the two sub-structures provides a relative means for determining the amount of specific binding substances or binding partners or both deposited on the top surface of the first substructure that is exposed to the test sample.

A biosensor superstructure can be illuminated from its top surface or from its bottom surface, or from both surfaces. The peak resonance reflection wavelength of the first substructure is dependent on the optical density of material in contact with the superstructure surface, while the peak resonance reflection wavelength of the second substructure is independent of the optical density of material in contact with the superstructure surface.

In one embodiment of the invention, a biosensor is illuminated from the bottom surface of the biosensor. Approximately 50% of the incident light is reflected from the bottom surface of biosensor without reaching the active (top) surface of the biosensor. A thin film or physical structure can be included in a biosensor composition that is capable of maximizing the amount of light that is transmitted to the upper surface of the biosensor while minimizing the reflected energy at the resonant wavelength. The anti-reflection thin film or physical structure of the bottom surface of the biosensor can comprise, for example, a single dielectric thin film, a stack of multiple dielectric thin films, or a "motheye" structure that is embossed into the bottom biosensor surface. An example of a motheye structure is disclosed in Hobbs, et al. "Automated interference lithography system for generation of sub-micron feature size patterns," *Proc.* 1999 *Micromachine Technology for Diffracting and Holographic Optics, Society of Photo-Optical Instrumentation Engineers*, p. 124-135, (1999).

In one embodiment of the invention, an optical device is provided. An optical device comprises a structure similar to any biosensor of the invention; however, an optical device does not comprise one of more binding substances immobilized on the two-dimensional grating. An optical device can be used as a narrow band optical filter.

In one embodiment of the invention, an interaction of a first molecule with a second test molecule can be detected. A SWS biosensor as described above is used; however, there are no specific binding substances immobilized on its surface. Therefore, the biosensor comprises a two-dimensional grating, a substrate layer that supports the two-dimensional grating, and optionally, a cover layer. As described above, when the biosensor is illuminated a resonant grating effect is produced on the reflected radiation spectrum, and the depth and period of the two-dimensional grating are less than the wavelength of the resonant grating effect.

To detect an interaction of a first molecule with a second test molecule, a mixture of the first and second molecules is applied to a distinct location on a biosensor. A distinct location can be one spot or well on a biosensor or can be a large area on a biosensor. A mixture of the first molecule with a third control molecule is also applied to a distinct location on a biosensor. The biosensor can be the same biosensor as described above, or can be a second biosensor. If the biosensor is the same biosensor, a second distinct location can be used for the mixture of the first molecule and the third control molecule. Alternatively, the same distinct biosensor location can be used after the first and second molecules are washed from the biosensor. The third control molecule does not interact with the first molecule and is about the same size as the first molecule. A shift in the reflected wavelength of light from the distinct locations of the biosensor or biosensors is measured. If the shift in the reflected wavelength of light from the distinct location having the first molecule and the second test molecule is greater than the shift in the reflected wavelength from the distinct location having the first molecule and the third control molecule, then the first molecule and the second test molecule interact. Interaction can be, for example, hybridization of nucleic acid molecules, specific binding of an antibody or antibody fragment to an antigen, and binding of polypeptides. A first molecule, second test molecule, or third control molecule can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, and bacteria.

Specific Binding Substances and Binding Partners

One or more specific binding substances are immobilized on the two-dimensional grating or cover layer, if present, by for example, physical adsorption or by chemical binding. A specific binding substance can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatitc fluid.

Preferably, one or more specific binding substances are arranged in a microarray of distinct locations on a biosensor. A microarray of specific binding substances comprises one or more specific binding substances on a surface of a biosensor of the invention such that a surface contains many distinct locations, each with a different specific binding substance or with a different amount of a specific binding substance. For example, an array can comprise 1, 10, 100, 1,000, 10,000, or 100,000 distinct locations. Such a biosensor surface is called a microarray because one or more specific binding substances are typically laid out in a regular grid pattern in x-y coordinates. However, a microarray of the invention can comprise one or more specific binding substance laid out in any type of regular or irregular pattern. For example, distinct locations can define a microarray of spots of one or more specific binding substances. A microarray spot can be about 50 to about 500 microns in diameter. A microarray spot can also be about 150 to about 200 microns in diameter. One or more specific binding substances can be bound to their specific binding partners.

A microarray on a biosensor of the invention can be created by placing microdroplets of one or more specific binding substances onto, for example, an x-y grid of locations on a two-dimensional grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, and biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatitc fluid.

One example of a microarray of the invention is a nucleic acid microarray, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a biosensor of the invention, specific binding substance densities of 10,000 specific binding substances/in$^2$ can be obtained. By focusing an illumination beam to interrogate a single microarray location, a biosensor can be used as a label-free microarray readout system.

Immobilization or One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers). Chemical binding can generate stronger attachment of specific binding substances on a biosensor surface and provide defined orientation and conformation of the surface-bound molecules.

Several examples of chemical binding of specific binding substances to a biosensor of the invention appear in Example 8, below. Other types of chemical binding include, for example, amine activation, aldehyde activation, and nickel activation. These surfaces can be used to attach several different types of chemical linkers to a biosensor surface, as shown in FIG. 6. While an amine surface can be used to attach several types of linker molecules, an aldehyde surface can be used to bind proteins directly, without an additional linker. A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Immobilization of specific binding substances to plastic, epoxy, or high refractive index material can be performed essentially as described for immobilization to glass. However, the acid wash step can be eliminated where such a treatment would damage the material to which the specific binding substances are immobilized.

For the detection of binding partners at concentrations less than about ~0.1 ng/ml, it is preferable to amplify and transduce binding partners bound to a biosensor into an additional layer on the biosensor surface. The increased mass deposited on the biosensor can be easily detected as a consequence of increased optical path length. By incorporating greater mass onto a biosensor surface, the optical density of binding partners on the surface is also increased, thus rendering a greater resonant wavelength shift than would occur without the added mass. The addition of mass can be accomplished, for example, enzymatically, through a "sandwich" assay, or by direct application of mass to the biosensor surface in the form of appropriately conjugated beads or polymers of various size and composition. This principle has been exploited for other types of optical biosensors to demonstrate sensitivity increases over 1500x beyond sensitivity limits achieved without mass amplification. See, e.g., Jenison et al., "Interference-based detection of nucleic acid targets on optically coated silicon," *Nature Biotechnology*, 19: 62-65, 2001.

Figure 7A:
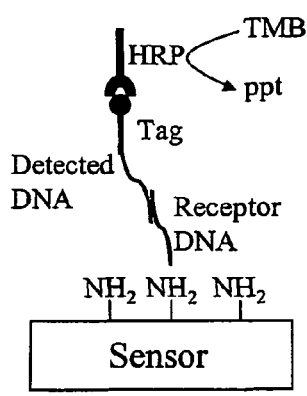
FIGS. 7A-C shows methods that can be used to amplify the mass of a binding partner such as detected DNA or detected protein on the surface of a biosensor.

As an example, FIG. 7A shows that an $NH_2$-activated biosensor surface can have a specific binding substance comprising a single-strand DNA capture probe immobilized on the surface. The capture probe interacts selectively with its complementary target binding partner. The binding partner, in turn, can be designed to include a sequence or tag that will bind a "detector" molecule. As shown in FIG. 7A, a detector molecule can contain, for example, a linker to horseradish peroxidase (HRP) that, when exposed to the correct enzyme, will selectively deposit additional material on the biosensor only where the detector molecule is present. Such a procedure can add, for example, 300 angstroms of detectable biomaterial to the biosensor within a few minutes.

Figure 7B:
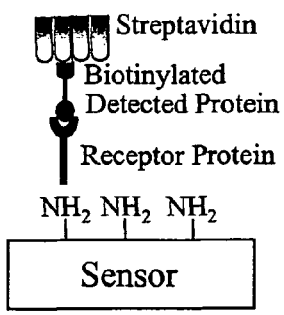

A "sandwich" approach can also be used to enhance detection sensitivity. In this approach, a large molecular weight molecule can be used to amplify the presence of a low molecular weight molecule. For example, a binding partner with a molecular weight of, for example, about 0.1 kDa to about 20 kDa, can be tagged with, for example, succinimidyl-6-[a-methyl-a-(2-pyridyl-dithio) toluamido] hexanoate (SMPI), or dimethylpimelimidate (DMP), histidine, or a biotin molecule, as shown in FIG. 7B. Where the tag is biotin, the biotin molecule will binds strongly with streptavidin, which has a molecular weight of 60 kDa. Because the biotin/streptavidin interaction is highly specific, the streptavidin amplifies the signal that would be produced only by the small binding partner by a factor of 60.

Figure 7C:
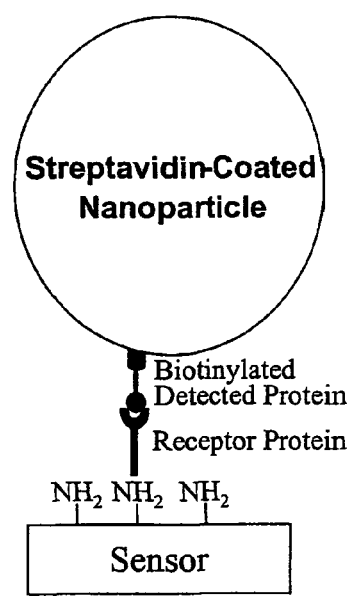

Detection sensitivity can be further enhanced through the use of chemically derivatized small particles. "Nanoparticles" made of colloidal gold, various plastics, or glass with diameters of about 3-300 nm can be coated with molecular species that will enable them to covalently bind selectively to a binding partner. For example, as shown in FIG. 7C, nanoparticles that are covalently coated with streptavidin can be used to enhance the visibility of biotin-tagged binding partners on the biosensor surface. While a streptavidin molecule itself has a molecular weight of 60 kDa, the derivatized bead can have a molecular weight of any size, including, for example, 60 KDa. Binding of a large bead will result in a large change in the optical density upon the biosensor surface, and an easily measurable signal. This method can result in an approximately 1000x enhancement in sensitivity resolution.

Surface-Relief Volume Diffractive Biosensors

Another embodiment of the invention is a biosensor that comprises volume surface-relief volume diffractive structures (a SRVD biosensor). SRVD biosensors have a surface that reflect predominantly at a particular narrow band of optical wavelengths when illuminated with a broad band of optical wavelengths. Where specific binding substances and/or binding partners are immobilized on a SRVD biosensor, the reflected wavelength of light is shifted. One-dimensional surfaces, such as thin film interference filters and Bragg reflectors, can select a narrow range of reflected or transmitted wavelengths from a broadband excitation source, however, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface.

A SRVD biosensor comprises a sheet material having a first and second surface. The first surface of the sheet material defines relief volume diffraction structures. A sheet material can be comprised of, for example, plastic, glass, semiconductor wafer, or metal film.

A relief volume diffractive structure can be, for example, a two-dimensional grating, as described above, or a three-dimensional surface-relief volume diffractive grating. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps. The reflected or diffracted color can be controlled by the deposition of a dielectric layer so that a new wavelength is selected, depending on the index of refraction of the coating.

A stepped-phase structure can be produced first in photoresist by coherently exposing a thin photoresist film to three laser beams, as described previously. See e.g., Cowen, "The recording and large scale replication of crossed holographic grating arrays using multiple beam interferometry," in *International Conference on the Application, Theory, and Fabrication of Periodic Structures, Diffraction Gratings, and Moire Phenomena II*, Lerner, ed., Proc. Soc. Photo-Opt Instrum. Eng., 503, 120-129, 1984; Cowen, "Holographic honeycomb microlens," *Opt. Eng.* 24, 796-802 (1985); Cowen & Slafer, "The recording and replication of holographic micropatterns for the ordering of photographic emulsion grains in film systems," *J. Imaging Sci.* 31, 100-107, 1987. The nonlinear etching characteristics of photoresist are used to develop the exposed film to create a three-dimensional relief pattern. The photoresist structure is then replicated using standard embossing procedures. For example, a thin silver film is deposited over the photoresist structure to form a conducting layer upon which a thick film of nickel can be electroplated. The nickel "master" plate is then used to emboss directly into a plastic film, such as vinyl, that has been softened by heating or solvent.

The theory describing the design and fabrication of three-dimensional phase-quantized terraced surface relief pattern that resemble stepped pyramids is described: Cowen, "Aztec surface-relief volume diffractive structure," *J. Opt. Soc. Am. A*, 7:1529 (1990).

Figure 8:
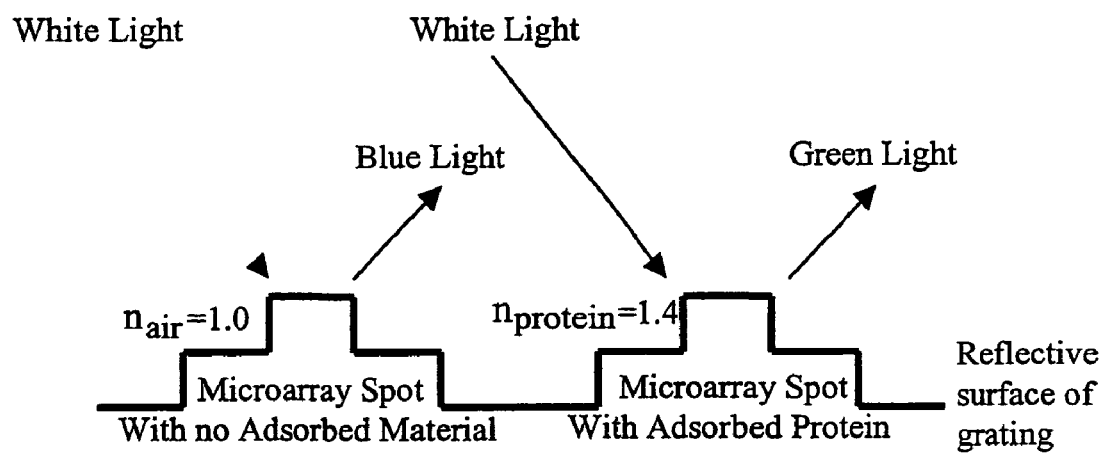
FIG. 8 shows a graphic representation of how adsorbed material, such as a protein monolayer, will increase the reflected wavelength of on a SRVD biosensor.

An example of a three-dimensional phase-quantized terraced surface relief pattern is a pattern that resembles a stepped pyramid. Each inverted pyramid is approximately 1 micron in diameter, preferably, each inverted pyramid can be about 0.5 to about 5 microns diameter, including for example, about 1 micron. The pyramid structures can be close-packed so that a typical microarray spot with a diameter of 150-200 microns can incorporate several hundred stepped pyramid structures. The relief volume diffraction structures have a period of about 0.1 to about 1 micron and a depth of about 0.1 to about 1 micron. FIG. 8 demonstrates how individual microarray locations (with an entire microarray spot incorporating hundreds of pyramids now represented by a single pyramid for one microarray spot) can be optically queried to determine if specific binding substances or binding partners are adsorbed onto the surface. When the structure is illuminated with white light, structures without significant bound material will reflect wavelengths determined by the step height of the structure. When higher refractive index material, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a sheet material of a SRVD biosensor. A reflective material can be, for example silver, aluminum, or gold.

Figure 9:
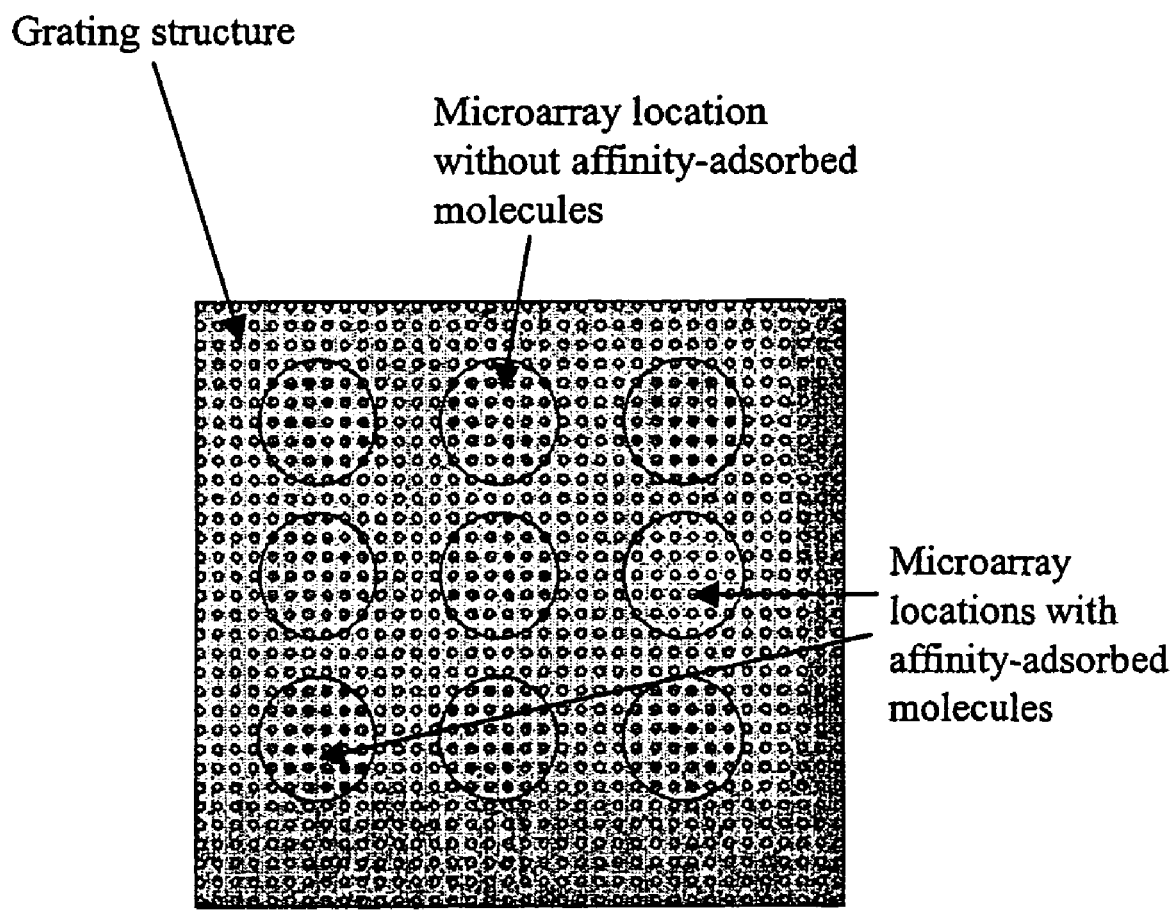
FIG. 9 shows an example of a biosensor used as a microarray.

One or more specific binding substances, as described above, are immobilized on the reflective material of a SRVD biosensor. One or more specific binding substances can be arranged in microarray of distinct locations, as described above, on the reflective material. FIG. 9 provides an example of a 9-element microarray biosensor. Many individual grating structures, represented by small circles, lie within each microarray spot. The microarray spots, represented by the larger circles, will reflect white light in air at a wavelength that is determined by the refractive index of material on their surface. Microarray locations with additional adsorbed material will have reflected wavelengths that are shifted toward longer wavelengths, represented by the larger circles.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots and reading the reflected spectrum, or in parallel by, for example, projecting the reflected image of the microarray onto a high resolution color CCD camera.

A SRVD biosensor can be manufactured by, for example, producing a metal master plate, and stamping a relief volume diffractive structure into, for example, a plastic material like vinyl. After stamping, the surface is made reflective by blanket deposition of, for example, a thin metal film such as gold, silver, or aluminum. Compared to MEMS-based biosensors that rely upon photolithography, etching, and wafer bonding procedures, the manufacture of a SRVD biosensor is very inexpensive.

Liquid-Containing Vessels

Figures 10A, 10B:
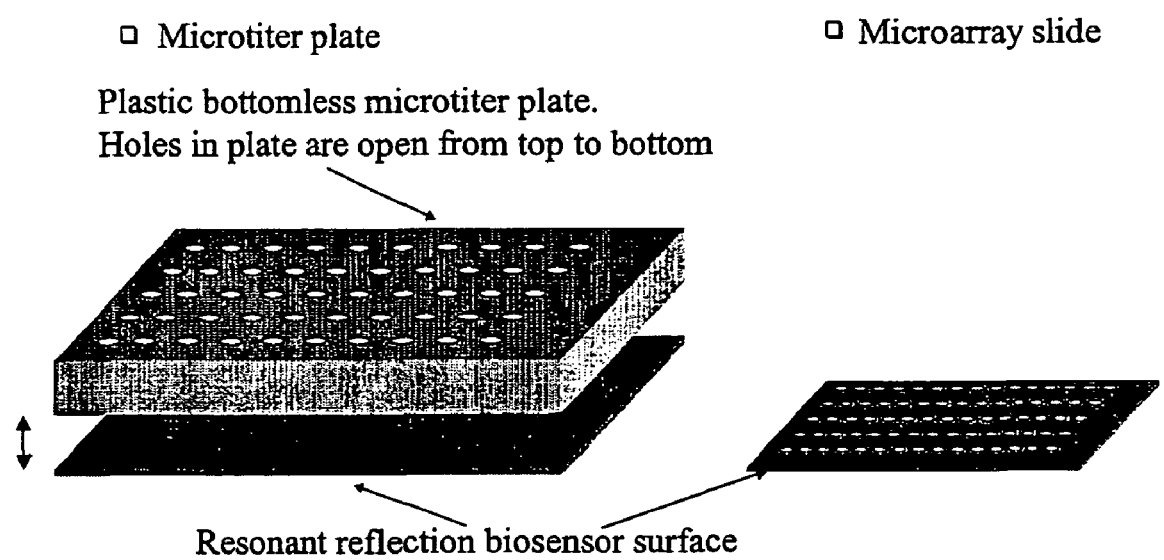
FIGS. 10A-B shows two biosensor formats that can incorporate a calorimetric resonant reflectance biosensor.

A SWS or SRVD biosensor of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a SWS or SRVD biosensor that is incorporated into any type of microtiter plate. For example, a SWS biosensor or SRVD biosensor can be incorporated into the bottom surface of a microtiter plate by assembling the walls of the reaction vessels over the resonant reflection surface, as shown in FIG. 10, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. See, e g., FIG. 10. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Holding Fixtures

Figure 11:
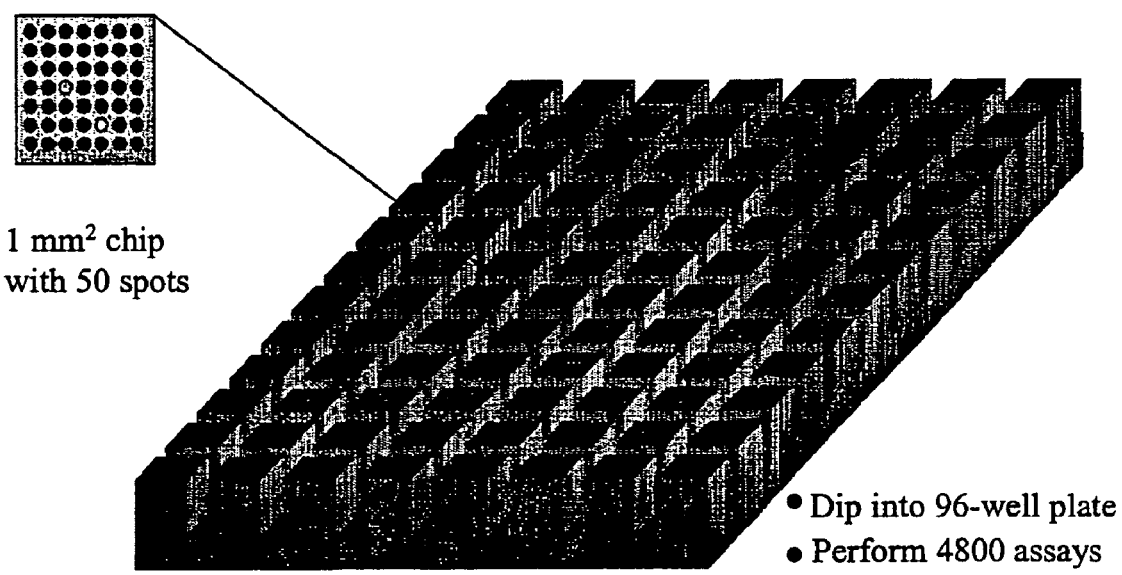
FIG. 11 shows an array of arrays concept for using a biosensor platform to perform assays with higher density and throughput.

Any number of biosensors that are, for example, about 1 $mm^2$ to about 5 $mm^2$, and preferably less than about 3×3 $mm^2$ can be arranged onto a holding fixture that can simultaneously dip the biosensors into separate liquid-containing vessels, such as wells of a microtiter plate, for example, a 96-, 384-, or 1536-well microtiter plate. See e.g., FIG. 11. Each of the biosensors can contain multiple distinct locations. A holding fixture has one or more biosensors attached to the holding fixture so that each individual biosensor can be lowered into a separate liquid-containing vessel. A holding fixture can comprise plastic, epoxy or metal. For example, 50, 96, 384, or 1,000, or 1,536 biosensors can be arranged on a holding fixture, where each biosensor has 25, 100, 500, or 1,000 distinct locations. As an example, where 96 biosenors are attached to a holding fixture and each biosensor comprises 100 distinct locations, 9600 biochemical assays can be performed simultaneously.

Methods of Using SWS and SRVD Biosensors

SWS and SRVD biosensors of the invention can be used to study one or a number of specific binding substance/binding partner interactions in parallel. Binding of one or more specific binding substances to their respective binding partners can be detected, without the use of labels, by applying one or more binding partners to a SWS or SRVD biosensor that have one or more specific binding substances immobilized on their surfaces. A SWS biosensor is illuminated with light and a maxima in reflected wavelength, or a minima in transmitted wavelength of light is detected from the biosensor. If one or more specific binding substances have bound to their respective binding partners, then the reflected wavelength of light is shifted as compared to a situation where one or more specific binding substances have not bound to their respective binding partners. Where a SWS biosensor is coated with an array of distinct locations containing the one or more specific binding substances, then a maxima in reflected wavelength or minima in transmitted wavelength of light is detected from each distinct location of the biosensor.

A SRVD biosensor is illuminated with light after binding partners have been added and the reflected wavelength of light is detected from the biosensor. Where one or more specific binding substances have bound to their respective binding partners, the reflected wavelength of light is shifted.

In one embodiment of the invention, a variety of specific binding substances, for example, antibodies, can be immobilized in an array format onto a biosensor of the invention. The biosensor is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent-label is not required.

The Activity of an enzyme can be detected by applying one or more enzymes to a SWS or SRVD biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity, the reflected wavelength of light is shifted.

Additionally, a test sample, for example, cell lysates containing binding partners can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

For the above applications, and in particular proteomics applications, the ability to selectively bind material, such as binding partners from a test sample onto a biosensor of the invention, followed by the ability to selectively remove bound material from a distinct location of the biosensor for further analysis is advantageous. Biosensors of the invention are also capable of detecting and quantifying the amount of a binding partner from a sample that is bound to a biosensor array distinct location by measuring the shift in reflected wavelength of light. For example, the wavelength shift at one distinct biosensor location can be compared to positive and negative controls at other distinct biosensor locations to determine the amount of a binding partner that is bound to a biosensor array distinct location.

SWS and Electrically Conducting Material

An optional biosensor structure can further enable a biosensor array to selectively attract or repel binding partners from individual distinct locations on a biosensor. As is well known in the art, an electromotive force can be applied to biological molecules such as nucleic acids and amino acids subjecting them to an electric field. Because these molecules are electronegative, they are attracted to a positively charged electrode and repelled by a negatively charged electrode.

Figure 48:
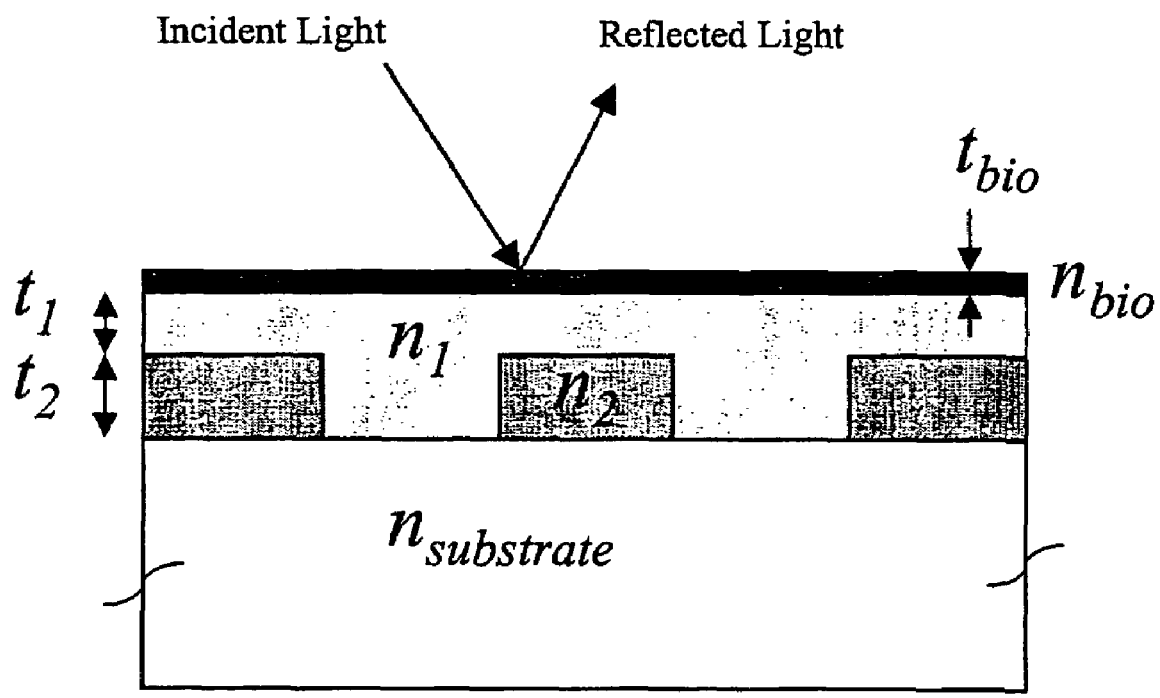
FIG. 48 shows a resonant optical biosensor incorporating an electrically conducting material.

A grating structure of a resonant optical biosensor can be built using an electrically conducting material rather than an electrically insulating material. An electric field can be applied near the biosensor surface. Where a grating operates as both a resonant reflector biosensor and as an electrode, the grating comprises a material that is both optically transparent near the resonant wavelength, and has low resistivity. In one embodiment of the invention, the material is indium tin oxide, $InSn_xO_{1-x}$ (ITO). ITO is commonly used to produce transparent electrodes for flat panel optical displays, and is therefore readily available at low cost on large glass sheets. The refractive index of ITO can be adjusted by controlling x, the fraction of Sn that is present in the material. Because the liquid test sample solution will have mobile ions (and will therefore be an electrical conductor) it is necessary for the ITO electrodes to be coated with an insulating material. For the resonant optical biosensor, a grating layer is coated with a layer with lower refractive index material. Materials such as cured photoresist (n=1.65), cured optical epoxy (n=1.5), and glass (n=1.4-1.5) are strong electrical insulators that also have a refractive index that is lower than ITO (n=2.0-2.65). A cross-sectional diagram of a biosensor that incorporates an ITO grating is shown in FIG. 48. $n_1$ represents the refractive index of an electrical insulator. $n_2$ represents the refractive index of a two-dimensional grating. $t_1$ represents the thickness of the electrical insulator. $t_2$ represents the thickness of the two-dimensional grating. $n_{bio}$ represents the refractive index of one or more specific binding substances and $t_{BIO}$ represents the thickness of the one or more specific binding substances.

A grating can be a continuous sheet of ITO that contains an array of regularly spaced holes. The holes are filled in with an electrically insulating material, such as cured photoresist. The electrically insulating layer overcoats the ITO grating so that the upper surface of the structure is completely covered with electrical insulator, and so that the upper surface is substantially flat. When the biosensor is illuminated with light a resonant grating effect is produced on the reflected radiation spectrum. The depth and the period of the grating are less than the wavelength of the resonant grating effect.

Figure 12:
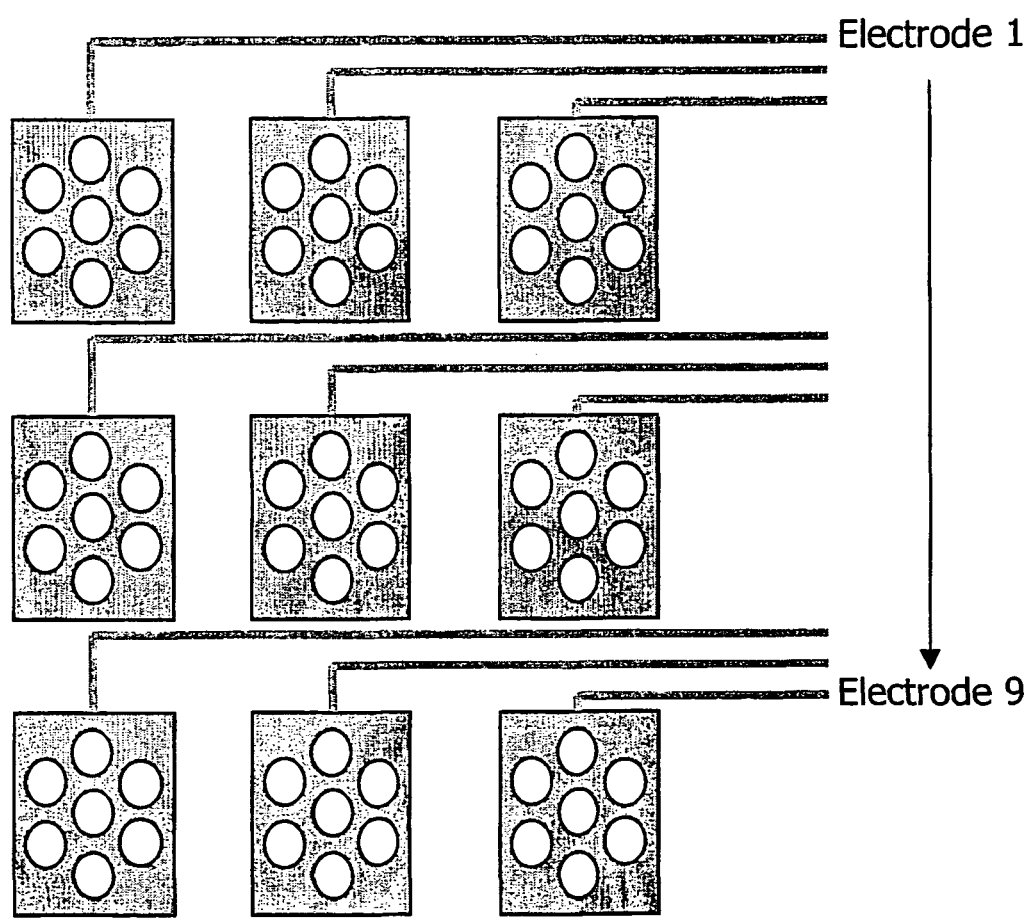
FIG. 12 shows a diagram of an array of biosensor electrodes. A single electrode can comprise a region that contains many grating periods and several separate grating regions can occur on the same substrate surface.
Figure 13:
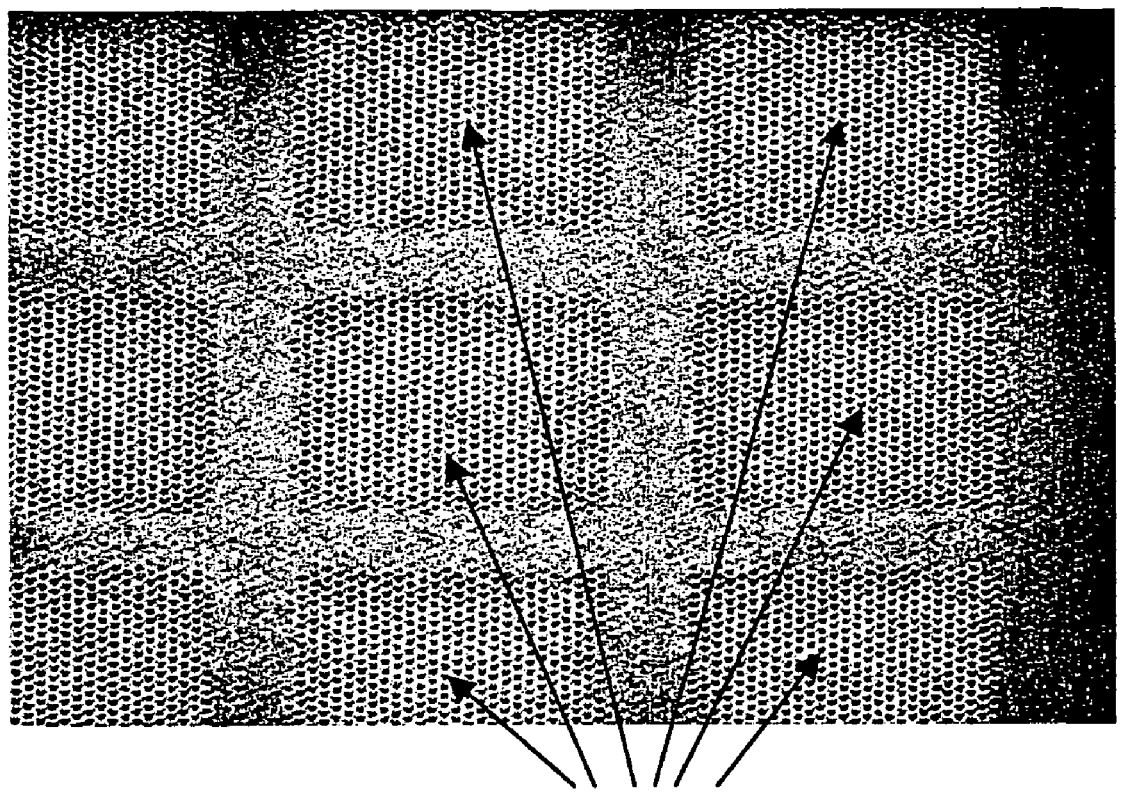
FIG. 13 shows a SEM photograph showing the separate grating regions of an array of biosensor electrodes.
Figure 14:
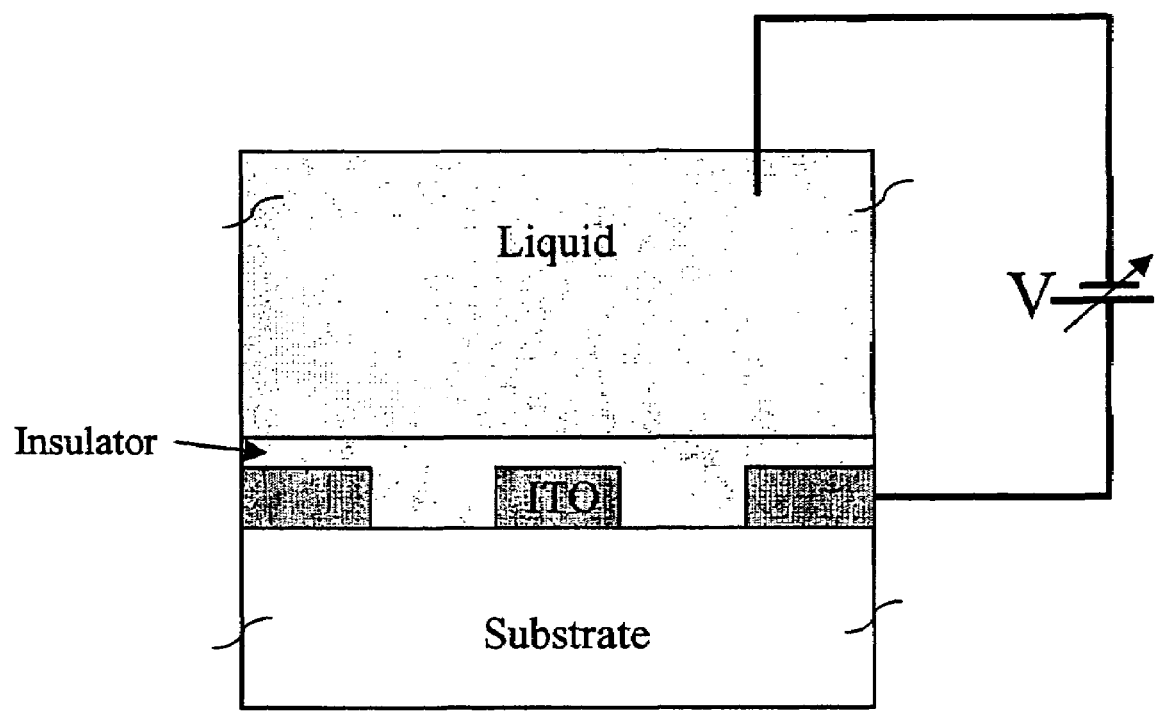
FIG. 14 shows a biosensor upper surface immersed in a liquid sample. An electrical potential can be applied to the biosensor that is capable of attracting or repelling a biomolecule near the electrode surface.
Figure 15:
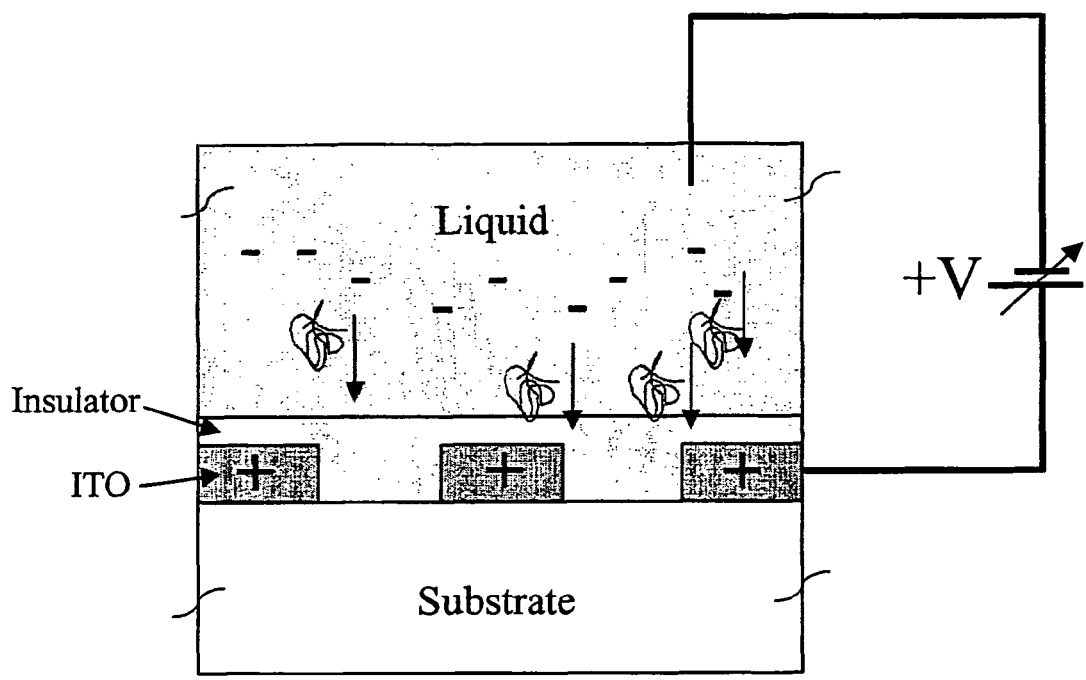
FIG. 15 shows a biosensor upper surface immersed in a liquid sample. A positive voltage is applied to an electrode and the electronegative biomolecules are attracted to the biosensor surface.
Figure 16:
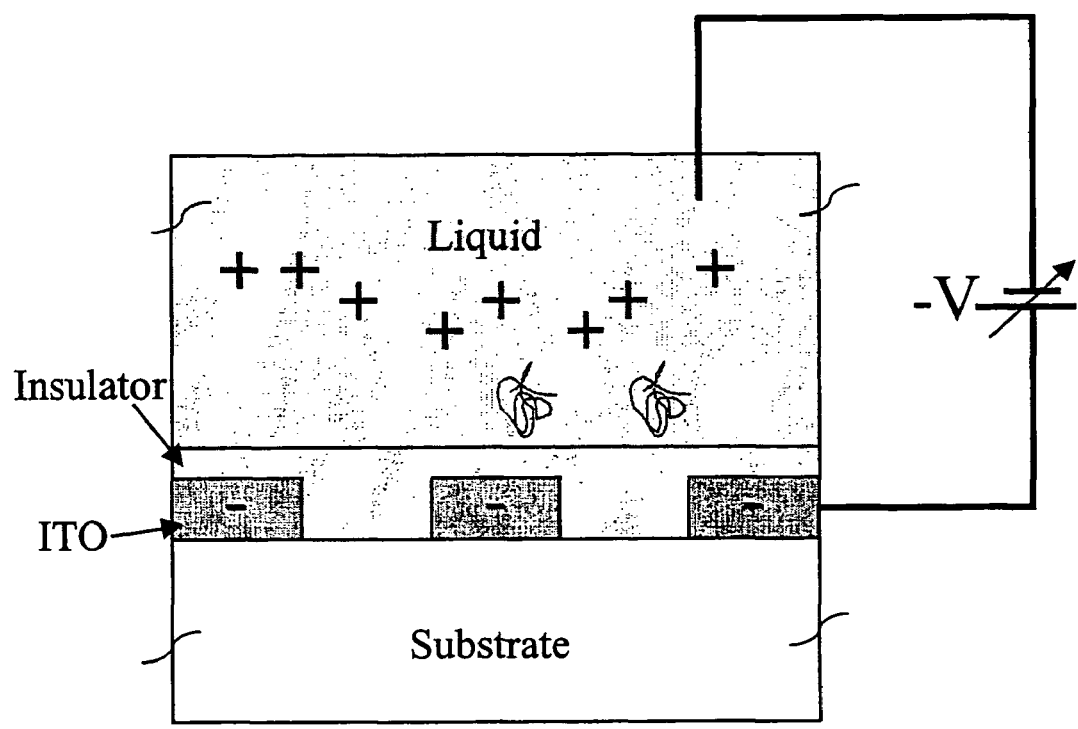
FIG. 16 shows a biosensor upper surface immersed in a liquid sample. A negative voltage is applied to an electrode and the electronegative biomolecules are repelled from the biosensor surface using a negative electrode voltage.

As shown in FIG. 12 and FIG. 13, a single electrode can comprise a region that contains many grating periods. Building two or more separate grating regions on the same substrate surface creates an array of biosensor electrodes. Electrical contact to each biosensor electrode is provided using an electrically conducting trace that is built from the same material as the conductor within the biosensor electrode. The conducting trace is connected to a voltage source that can apply an electrical potential to the electrode. To apply an electrical potential to the biosensor that is capable of attracting or repelling a molecule near the electrode surface, a biosensor upper surface can be immersed in a liquid sample as shown in FIG. 14. A "common" electrode can be placed within the sample liquid, and a voltage can be applied between one selected biosensor electrode region and the common electrode. In this way, one, several, or all electrodes can be activated or inactivated at a given time. FIG. 15 illustrates the attraction of electronegative molecules to the biosensor surface when a positive voltage is applied to the electrode, while FIG. 16 illustrates the application of a repelling force such as a reversed electrical charge to electronegative molecules using a negative electrode voltage.

Detection Systems

A detection system can comprise a biosensor of the invention, a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor of the invention can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor Computer simulation can be used to determine the expected dependence between a peak resonance wavelength and an angle of incident illumination. A biosensor structure as shown in FIG. 1 can be for purposes of demonstration. The substrate chosen was glass ($n_{substrate}$=1.50). The grating is a two-dimensional pattern of silicon nitride squares ($t_2$=180 nm, $n_2$=2.01 (n=refractive index), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

Figure 19:
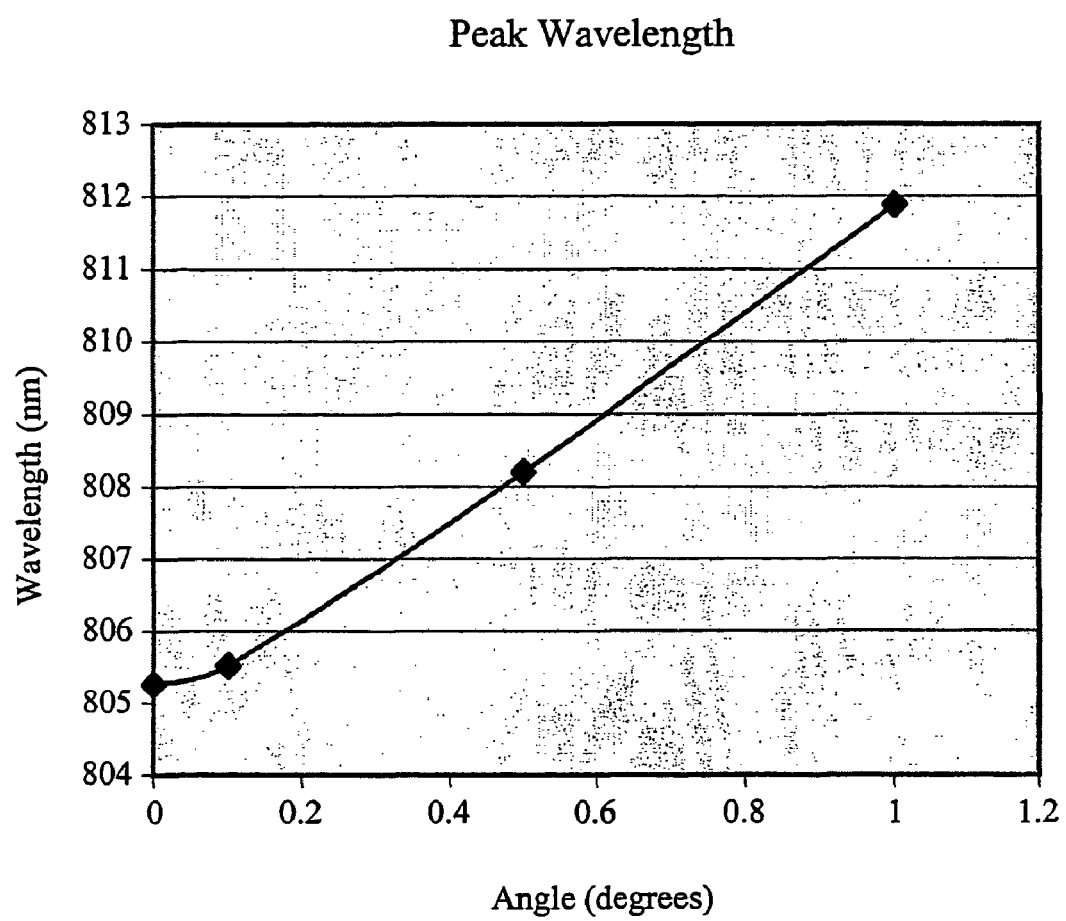
FIG. 19 shows resonance wavelength of a biosensor as a function of incident angle of detection beam.

FIG. 19 plots the dependence of the peak resonant wavelength upon the incident illumination angle. The simulation shows that there is a strong correlation between the angle of incident light, and the peak wavelength that is measured. This result implies that the collimation of the illuminating beam, and the alignment between the illuminating beam and the reflected beam will directly affect the resonant peak linewidth that is measured. If the collimation of the illuminating beam is poor, a range illuminating angles will be incident on the biosensor surface, and a wider resonant peak will be measured than if purely collimated light were incident.

Because the lower sensitivity limit of a biosensor is related to the ability to determine the peak maxima, it is important to measure a narrow resonant peak. Therefore, the use of a collimating illumination system with the biosensor provides for the highest possible sensitivity.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions of illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths due to the dependence shown in FIG. 19. Thus, wider resonant peaks are measured than might otherwise be possible.

Figure 18:
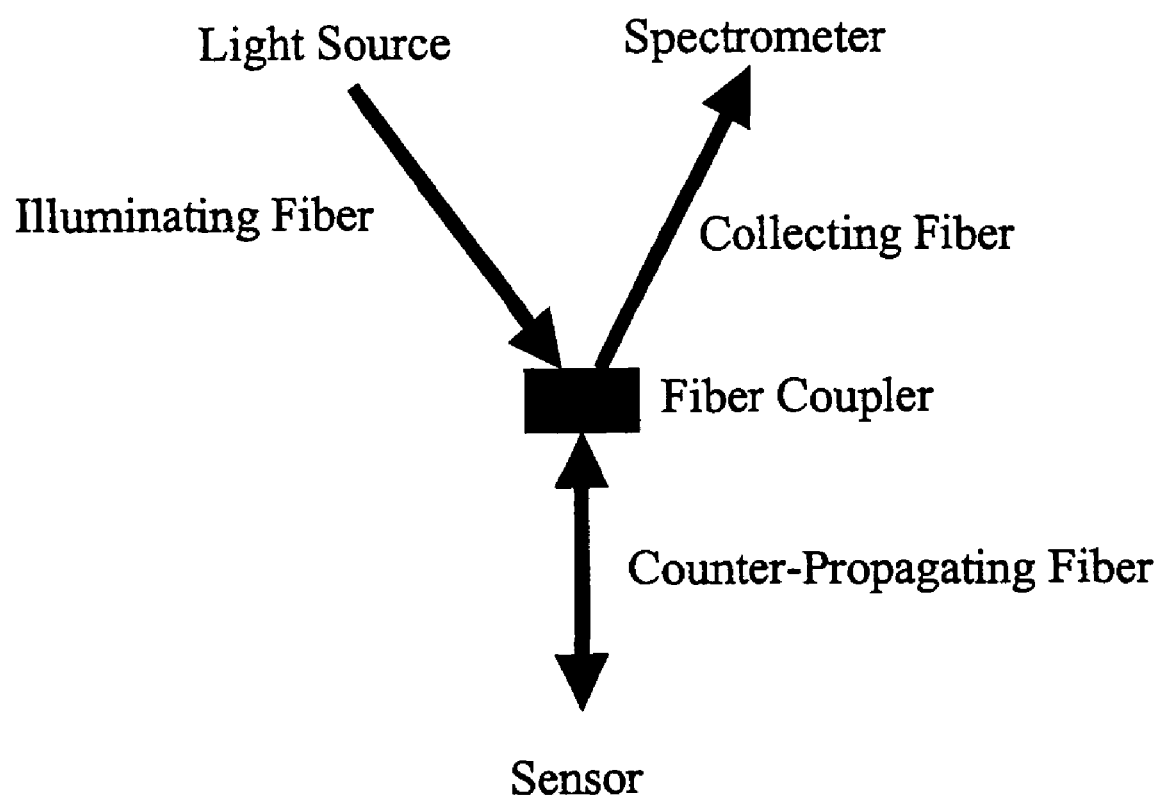
FIG. 18 shows an example of the use of two coupled fibers to illuminate and collect reflected light from a biosensor.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals. An example of such a detection system is shown in FIG. 18.

Figure 20:
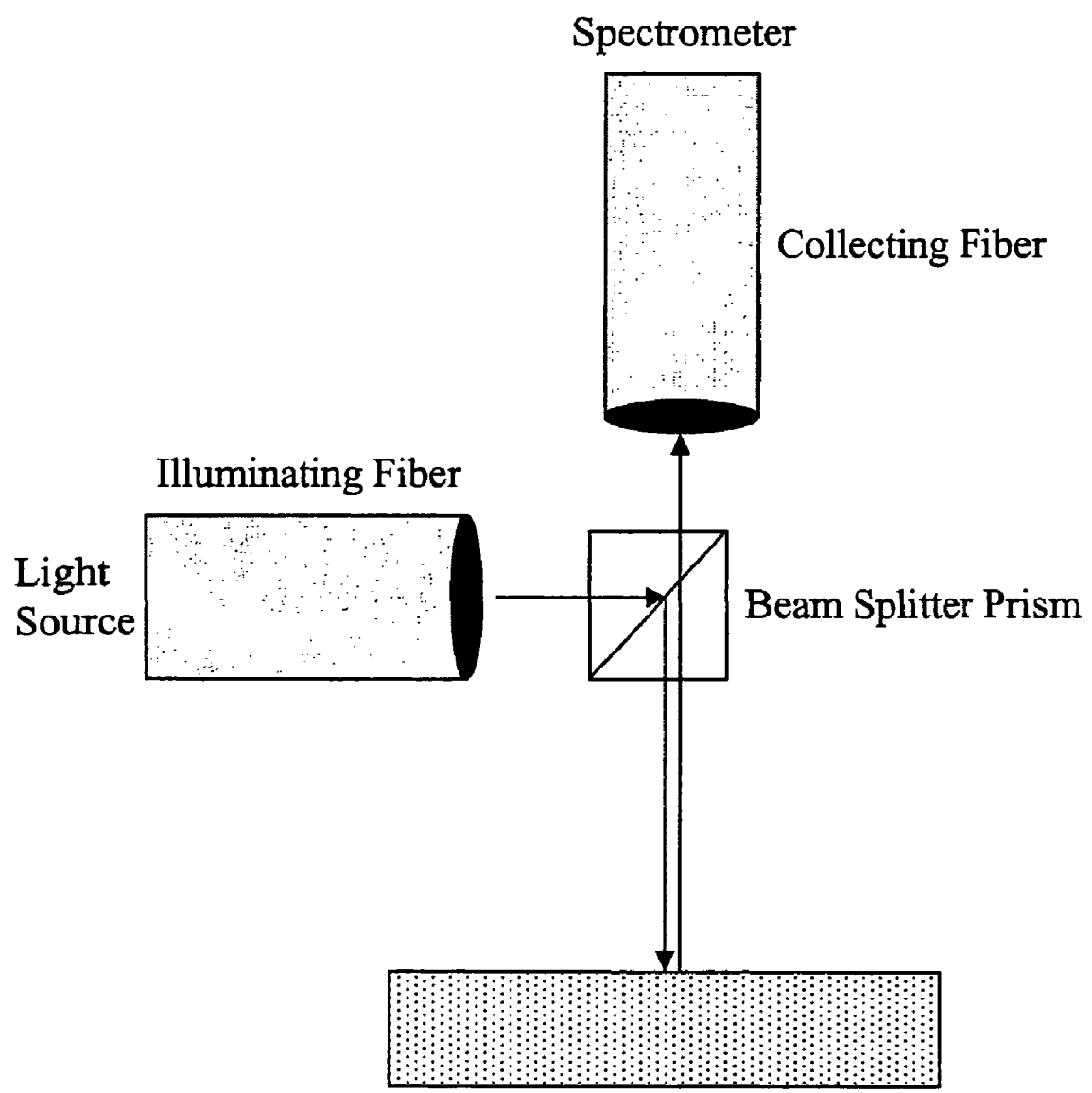
FIG. 20 shows an example of the use of a beam splitter to enable illuminating and reflected light to share a common collimated optical path to a biosensor.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. An example of such a detection device is shown in FIG. 20. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. FIG. 19 depicts this dependence as modeled for a biosensor of the invention. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

Figure 21:
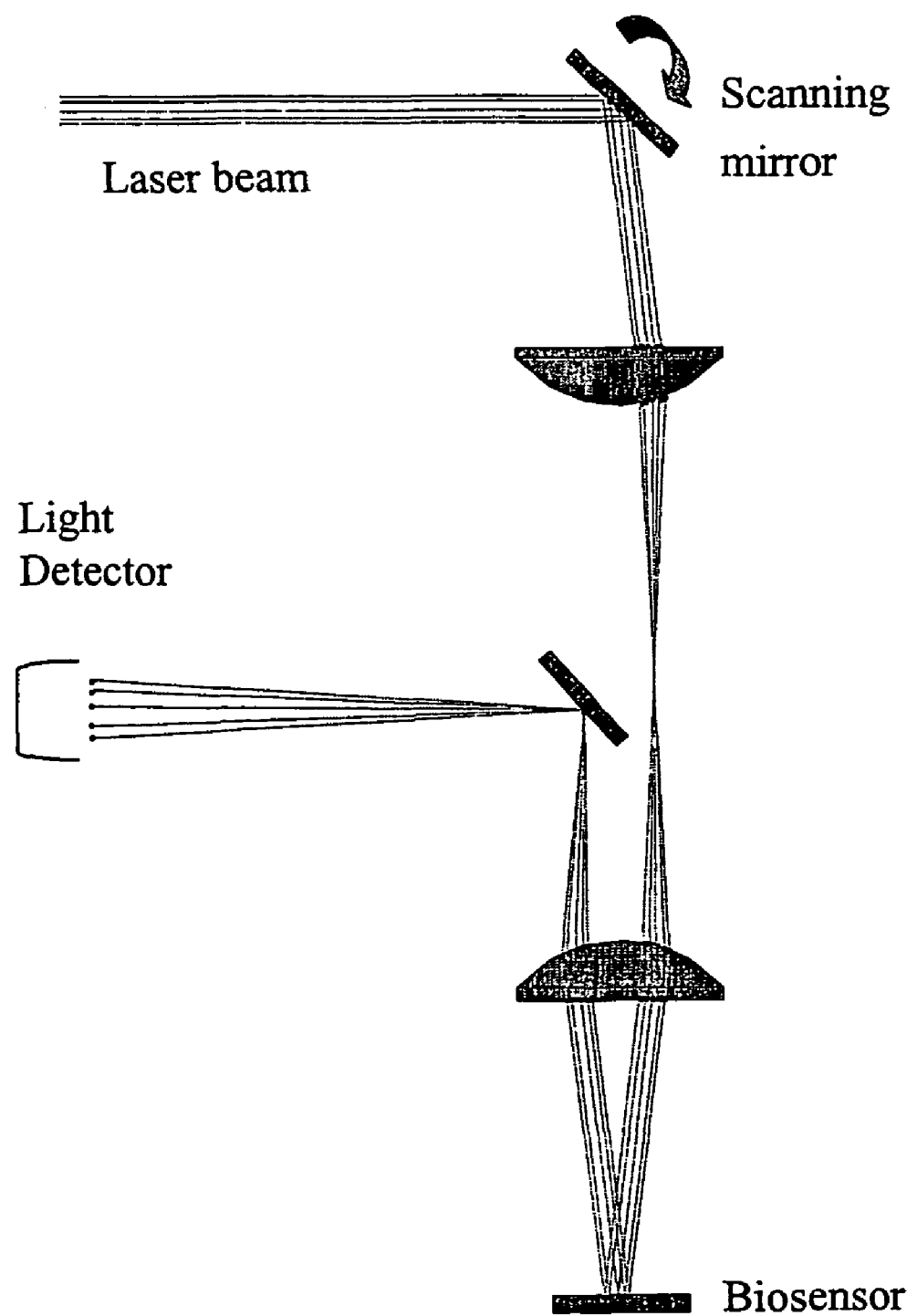
FIG. 21 shows an example of a system for angular scanning of a biosensor.
Figure 52:
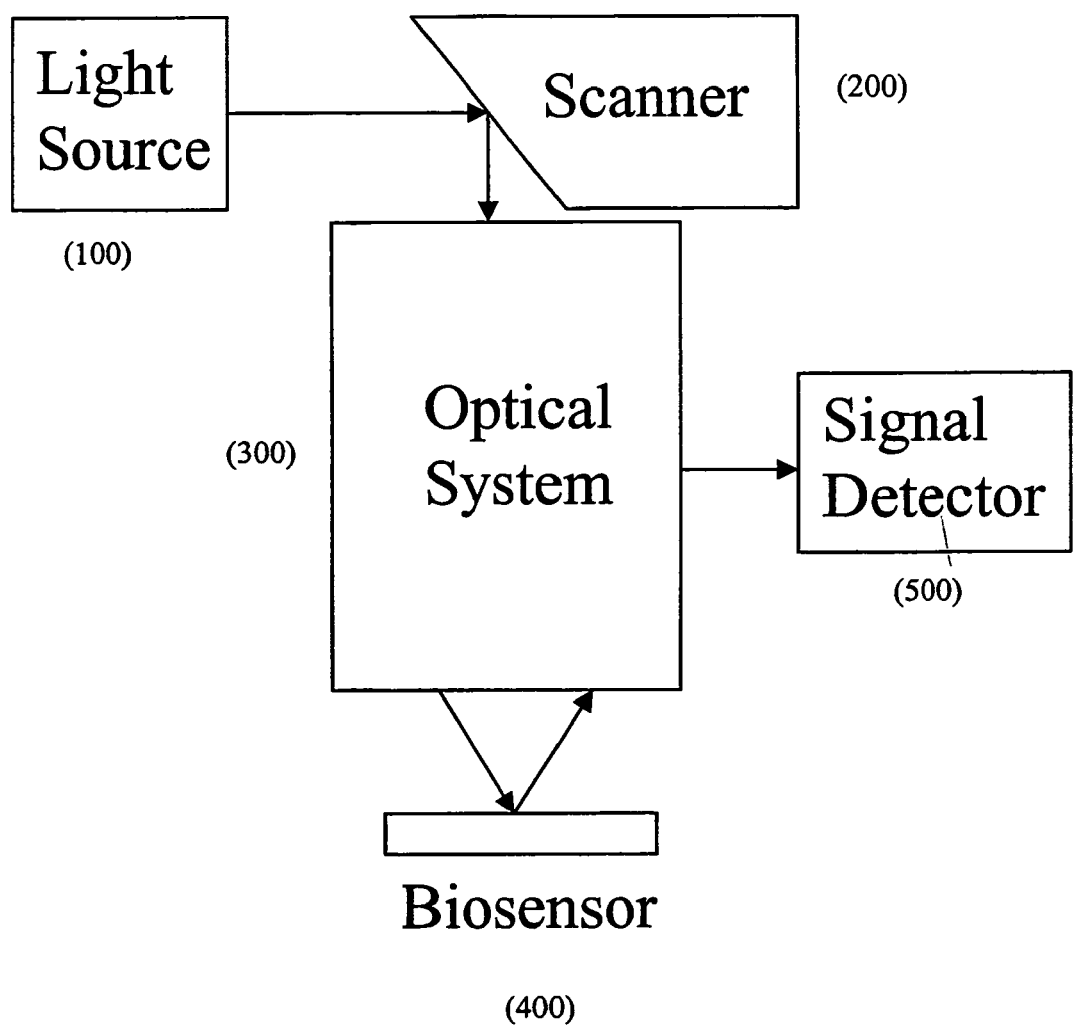
FIG. 52 shows a schematic diagram of a detection system.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. An example of such a detection system is shown in FIG. 52. A light source (100) provides light to a scanner device (200), which directs the light into an optical system (300) The optical system (300) directs light to a biosensor (400) Light is reflected from the biosensor (400) to the optical system (300), which then directs the light into a light signal detector (500). One embodiment of a detection system is shown in FIG. 21, which demonstrates that while the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. The example shown in FIG. 21 includes a simple optical system for angular scanning. It consists of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.,* 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning.

Fiber Probe Biosensor

Figure 17:
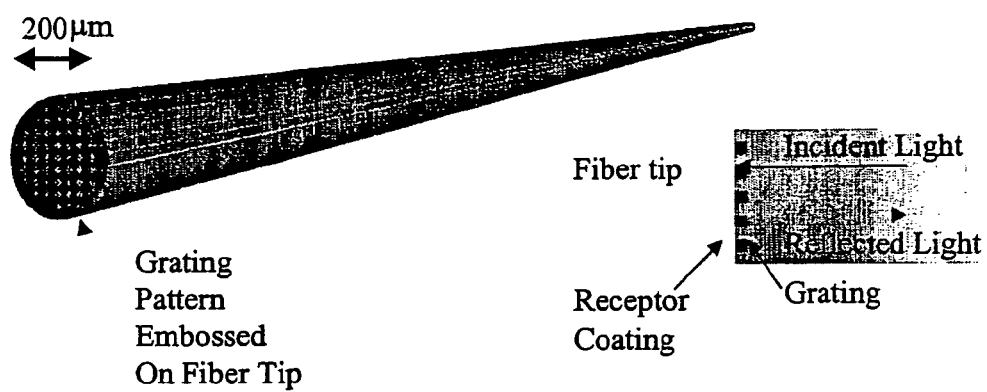
FIG. 17 demonstrates an example of a biosensor that occurs on the tip of a fiber probe for in vivo detection of biochemical substances.

A biosensor of the invention can occur on the tip of a multi-mode fiber optic probe. This fiber optic probe allows for in vivo detection of biomarkers for diseases and conditions, such as, for example, cardiac artery disease, cancer, inflammation, and sepsis. A single biosensor element (comprising, for example, several hundred grating periods) can be fabricated into the tip of a fiber optic probe, or fabricated from a glass substrate and attached to the tip of a fiber optic probe. See FIG. 17. A single fiber is used to provide illumination and measure resonant reflected signal.

For example, a fiber probe structure similar to that shown in FIG. 18 can be used to couple an illuminating fiber and detecting fiber into a single counterpropagating fiber with a biosensor embedded or attached to its tip. The fiber optic probe is inserted into a mammalian body, for example, a human body. illumination and detection of a reflected signal can occur while the probe is inserted in the body.

Mathematical Resonant Peak Determination

The sensitivity of a biosensor is determined by the shift in the location of the resonant peak when material is bound to the biosensor surface. Because of noise inherent in the spectrum, it is preferable to use a procedure for determining an analytical curve—the turning point (i.e., peak) of which is well defined. Furthermore, the peak corresponding to an analytic expression can be preferably determined to greater than sub-sampling-interval accuracy, providing even greater sensitivity.

One embodiment of the invention provides a method for determining a location of a resonant peak for a binding partner in a resonant reflectance spectrum with a colorimetric resonant biosensor. The method comprises selecting a set of resonant reflectance data for a plurality of colorimetric resonant biosensors or a plurality of biosensor distinct locations. The set of resonant reflectance data is collected by illuminating a colorimetric resonant diffractive grating surface with a light source and measuring reflected light at a pre-determined incidence. The colorimetric resonant diffractive grating surface is used as a surface binding platform for one or more specific binding substances such that binding partners can be detected without use of a molecular label.

The step of selecting a set of resonant reflectance data can include selecting a set of resonant reflectance data:

$x_i$ and $y_i$ for i=1, 2, 3, ... n, wherein $x_i$ is where a first measurement includes a first reflectance spectra of one or more specific binding substances attached to the colorimetric resonant diffractive grating surface, $y_i$ and a second measurement and includes a second reflectance spectra of the one or more specific binding substances after a plurality of binding partners are applied to colorimetric resonant diffractive grating surface including the one or more specific binding substances, and n is a total number of measurements collected.

The set of resonant reflectance data includes a plurality of sets of two measurements, where a first measurement includes a first reflectance spectra of one or more specific binding substances that are attached to the colorimetric resonant diffractive grating surface and a second measurement includes a second reflectance spectra of the one or more specific binding substances after one or more binding partners are applied to the colorimetric resonant diffractive grating surface including the one or more specific binding substances. A difference in a peak wavelength between the first and second measurement is a measurement of an amount of binding partners that bound to the one or more specific binding substances. A sensitivity of a colorimetric resonant biosensor can be determined by a shift in a location of a resonant peak in the plurality of sets of two measurements in the set of resonant reflectance data.

A maximum value for a second measurement from the plurality of sets of two measurements is determined from the set of resonant reflectance data for the plurality of binding partners, wherein the maximum value includes inherent noise included in the resonant reflectance data. A maximum value for a second measurement can include determining a maximum value $y_k$ such that:

$(y_k >= y_i)$ for all $i \neq k$.

It is determined whether the maximum value is greater than a pre-determined threshold. This can be calculated by, for example, computing a mean of the set of resonant reflectance data; computing a standard deviation of the set of resonant reflectance data; and determining whether (($y_k$–mean)/standard deviation) is greater than a pre-determined threshold. The pre-determined threshold is determined by the user. The user will determine what amount of sensitivity is desired and will set the pre-determined threshold accordingly.

If the maximum value is greater than a pre-determined threshold a curve-fit region around the determined maximum value is defined. The step of defining a curve-fit region around the determined maximum value can include, for example:

defining a curve-fit region of (2w+1) bins, wherein w is a pre-determined accuracy value;

extracting $(x_i, k-w<=i<=k+w)$; and extracting $(y_i, k-w<=i<=k+w)$.

A curve-fitting procedure is performed to fit a curve around the curve-fit region, wherein the curve-fitting procedure removes a pre-determined amount of inherent noise included in the resonant reflectance data. A curve-fitting procedure can include, for example:

computing $g_i = \ln y_i$;

performing a $2^{nd}$ order polynomial fit on $g_i$ to obtain $g'_i$ defined on $(x_i, k-w<=i<=k+w)$;

determining from the $2^{nd}$ order polynomial fit coefficients a, b and c of for $(ax^2+bx+c)-$; and computing $y'_i = e^{g'_i}$.

The location of a maximum resonant peak is determined on the fitted curve, which can include, for example, determining a location of maximum resonant peak $(x_p = (-b)/2a)$. A value of the maximum resonant peak is determined, wherein the value of the maximum resonant peak is used to identify an amount of biomolecular binding of the one or more specific binding substances to the one or more binding partners. A value of the maximum resonant peak can include, for example, determining the value with of $x_p$ at $y'_p$.

One embodiment of the invention comprises a computer readable medium having stored therein instructions for causing a processor to execute a method for determining a location of a resonant peak for a binding partner in a resonant reflectance spectrum with a colorimetric resonant biosensor. A computer readable medium can include, for example, magnetic disks, optical disks, organic memory, and any other volatile (e.g., Random Access Memory ("RAM")) or non-volatile (e.g., Read-Only Memory ("ROM")) mass storage system readable by the processor. The computer readable medium includes cooperating or interconnected computer readable medium, which exist exclusively on a processing system or to be distributed among multiple interconnected processing systems that can be local or remote to the processing system.

The following are provided for exemplification purpose only and are not intended to limit the scope of the invention described in broad terms above. All references cited in this disclosure are incorporated herein by reference.

EXAMPLE 1

Fabrication of a SWS Biosensor

An example of biosensor fabrication begins with a flat glass substrate that is coated with a thin layer (180 nm) of silicon nitride by plasma-enhanced chemical vapor deposition (PECVD).

Figure 22:
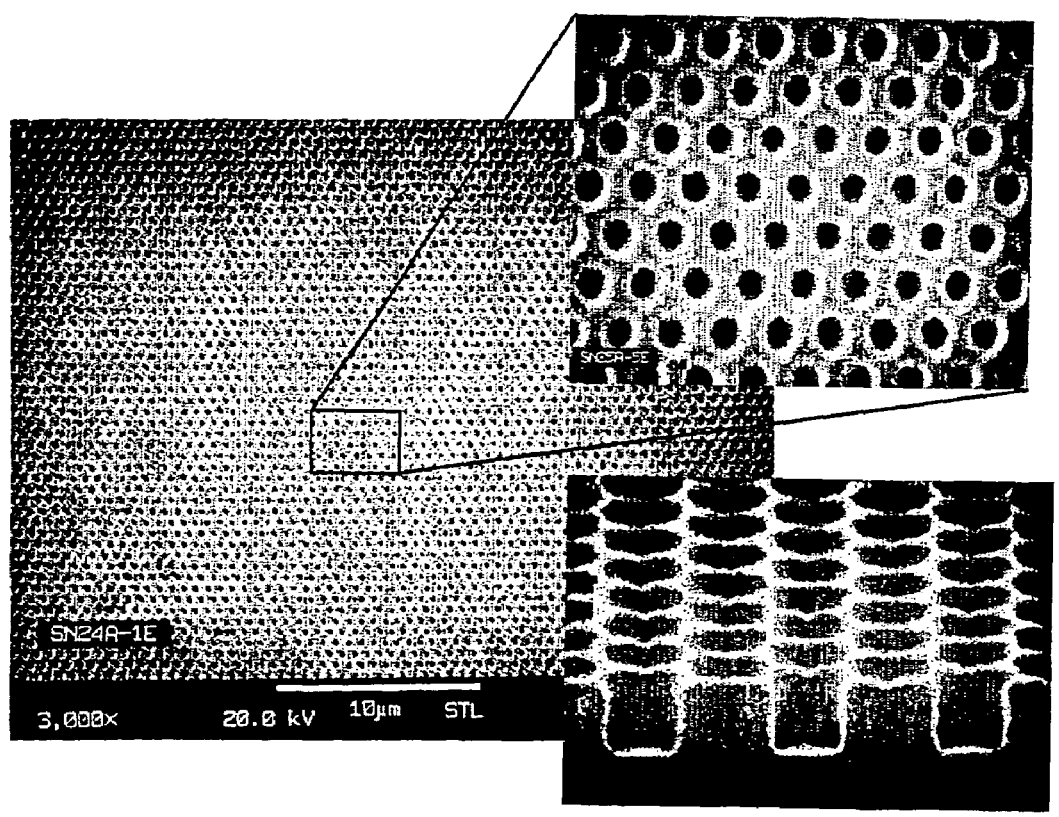
FIG. 22 shows SEM photographs of a photoresist grating structure in plan view (center and upper right) and cross-section (lower right).
Figure 23:
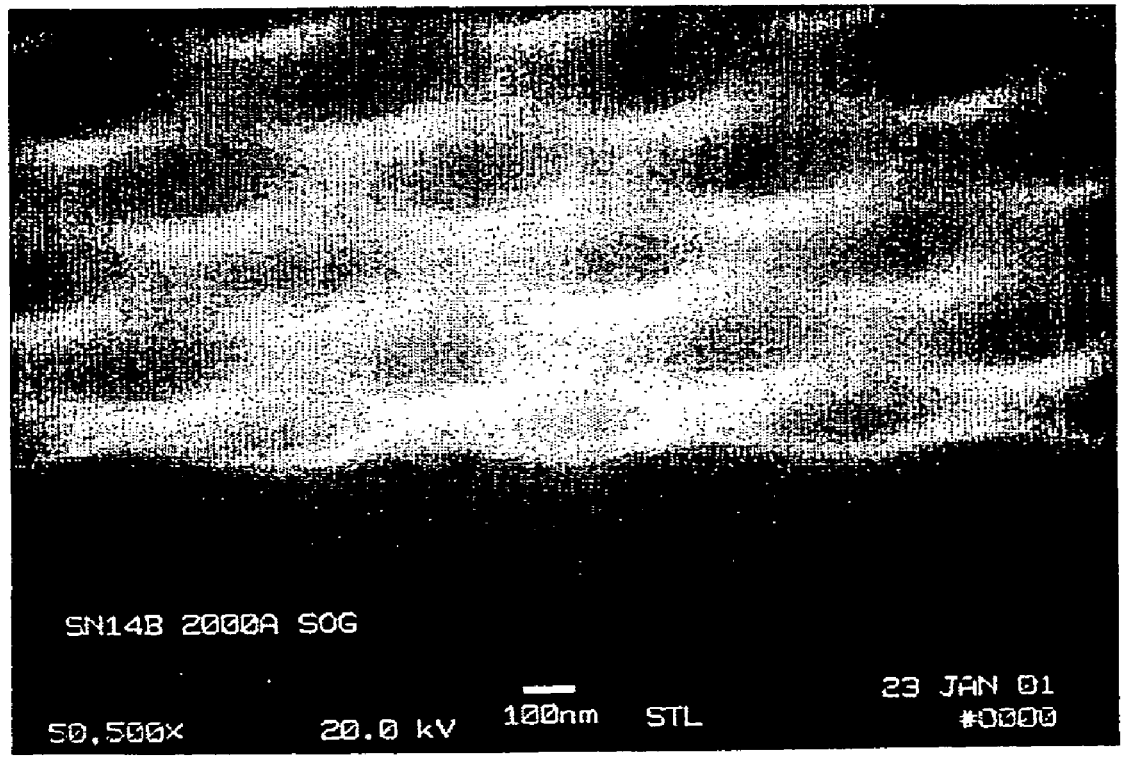
FIG. 23 shows a SEM cross-section photograph of a grating structure after spin-on glass is applied over a silicon nitride grating.
Figure 24:
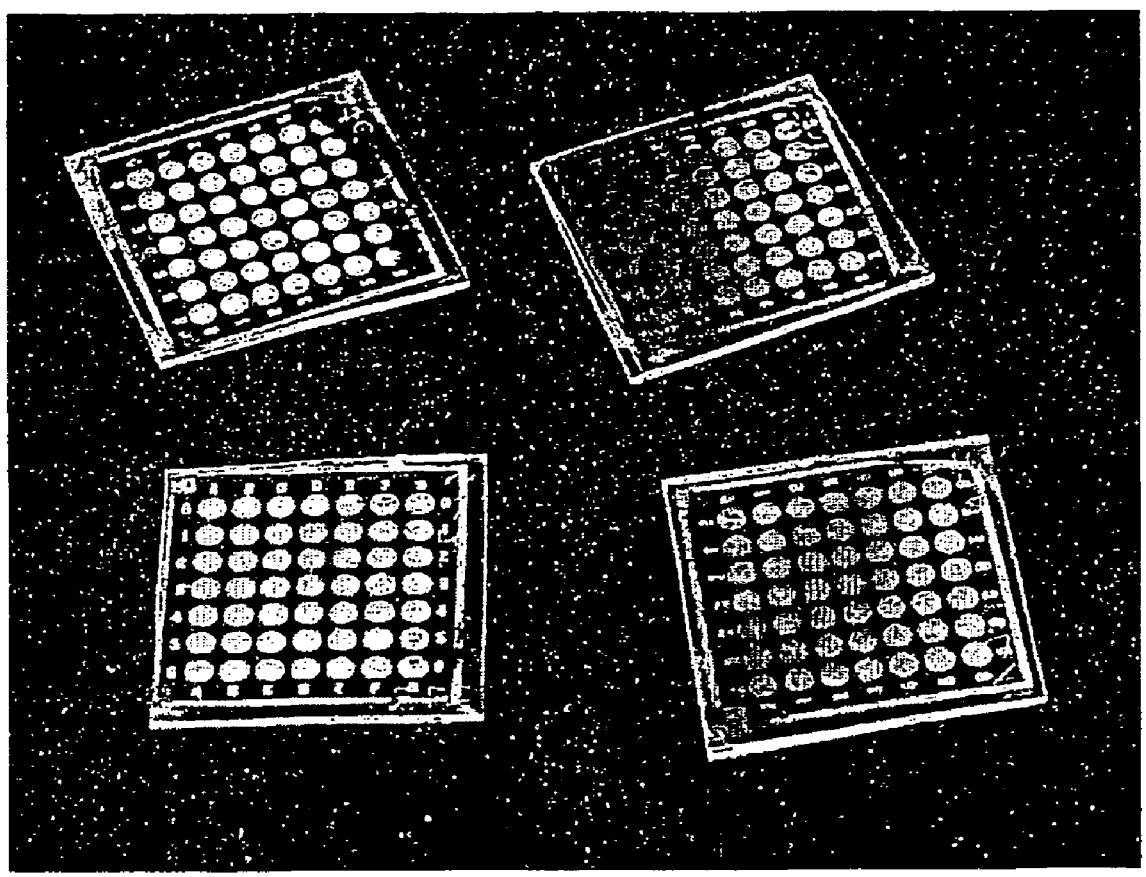
FIG. 24 shows examples of biosensor chips (1.5×1.5-inch). Circular areas are regions where the resonant structure is defined.

The desired structure is first produced in photoresist by coherently exposing a thin photoresist film to three laser beams, as described in previously (Cowen, "The recording and large scale replication of crossed holographic grating arrays using multiple beam interferometry," in *International Conference on the Application, Theory, and Fabrication of Periodic Structures, Diffraction Gratings, and Moire Phenomena II*, J. M. Lerner, ed., Proc. Soc. Photo-Opt. Instrum. Eng., 503, 120-129, 1984; Cowen, "Holographic honeycomb microlens," Opt. Eng. 24, 796-802 (1985); Cowen & Slafer, "The recording and replication of holographic micropatterns for the ordering of photographic emulsion grains in film systems," *J. Imaging Sci.* 31, 100-107, 1987. The nonlinear etching characteristics of photoresist are used to develop the exposed film to create a pattern of holes within a hexagonal grid, as shown in FIG. 22. The photoresist pattern is transferred into the silicon nitride layer using reactive ion etching (RIE). The photoresist is removed, and a cover layer of spin-on-glass (SOG) is applied (Honeywell Electronic Materials, Sunnyvale, Calif.) to fill in the open regions of the silicon nitride grating. The structure of the top surface of the finished biosensor is shown in FIG. 23. A photograph of finished parts are shown in FIG. 24.

EXAMPLE 2

A SRVD biosensor was prepared by making five circular diffuse grating holograms by stamping a metal master plate into vinyl. The circular holograms were cut out and glued to glass slides. The slides were coated with 1000 angstroms of aluminum. In air, the resonant wavelength of the grating is ~380 nm, and therefore, no reflected color is visible. When the grating is covered with water, a light blue reflection is observed. Reflected wavelength shifts are observable and measurable while the grating is covered with a liquid, or if a specific binding substances and/or binding partners cover the structure.

Both proteins and bacteria were immobilized onto the surface of a SRVD biosensor at high concentration and the wavelength shift was measured. For each material, a 20 µl droplet is placed onto a biosensor distinct location and allowed to dry in air. At 1 µg/ml protein concentration, a 20 µl droplet spreads out to cover a 1 cm diameter circle and deposits about $2 \times 10^{-8}$ grams of material. The surface density is 25.6 ng/mm$^2$.

For high concentration protein immobilization (biosensor 4) a 10 µl droplet of 0.8 g bovine serum albumin (BSA) in 40 ml DI H$_2$O is spread out to cover a 1 cm diameter circle on the surface of a biosensor. The droplet deposits 0.0002 g of BSA, for a density of 2.5e-6 g/mm$^2$. After protein deposition, biosensor 4 has a green resonance in air.

For bacteria immobilization (biosensor 2) a 20 µl droplet of NECK borrelia Lyme Disease bacteria (1.8e8 cfu/ml) was deposited on the surface of a biosensor. After bacteria deposition, the biosensor looks grey in air.

For low concentration protein immobilization (biosensor 6) a 10 µl droplet of 0.02% of BSA in DI H$_2$O (0.8 g BSA in 40 ml DI H$_2$O) is spread out to cover a 1 cm diameter circle. The droplet deposits 0.000002 g of BSA for a density of 2.5e-8 g/mm$^2$. After protein deposition, biosensor 6 looks grey in air.

In order to obtain quantitative data on the extent of surface modification resulting from the above treatments, the biosensors were measured using a spectrometer.

Figure 25:
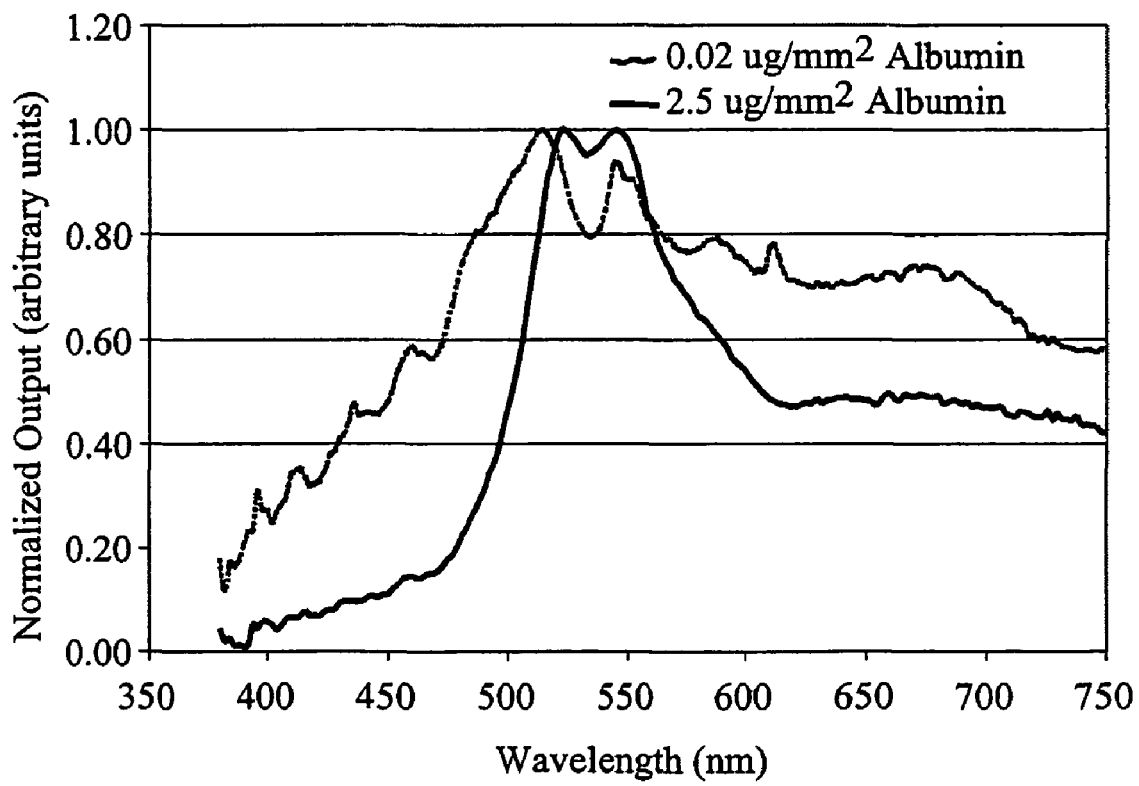
FIG. 25 shows response as a function of wavelength of a biosensor that BSA had been deposited at high concentration, measured in air. Before protein deposition, the resonant wavelength of the biosensor is 380 nm and is not observable with the instrument used for this experiment.

Because a green resonance signal was immediately visually observed on the biosensor upon which high concentration BSA was deposited (biosensor 4), it was measured in air. FIG. 25 shows two peaks at 540 nm and 550 nm in green wavelengths where none were present before protein deposition, indicating that the presence of a protein thin film is sufficient to result in a strong shift in resonant wavelength of a surface relief structure.

Figure 26:
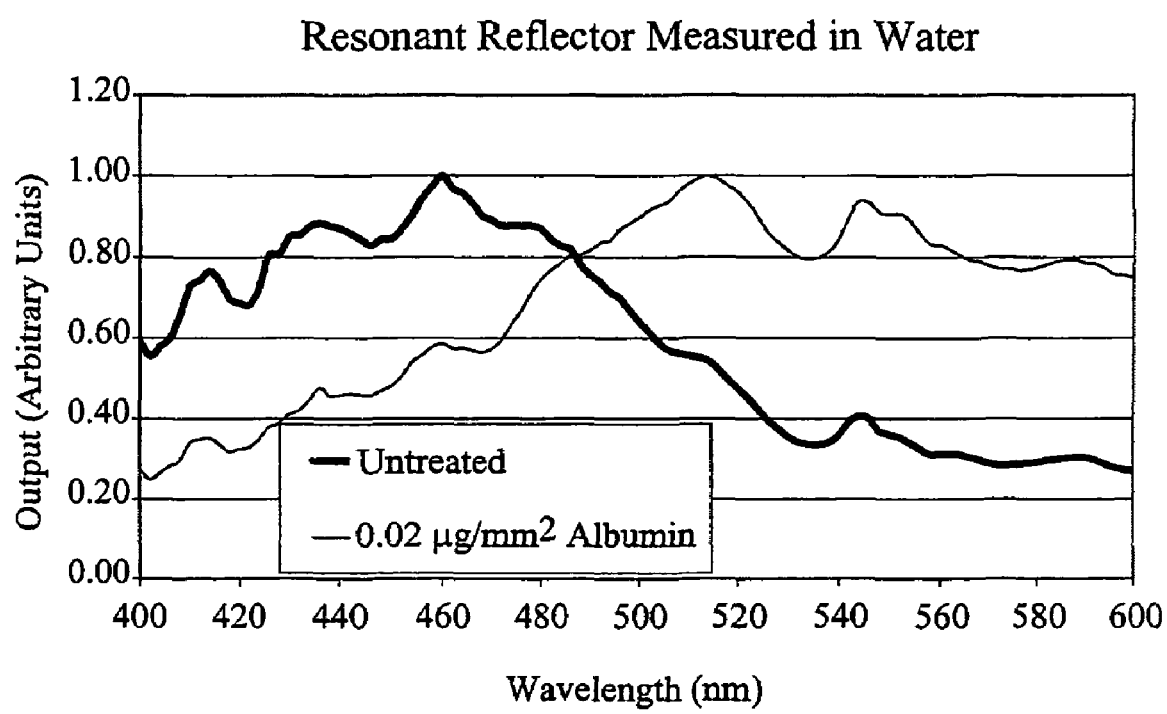
FIG. 26 shows response as a function of wavelength comparing an untreated biosensor with one upon which BSA had been deposited. Both measurements were taken with water on the biosensor's surface.
Figure 27:
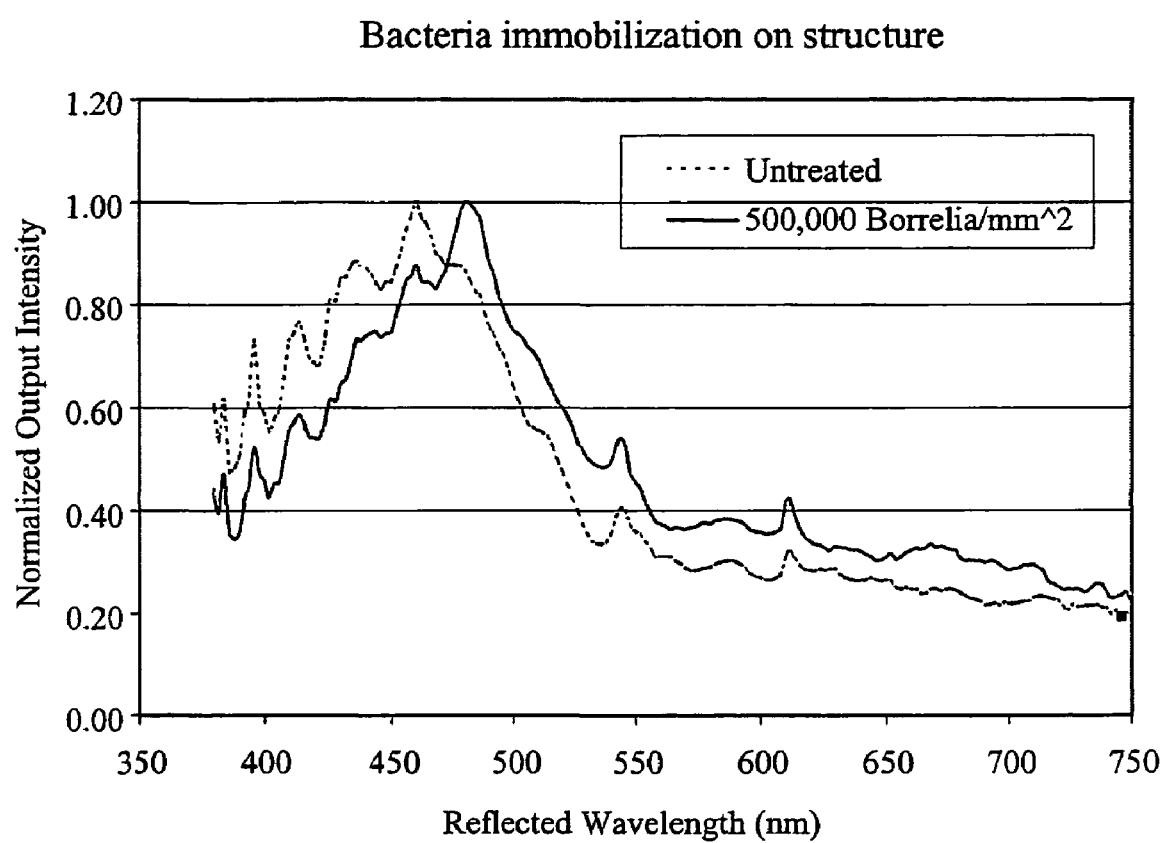
FIG. 27 shows response as a function of wavelength of a biosensor that *Borrelia* bacteria has been deposited at high concentration and measured in water.
Figure 28:
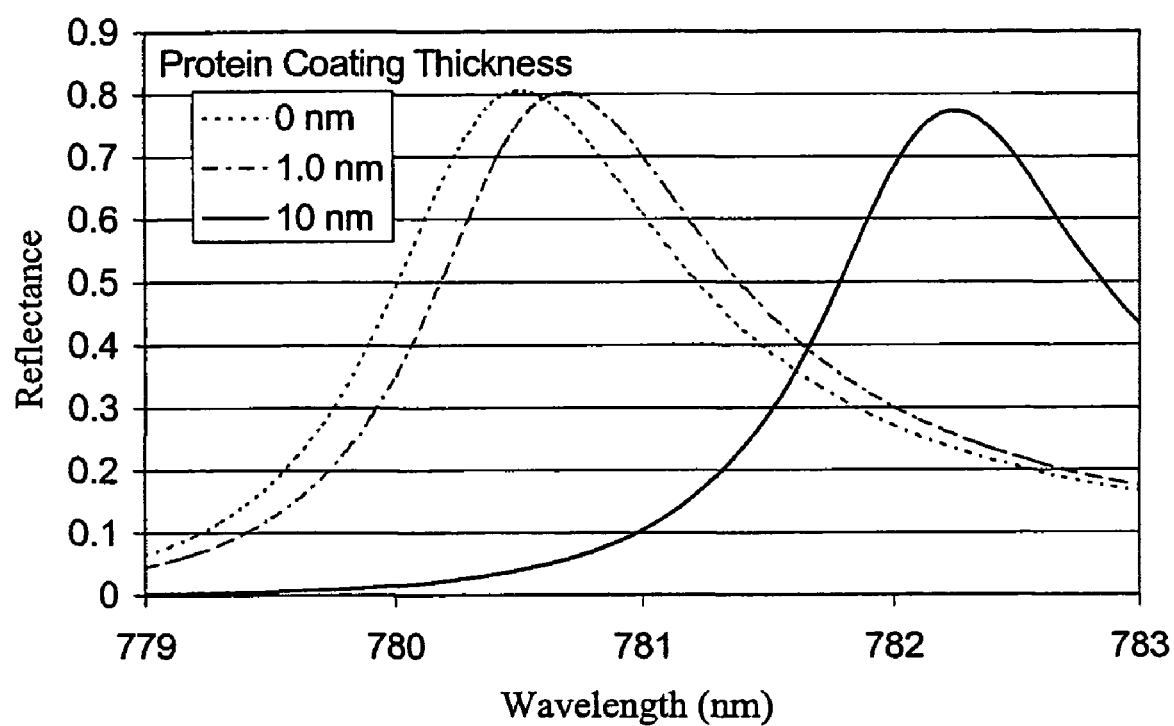
FIG. 28 shows a computer simulation of a biosensor demonstrating the shift of resonance to longer wavelengths as biomolecules are deposited on the surface.
Figure 29:
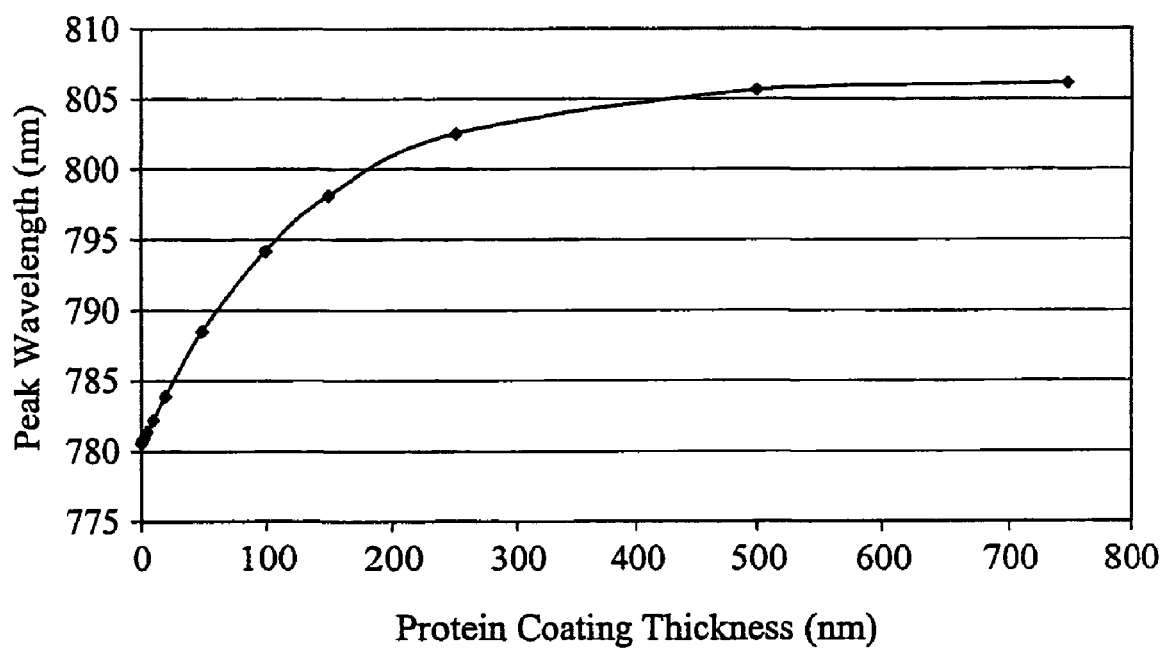
FIG. 29 shows a computer simulation demonstrating the dependence of peak reflected wavelength on protein coating thickness. This particular biosensor has a dynamic range of 250 nm deposited biomaterial before the response begins to saturate.
Figure 30:
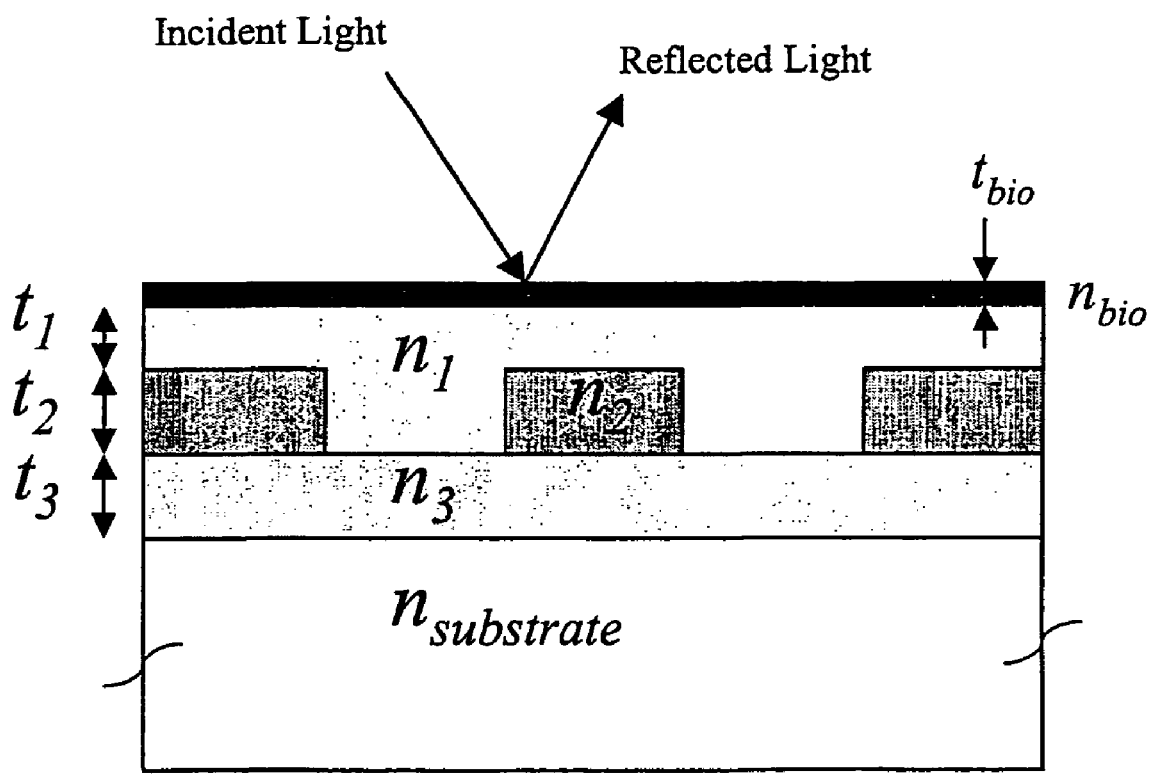
FIG. 30 shows an embodiment of a biosensor. $n_{substrate}$ represents the refractive index of a substrate. $n_1$ represents the refractive index of an optical cover layer. $n_2$ represents the refractive index of a two-dimensional grating. $n_3$ represents the refractive index of a high refractive index material such as silicon nitride. $n_{bio}$ represents the refractive index of one or more specific binding substances. $t_1$ represents the thickness of a cover layer. $t_2$ represents the thickness of a two-dimensional grating. $t_3$ represents the thickness of a high refractive index material. $t_{bio}$ represents the thickness of a specific binding substance layer.
Figure 31:
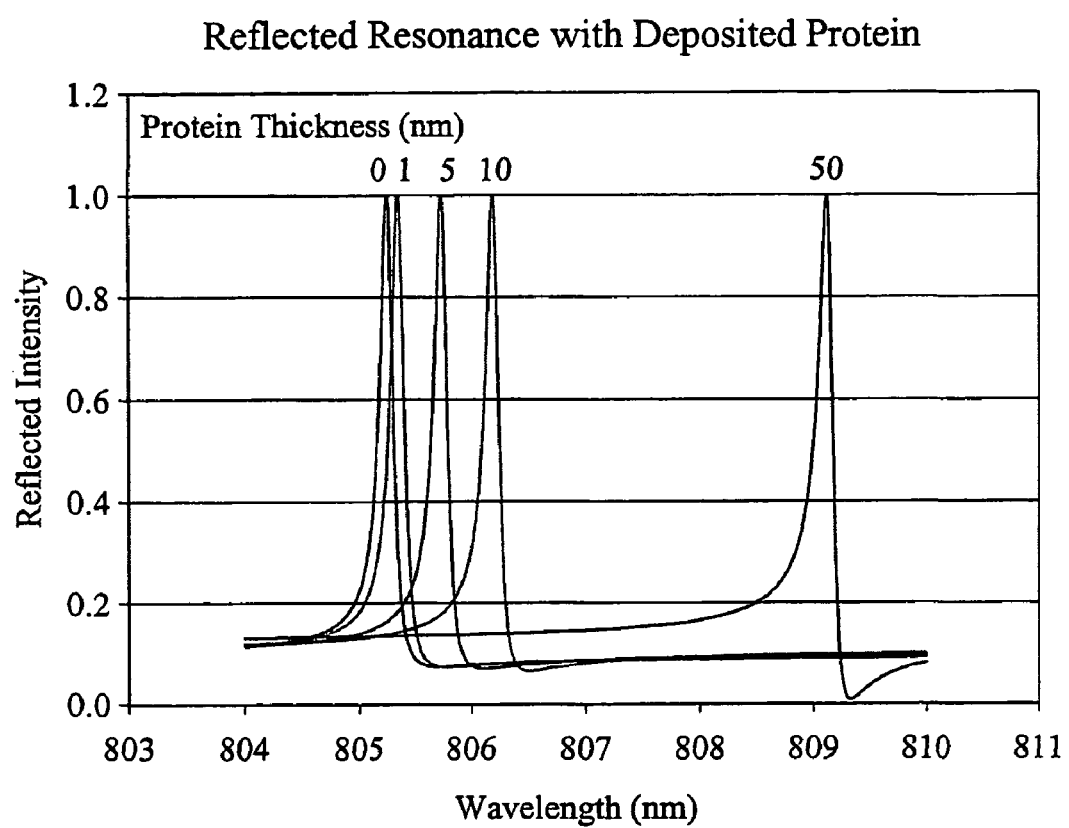
FIG. 31 shows reflected intensity as a function of wavelength for a resonant grating structure when various thicknesses of protein are incorporated onto the upper surface.
Figure 32:
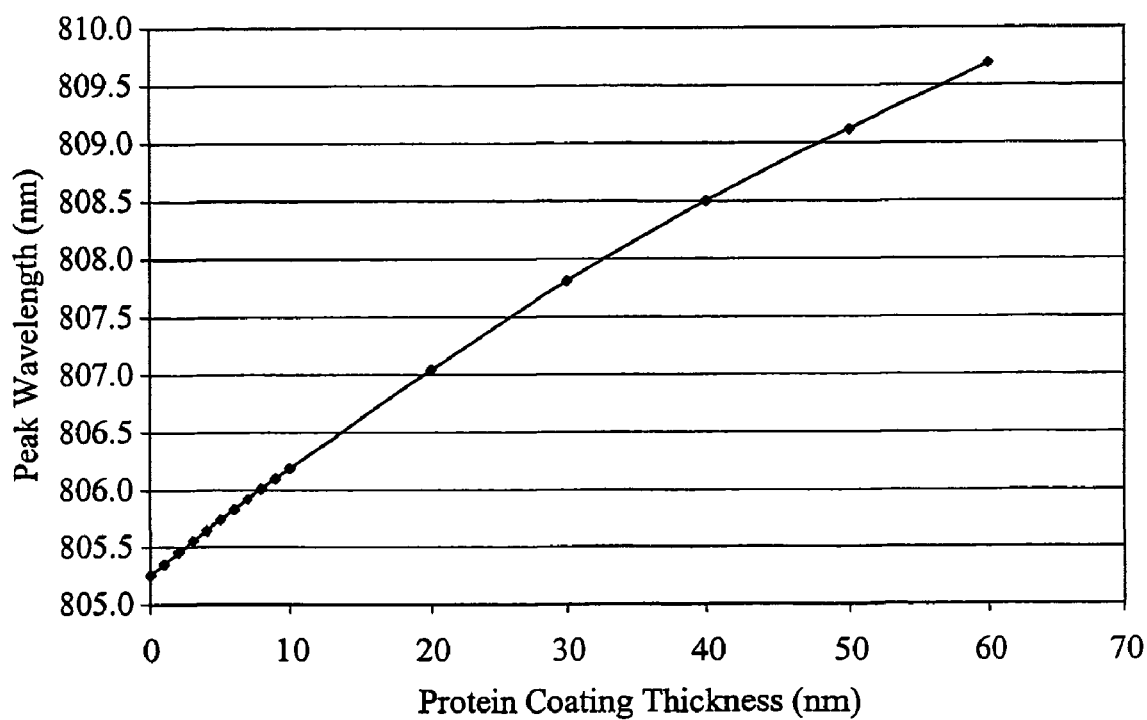
FIG. 32 shows a linear relationship between reflected wavelength and protein coating thickness for a biosensor shown in FIG. 30.
Figure 33:
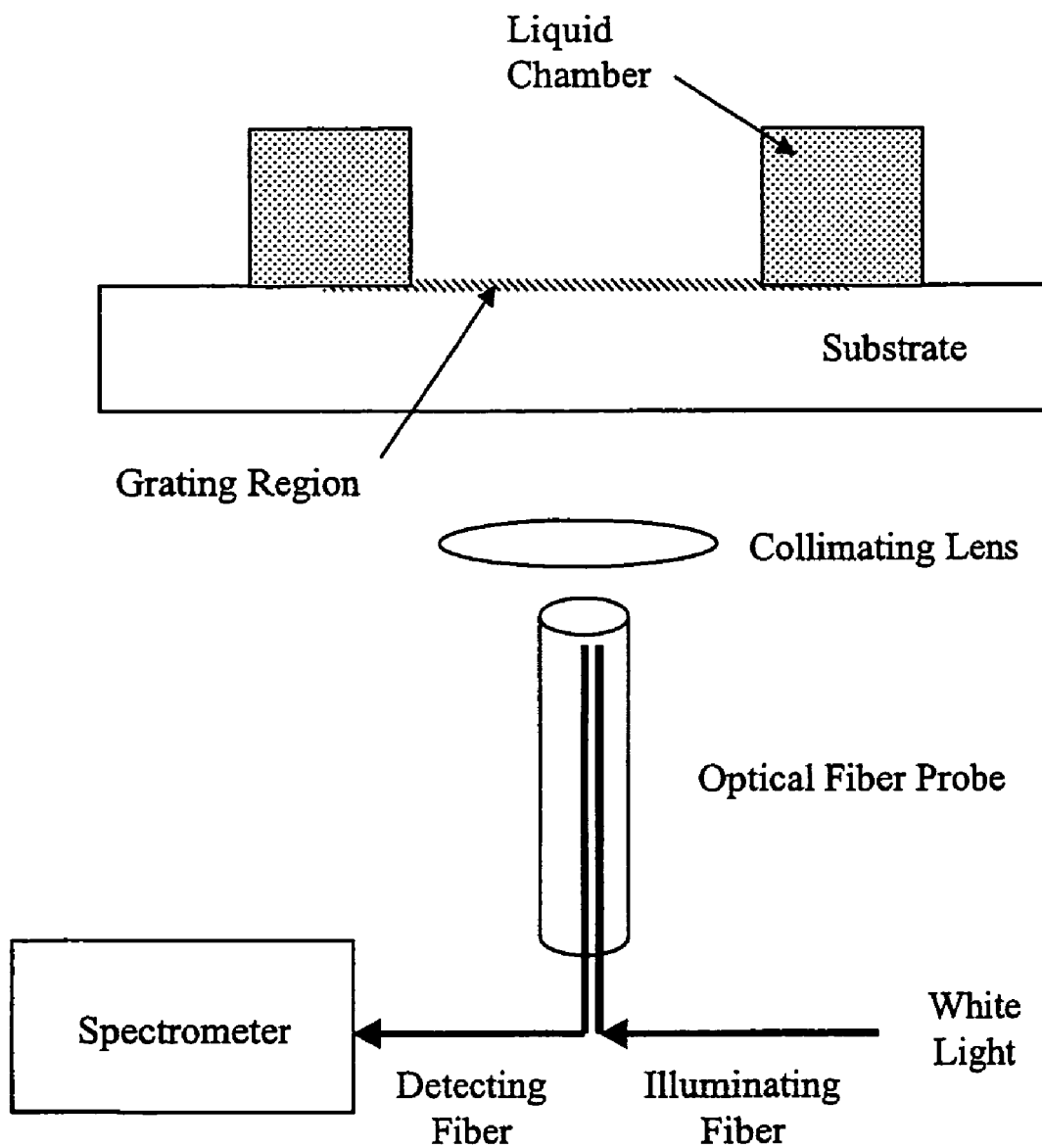
FIG. 33 shows instrumentation that can be used to read output of a biosensor. A collimated light source is directed at a biosensor surface at normal incidence through an optical fiber, while a second parallel fiber collects the light reflected at normal incidence. A spectrometer records the reflectance as a function of wavelength.

Because no visible resonant wavelength was observed in air for the slide upon which a low concentration of protein was applied (biosensor 6), it was measured with distilled water on surface and compared against a biosensor which had no protein treatment. FIG. 26 shows that the resonant wavelength for the slide with protein applied shifted to green compared to a water-coated slide that had not been treated.

Finally, a water droplet containing Lyme Disease bacteria *Borrelia burgdorferi* was applied to a grating structure and allowed to dry in air (biosensor 2). Because no visually observed resonance occurred in air after bacteria deposition, the biosensor was measured with distilled water on the surface and compared to a water-coated biosensor that had undergone no other treatment. As shown in FIG. 27, the application of bacteria results in a resonant frequency shift to longer wavelengths.

EXAMPLE 3

Computer Model of Biosensor

To demonstrate the concept that a resonant grating structure can be used as a biosensor by measuring the reflected wavelength shift that is induced when biological material is adsorbed onto its surface, the structure shown in FIG. 1 was modeled by computer. For purposes of demonstration, the substrate chosen was glass ($n_{substrate}$=1.50). The grating is a two-dimensional pattern of silicon nitride squares ($t_2$=180 nm, $n_2$=2.01, $k_2$=0.001) with a period of 510 nm, and a filling factor of 56.2% (i.e. 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm. To observe the effect on the reflected wavelength of this structure with the deposition of biological material, variable thicknesses of protein ($n_{bio}$=1.5) were added above the glass coating layer.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination may be from any incidence and any polarization.

The results of the computer simulation are shown in FIG. 28 and FIG. 29. As shown in FIG. 28, the resonant structure allows only a single wavelength, near 780 nm, to be reflected from the surface when no protein is present on the surface. Because the peak width at half-maximum is ~1.5 nm, resonant wavelength shifts of ~0.2 m will be easily resolved. FIG. 28 also shows that the resonant wavelength shifts to longer wavelengths as more protein is deposited on the surface of the structure. Protein thickness changes of 2 nm are easily observed. FIG. 29 plots the dependence of resonant wavelength on the protein coating thickness. A near linear relationship between protein thickness and resonant wavelength is observed, indicating that this method of measuring protein adsorption can provide quantitative data. For the simulated structure, FIG. 29 shows that the wavelength shift response becomes saturated when the total deposited protein layer exceeds ~250 nm. This upper limit for detection of deposited material provides adequate dynamic range for any type of biomolecular assay.

EXAMPLE 4

Computer Model of Biosensor

In another embodiment of the invention a biosensor structure shown in FIG. 30 was modeled by computer. For purposes of demonstration, the substrate chosen was glass $n_{substrate}$=1.454 coated with a layer of high refractive index material such as silicon nitride, zinc sulfide, tantalum oxide, or titanium dioxide. In this case, silicon nitride ($t_3$=90 nm, $n_3$=2.02) was used. The grating is two-dimensional pattern of photoresist squares ($t_2$=90 nm, $n_2$=1.625) with a period of 510 μm, and a filling factor of 56.2% (i.e. 56.2% of the surface is covered with photoresist squares while the rest is the area between the squares). The areas between photoresist squares are filled with a lower refractive index material such as glass, plastic, or epoxy. The same material also covers the squares and provides a uniformly flat upper surface. For this simulation, a glass layer was selected ($n_1$=1.45) that covers the photoresist squares by $t_2$=100 nm. To observe the effect on the reflected wavelength of this structure with the deposition of a specific binding substance, variable thicknesses of protein ($n_{bio}$=1.5) were added above the glass coating layer.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination may be from any incidence and any polarization.

The results of the computer simulation are shown in FIG. 31 and FIG. 32. The resonant structure allows only a single wavelength, near 805 nm, to be reflected from the surface when no protein is present on the surface. Because the peak width at half-maximum is <0.25 nm, resonant wavelength shifts of 1.0 nm will be easily resolved. FIG. 31 also shows that the resonant wavelength shifts to longer wavelengths as more protein is deposited on the surface of the structure. Protein thickness changes of 1 nm are easily observed. FIG. 32 plots the dependence of resonant wavelength on the protein coating thickness. A near linear relationship between protein thickness and resonant wavelength is observed, indicating that this method of measuring protein adsorption can provide quantitative data.

EXAMPLE 5

Sensor Readout Instrumentation

In order to detect reflected resonance, a white light source can illuminate a ~1 mm diameter region of a biosensor surface through a 400 micrometer diameter fiber optic and a collimating lens, as shown in FIG. 33. Smaller or larger areas may be sampled through the use of illumination apertures and different lenses. A group of six detection fibers are bundled around the illumination fiber for gathering reflected light for analysis with a spectrometer (Ocean Optics, Dunedin, Fla.). For example, a spectrometer can be centered at a wavelength of 800 nm, with a resolution of ~0.14 nm between sampling bins. The spectrometer integrates reflected signal for 25-75 msec for each measurement. The biosensor sits upon an x-y motion stage so that different regions of the biosensor surface can be addressed in sequence.

Equivalent measurements can be made by either illuminating the top surface of device, or by illuminating through the bottom surface of the transparent substrate. Illumination through the back is preferred when the biosensor surface is immersed in liquid, and is most compatible with measurement of the biosensor when it is incorporated into the bottom surface of, for example, a microwell plate.

EXAMPLE 6

Demonstration of Resonant Reflection

Figure 34:
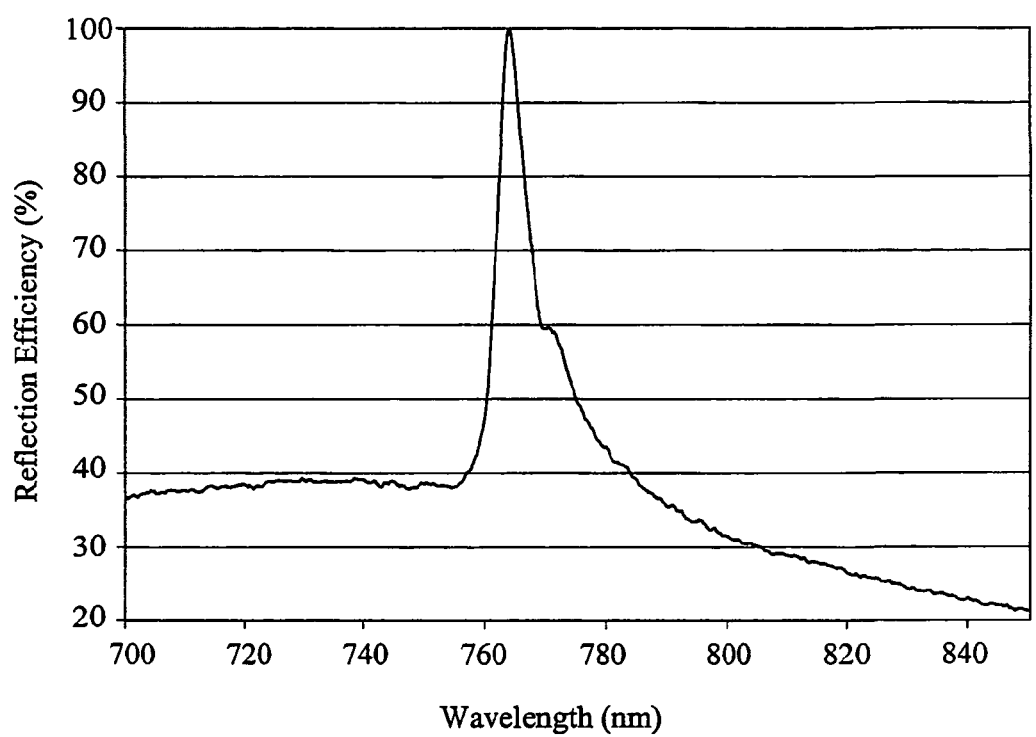
FIG. 34 shows the measured reflectance spectra of a biosensor.

FIG. 34 shows the resonant reflectance spectra taken from a biosensor as shown in FIG. 1 using the instrumentation described in Example 5. The wavelength of the resonance ($\lambda_{peak}$=772.5 nm) compares with the resonant wavelength predicted by the computer model ($\lambda_{peak}$=781 nm), and the measured reflectance efficiency (51%) is comparable to the predicted efficiency (70%). The greatest discrepancy between the measured and predicted characteristics is the linewidth of the resonant peak. The measured full-width at half maximum (FWHM) of the resonance is 6 nm, while the predicted FW is 1.5 nm. As will be shown, the dominant source of the larger measured FWHM is collimation of the illumination optics, which can easily be corrected.

As a basic demonstration of the resonant structure's ability to detect differences in the refractive index of materials in contact with its surface, a biosensor was exposed to a series of liquids with well-characterized optical properties. The liquids used were water, methanol, isopropyl alcohol, acetone, and DMF. A biosensor was placed face-down in a small droplet of each liquid, and the resonant wavelength was measured with a fiber illumination/detection probe facing the biosensor's back side. Table 1 shows the calculated and measured peak resonant wavelength as a biosensor surface is exposed to liquids with variable refractive index demonstrating the correlation between measured and theoretical detection sensitivity. As shown in Table 1, the measured resonant peak positions and measured resonant wavelength shifts are nearly identical to the predicted values. This example demonstrates the underlying sensitivity of the biosensor, and validates the computer model that predicts the wavelength shift due to changes in the material in contact with the surface.

TABLE 1

| Solution | n | Calculated Peak Wavelength (nm) | Shift (nm) | Measured Peak Wavelength (nm) | Shift (nm) |
|---|---|---|---|---|---|
| Water | 1.333 | 791.6 | 0 | 786.08 | 0 |
| Isopropyl | 1.3776 | 795.9 | 4.3 | 789.35 | 3.27 |
| Acetone | 1.3588 | 794 | 2.4 | 788.22 | 2.14 |
| Methanol | 1.3288 | 791.2 | −0.4 | 785.23 | −0.85 |
| DMF | 1.4305 | 802 | 10.4 | 796.41 | 10.33 |

Figure 35:
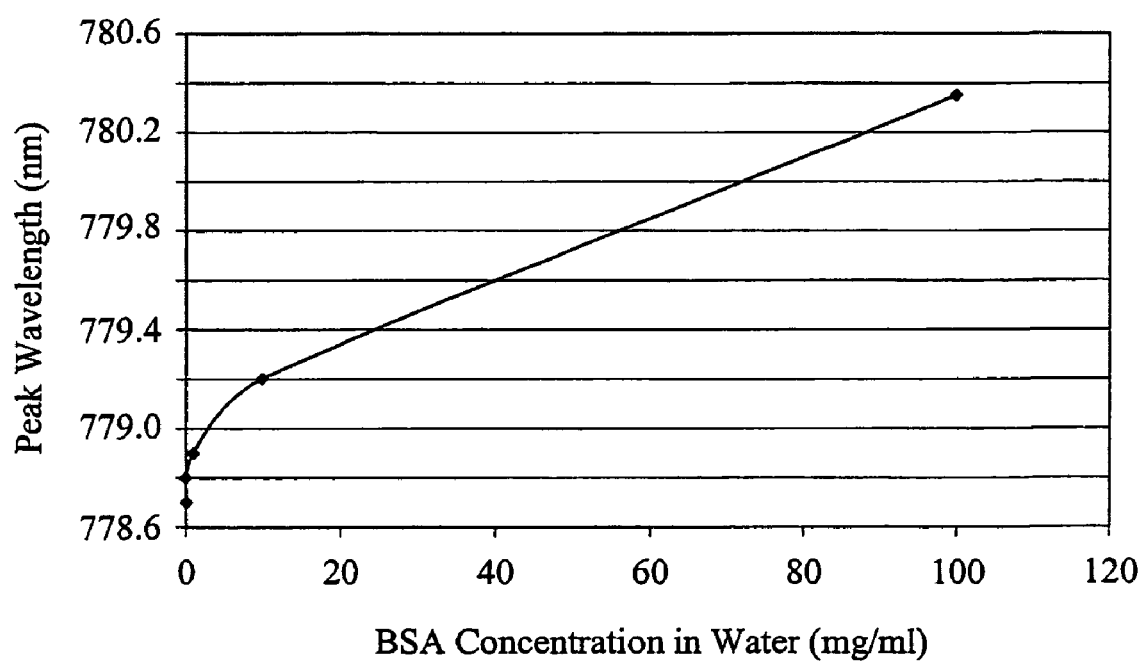
FIG. 35 shows dependence of peak resonant wavelength measured in liquid upon the concentration of protein BSA dissolved in water.
Figure 36:
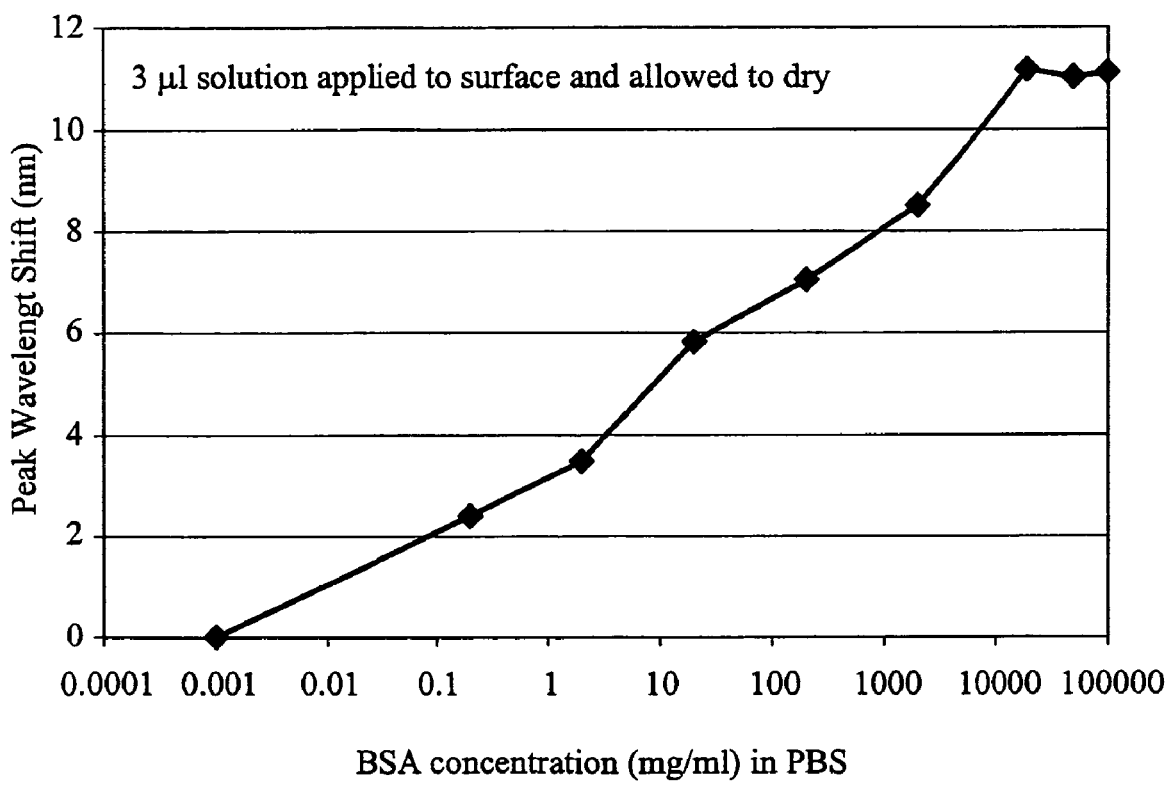
FIG. 36 shows dependence of peak resonance wavelength on the concentration of BSA dissolved in PBS, which was then allowed to dry on a biosensor surface.

Similarly, a biosensor is able to measure the refractive index difference between various buffer solutions. As an example, FIG. 35 shows the variation in peak wavelength with the concentration of bovine serum albumin (BSA) in water. Resonance was measured with the biosensor placed face-down in a droplet of buffer, and rinsed with water between each measurement.

EXAMPLE 7

Immobilized Protein Detection

While the detection experiments shown in Example 6 demonstrate a biosensor's ability to measure small differences in refractive index of liquid solutions, the biosensor is intended to measure specific binding substances and binding partners that are chemically bound to the biosensor surface. In order to demonstrate a biosensor's ability to quantify biomolecules on its surface, droplets of BSA dissolved in PBS at various concentrations were applied to a biosensor as shown in FIG. 1. The 3 μl droplets were allowed to dry in air, leaving a small quantity of BSA distributed over a ~2 mm diameter area. The peak resonant wavelength of each biosensor location was measured before and after droplet deposition, and the peak wavelength shift was recorded. See FIG. 37.

EXAMPLE 8

Immobilization of One or More Specific Binding Substances

The following protocol was used on a colorimetric resonant reflective biosensor to activate the surface with amine functional groups. Amine groups can be used as a general-purpose surface for subsequent covalent binding of several types of linker molecules.

A biosensor of the invention is cleaned by immersing it into piranha etch (70/30% (v/v) concentrated sulfuric acid/30% hydrogen peroxide) for 12 hours. The biosensor was washed thoroughly with water. The biosensor was dipped in 3% 3-aminopropyltriethoxysilane solution in dry acetone for 1 minute and then rinsed with dry acetone and air-dried. The biosensor was then washed with water.

A semi-quantitative method is used to verify the presence of amino groups on the biosensor surface. One biosensor from each batch of amino-functionalized biosensors is washed briefly with 5 mL of 50 mM sodium bicarbonate, pH 8.5. The biosensor is then dipped in 5 mL of 50 mM sodium bicarbonate, pH 8.5 containing 0.1 mM sulfo-succinirnidyl-4-O-(4,4'-dimethoxytrityl)-butyrate (s-SDTB, Pierce, Rockford, Ill.) and shaken vigorously for 30 rminutes. The s-SDTB solution is prepared by dissolving 3.0 mg of s-SDTB in 1 mL of DMF and diluting to 50 mL with 50 mM sodium bicarbonate, pH 8.5. After a 30 minute incubation, the biosensor is washed three times with 20 mL of ddH$_2$O and subsequently treated with 5 mL 30% perchloric acid. The development of an orange-colored solution indicates that the biosensor has been successfully derivatized with amines; no color change is observed for untreated glass biosensors.

The absorbance at 495 nm of the solution after perchloric acid treatment following the above procedure can be used as an indicator of the quantity of amine groups on the surface. In one set of experiment, the absorbance was 0.627, 0.647, and 0.728 for Sigma slides, Cel-Associate slides, and in-house biosensor slides, respectively. This indicates that the level of NH$_2$ activation of the biosensor surface is comparable in the activation commercially available microarray glass slides.

After following the above protocol for activating the biosensor with amine, a linker molecule can be attached to the biosensor. When selecting a cross-linking reagent, issues such as selectivity of the reactive groups, spacer arm length, solubility, and cleavability should be considered. The linker molecule, in turn, binds the specific binding substance that is used for specific recognition of a binding partner. As an example, the protocol below has been used to bind a biotin linker molecule to the amine-activated biosensor.

Protocol for Activating Amine-Coated Biosensor with Biotin

Wash an amine-coated biosensor with PBS (pH 8.0) three times. Prepare sulfo-succinimidyl-6-(biotinamido)hexanoate (sulfo-NHS-LC-biotin, Pierce, Rockford, Ill.) solution in PBS buffer (pH 8) at 0.5 mg/ml concentration. Add 2 ml of the sulfo-NHS-LC-biotin solution to each amine-coated biosensor and incubate at room temperature for 30 min. Wash the biosensor three times with PBS (pH 8.0). The sulfo-NHS-LC-biotin linker has a molecular weight of 556.58 and a length of 22.4 Å. The resulting biosensors can be used for capturing avidin or strepavidin molecules.

Protocol for Activating Amine-Coated Biosensor with Aldehyde

Prepare 2.5% glutaraldehyde solution in 0.1 M sodium phosphate, 0.05% sodium azide, 0.1% sodium cyanoborohydride, pH 7.0. Add 2 ml of the sulfo-NHS-LC-biotin solution to each amine-coated biosensor and incubate at room temperature for 30 min. Wash the biosensor three times with PBS (pH 7.0). The glutaraldehyde linker has a molecular weight of 100.11. The resulting biosensors can be used for binding proteins and other amine-containing molecules. The reaction proceeds through the formation of Schiff bases, and subsequent reductive amination yields stable secondary amine linkages. In one experiment, where a coated aldehyde slide made by the inventors was compared to a commercially available aldehyde slide (Cel-Associate), ten times higher binding of streptavidin and anti-rabbit IgG on the slide made by the inventors was observed.

Protocol for Activating Amine-coated Biosensor with NHS 25 mM N,N'-disuccinimidyl carbonate (DSC, Sigma Chemical Company, St. Louis, Mo.) in sodium carbonate buffer (pH 8.5) was prepared. 2 ml of the DSC solution was added to each amine-coated biosensor and incubated at room temperature for 2 hours. The biosensors were washed three times with PBS (pH 8.5). A DSC linker has a molecular weight of 256.17. Resulting biosensors are used for binding to hydroxyl- or amine-containing molecules. This linker is one of the smallest homobifunctional NHS ester cross-linking reagents available.

In addition to the protocols defined above, many additional surface activation and molecular linker techniques have been reported that optimize assay performance for different types of biomolecules. Most common of these are amine surfaces, aldehyde surfaces, and nickel surfaces. The activated surfaces, in turn, can be used to attach several different types of chemical linkers to the biosensor surface, as shown in Table 2. While the amine surface is used to attach several types of linker molecules, the aldehyde surface is used to bind proteins directly, without an additional linker. A nickel surface is used exclusively to bind molecules that have an incorporated histidine ("his") tag. Detection of "his-tagged" molecules with a Nickel activated surface is well known (Sigal et al., *Anal. Chem.* 68, 490 (1996)).

Table 2 demonstrates an example of the sequence of steps that are used to prepare and use a biosensor, and various options that are available for surface activation chemistry, chemical linker molecules, specific binding substances and binding partners molecules. Opportunities also exist for enhancing detected signal through amplification with larger molecules such as HRP or streptavidin and the use of polymer materials such as dextran or TSPS to increase surface area available for molecular binding.

EXAMPLE 9

IgG Assay

Figure 37A:
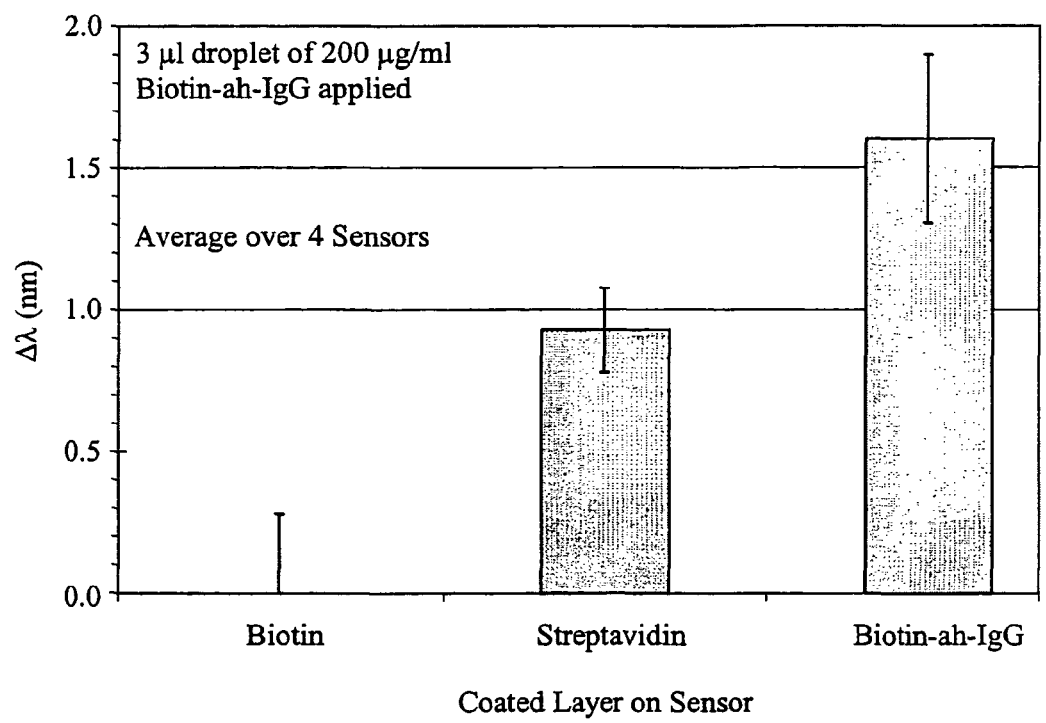
FIGS. 37A-B.
Figure 37B:
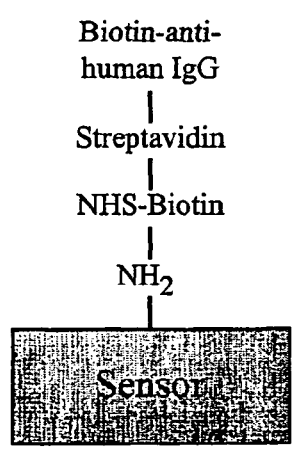

As an initial demonstration for detection of biochemical binding, an assay was performed in which a biosensor was prepared by activation with the amino surface chemistry described in Example 8 followed by attachment of a biotin linker molecule. The biotin linker is used to covalently bond a streptavidin receptor molecule to the surface by exposure to a 50 µg/ml concentration solution of streptavidin in PBS at room temperature for 2-4 hours. The streptavidin receptor is capable of binding any biotinylated protein to the biosensor surface. For this example, 3 µl droplets of biotinylated anti-human IgG in phosphate buffer solution (PBS) were deposited onto 4 separate locations on the biosensor surface at a concentration of 200 µg/ml. The solution was allowed to incubate on the biosensor for 60 min before rinsing thoroughly with PBS. The peak resonant wavelength of the 4 locations were measured after biotin activation, after streptavidin receptor application, and after ah-IgG binding. FIG. 37 shows that the addition of streptavidin and ah-IgG both yield a clearly measurable increase in the resonant wavelength.

EXAMPLE 10

Biotin/Streptavidin Assay

Figure 38A:
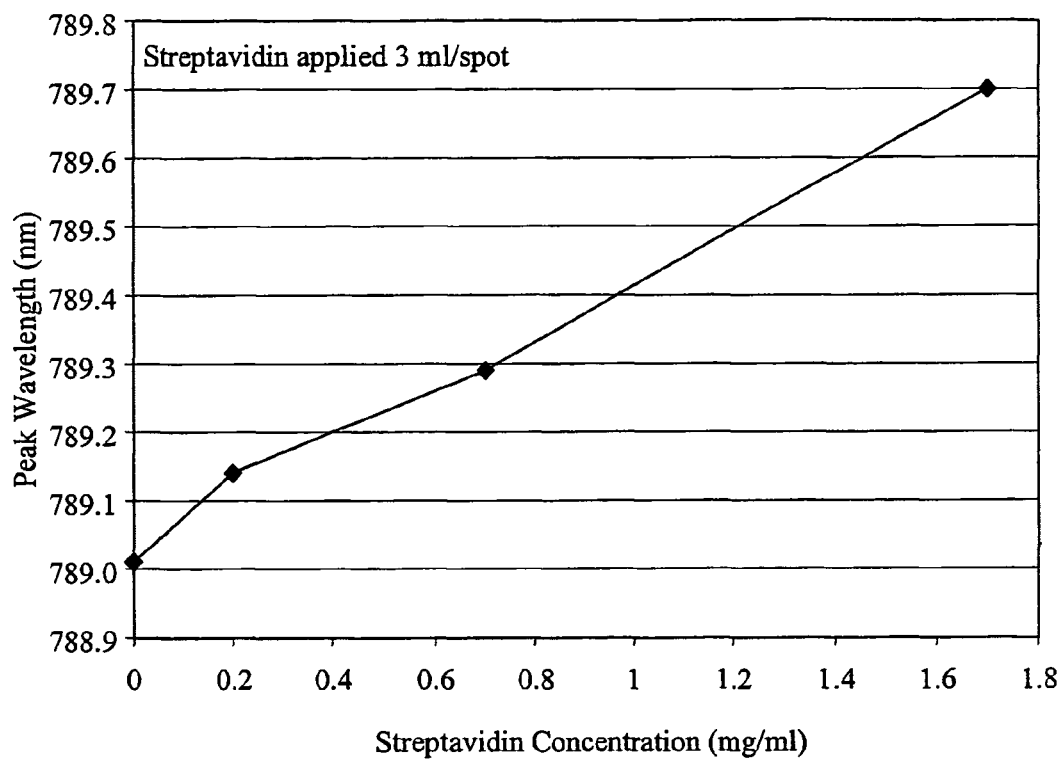
FIGS. 38A-B.
Figure 38B:
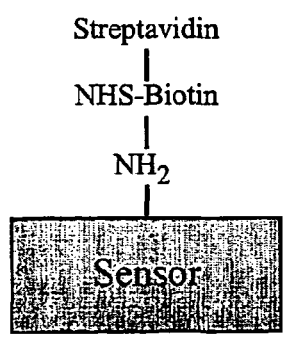

A series of assays were performed to detect streptavidin binding by a biotin receptor layer. A biosensor was first activated with amino chemistry, followed by attachment of a NHS-Biotin linker layer, as previously described. Next, 3 µl droplets of streptavidin in PBS were applied to the biosensor at various concentrations. The droplets were allowed to incubate on the biosensor surface for 30 min before thoroughly washing with PBS rinsing with DI water. The peak resonant wavelength was measured before and after streptavidin binding, and the resonant wavelength shifts are shown in FIG. 38. A linear relationship between peak wavelength and streptavidin concentration was observed, and in this case the lowest streptavidin concentration measured was 0.2 µg/ml. This concentration corresponds to a molarity of 3.3 nM.

EXAMPLE 11

Protein-Protein Binding Assay

An assay was performed to demonstrate detection of protein-protein interactions. As described previously, a biosensor was activated with amino chemistry and an NHS-biotin linker layer. A goat anti-biotin antibody receptor layer was attached to the biotin linker by exposing the biosensor to a 50 µg/ml concentration solution in PBS for 60 min at room temperature followed by washing in PBS and rinsing with DI

TABLE 2

Figure 39A:
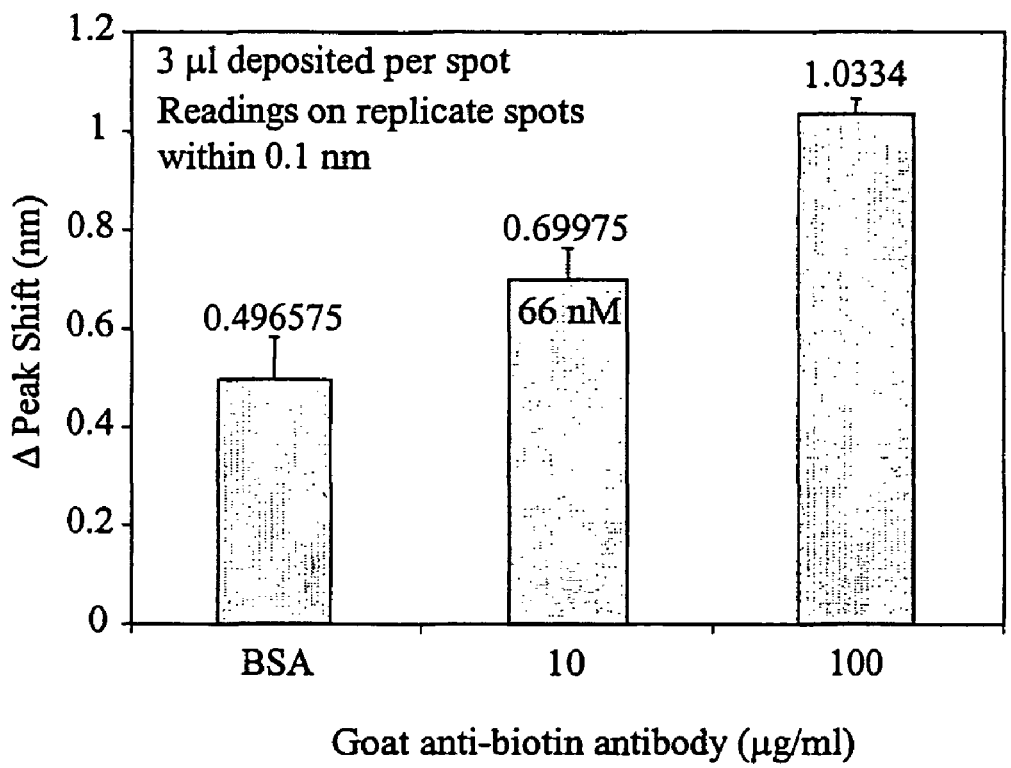
FIGS. 39A-B.
Figure 39B:
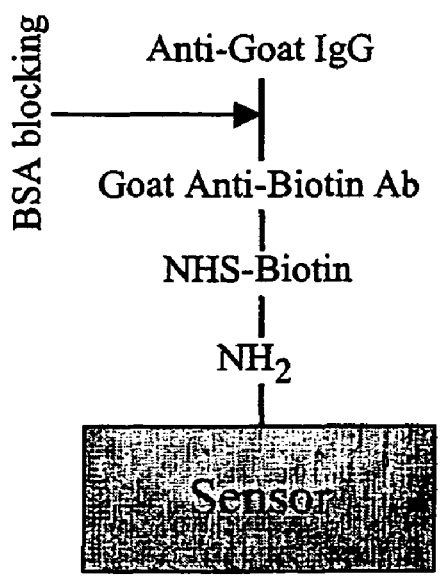

| Bare Sensor | Surface Activation | Linker Molecule | Receptor Molecule | Detected Material | Label Molecule (Optional) |
|---|---|---|---|---|---|
| Glass | Amino | SMPT | Sm m'cules | Peptide | Enhance sensitivity |
| Polymers optional to enhance sensitivity | Aldehyde | NHS-Biotin DMP NNDC | Peptide Med Protein Lrg Protein · IgG | Med Protein Lrg Protein · IgG Phage | 1000 × HRP Streptavidin |
| 2-5 × Dextran | Ni | His-tag | | Cell | |
| TSPS | | Others . . . | cDNA | cDNA | | water. In order to prevent interaction of nonspecific proteins with unbound biotin on the biosensor surface, the biosensor surface was exposed to a 1% solution of bovine serum albumin (BSA) in PBS for 30 min. The intent of this step is to "block" unwanted proteins from interacting with the biosensor. As shown in FIG. 39 a significant amount of BSA is incorporated into the receptor layer, as shown by the increase in peak wavelength that is induced. Following blocking, 3 µl droplets of various concentrations of anti-goat IgG were applied to separate locations on the biosensor surface. The droplets were allowed to incubate for 30 min before thorough rinsing with DI water. The biosensor peak resonant wavelength was measured before blocking, after blocking, after receptor layer binding, and after anti-goat IgG detection for each spot. FIG. 39 shows that an anti-goat IgG concentration of 10 µg/ml yields an easily measurable wavelength shift.

EXAMPLE 12

Unlabeled ELISA Assay

Figure 40A:
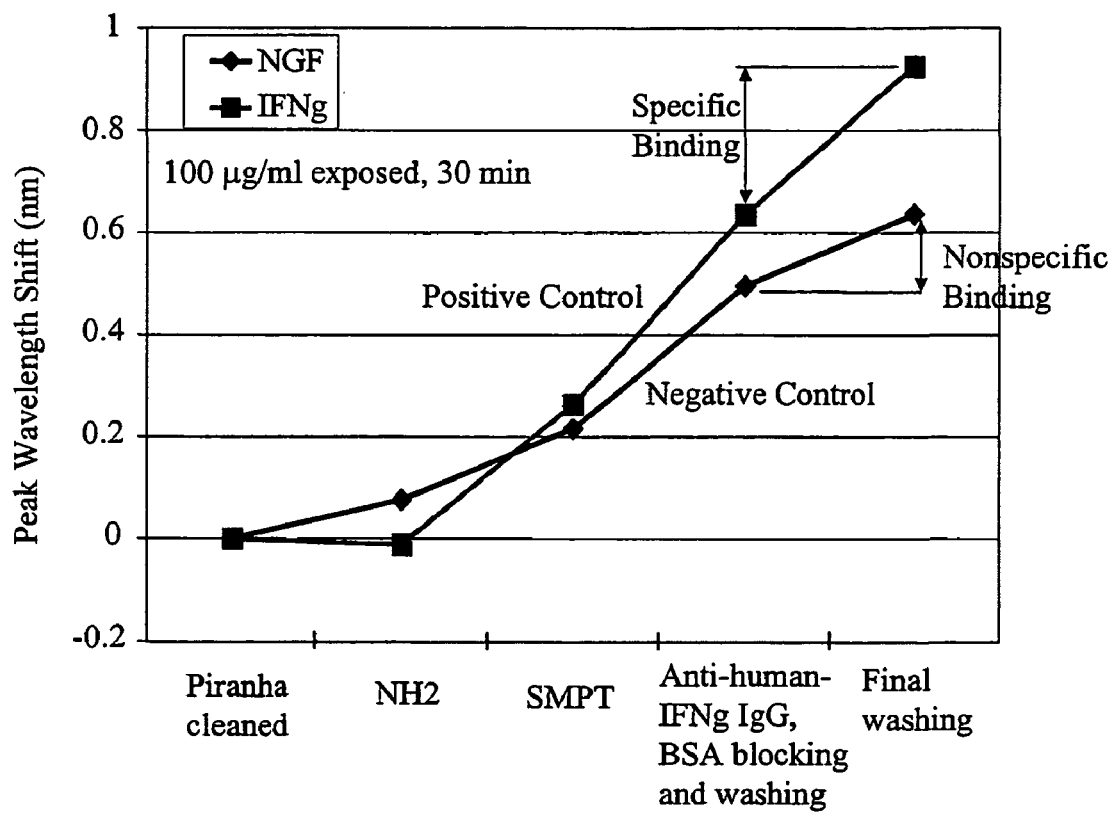
FIGS. 40A-B.
Figure 40B:
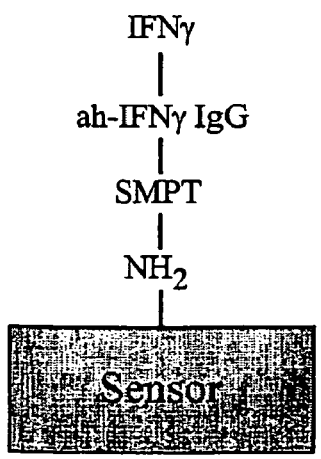

Another application of a biosensor array platform is its ability to perform Enzyme-Linked Immunosorbent Assays (ELISA) without the need for an enzyme label, and subsequent interaction an enzyme-specific substrate to generate a colored dye. FIG. 40 shows the results of an experiment where a biosensor was prepared to detect interferon-γ (IFN-γ) with an IFN-γ antibody receptor molecule. The receptor molecule was covalently attached to an $NH_2$-activated biosensor surface with an SMPT linker molecule (Pierce Chemical Company, Rockford, Ill.). The peak resonant wavelength shift for application of the $NH_2$, SMPT, and anti-human IFN-α receptor molecules were measured for two adjacent locations on the biosensor surface, as shown in FIG. 40. The two locations were exposed to two different protein solutions in PBS at a concentration of 100 µg/ml. The first location was exposed to IFN-γ, which is expected to bind with the receptor molecule, while the second was exposed to neural growth factor (NGF), which is not expected to bind with the receptor. Following a 30 minute incubation the biosensor was measured by illuminating from the bottom, while the top surface remained immersed in liquid. The location exposed to IFN-γ registered a wavelength shift of 0.29 nm, while the location exposed to NGF registered a wavelength shift of only 0.14 nm. Therefore, without the use of any type of enzyme label or color-generating enzyme reaction, the biosensor was able to discriminate between solutions containing different types of protein.

EXAMPLE 13

Protease Inhibitor Assay (Caspase-3)

A Caspase-3 protease inhibitor assay was performed to demonstrate the biosensor's ability to measure the presence and cleavage of small molecules in an experimental context that is relevant to pharmaceutical compound screening.

Caspases (Cysteine-requiring Aspartate protease) are a family of proteases that mediate cell death and are important in the process of apoptosis. Caspase 3, an effector caspase, is the most studied of mammalian caspases because it can specifically cleave most known caspase-related substrates. The caspase 3 assay is based on the hydrolysis of the 4-amino acid peptide substrate NHS-Gly-Asp-Glu-Val-Asp p-nitroanilide (NHS-GDEVD-pNA) by caspase 3, resulting in the release of the pNA moiety.

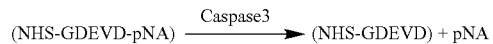

The NHS molecule attached to the N-terminal of the GDEVD provides a reactive end group to enable the NHS-GDEVD-pNA complex to be covalently bound to the biosensor with the pNA portion of the complex oriented away from the surface. Attached in this way, the caspase-3 will have the best access to its substrate cleavage site.

A biosensor was prepared by cleaning in 3:1 $H_2SO_4:H_2O_2$ solution (room temperature, 1 hour), followed by silanation (2% silane in dry acetone, 30 sec) and attachment of a polyphelysine (PPL) layer (100 µg/ml PPL in PBS pH 6.0 with 0.5 M NaCl, 10 hours). The NHS-GDEVD-pNA complex was attached by exposing the biosensor to a 10 mM solution in PBS (pH 8.0, room temperature, 1 hour). A microwell chamber was sealed over the biosensor surface, and cleavage of pNA was performed by addition of 100 µl of caspase-3 in 1× enzyme buffer (100 ng/ml, room temperature, 90 minutes). Following exposure to the caspase 3 solution, the biosensor was washed in PBS. A separate set of experiments using a spectrophotometer were used to confirm the attachment of the complex to the surface of the biosensor, and functional activity of the caspase-3 for removal of the pNA molecule from the surface-bound complex.

Figure 41A:
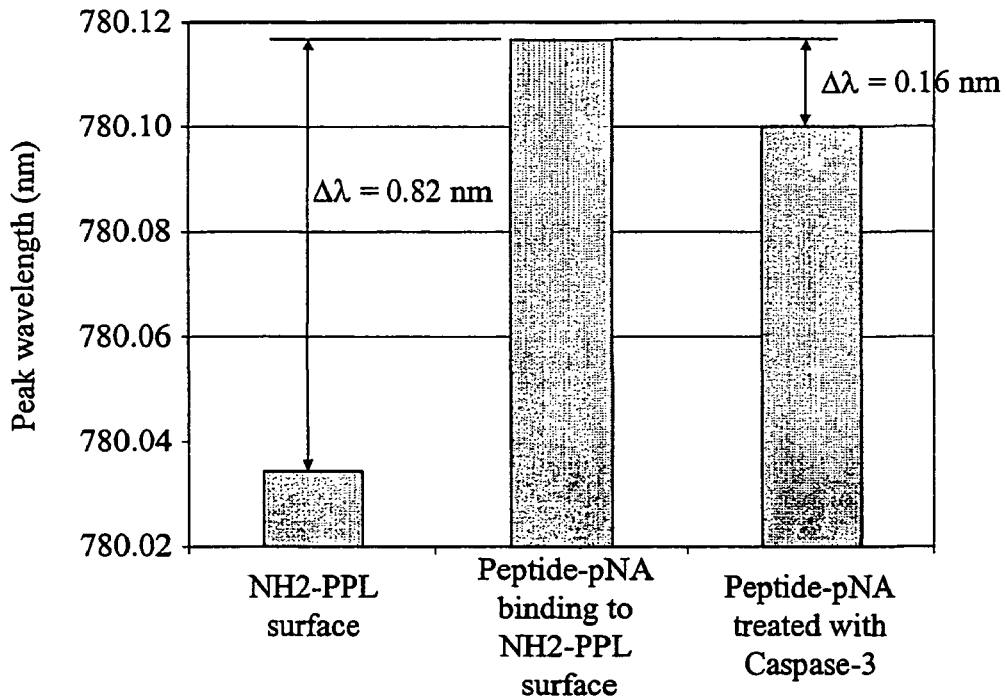
FIGS. 41A-B.
Figure 41B:
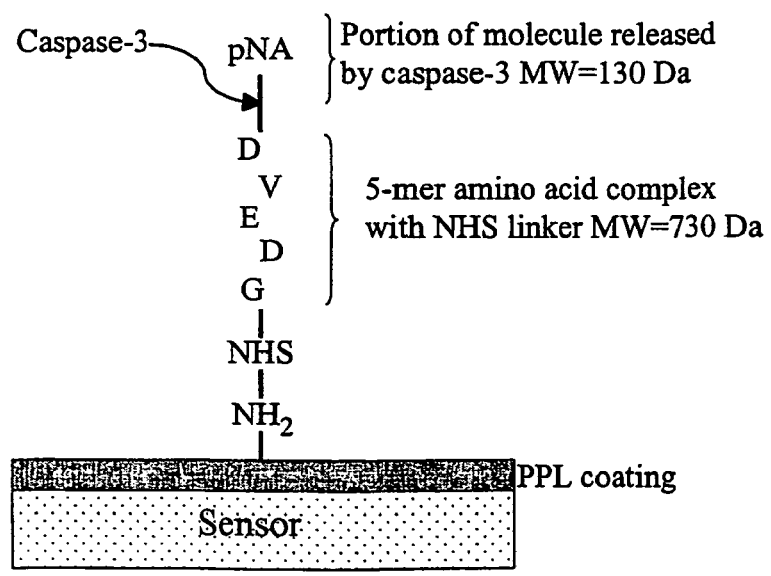

The peak resonant frequency of the biosensor was measured before attachment of the NHS-GDEVD-pNA complex, after attachment of the complex (MW=860 Da), and after cleavage of the pNA (MW=136) with caspase 3. As shown in FIG. 41, the attachment of the peptide molecule is clearly measurable, as is the subsequent removal of the pNA. The pNA removal signal of Δλ=0.016 nm is 5.3× higher than the minimum detectable peak wavelength shift of 0.003 nm. The proportion of the added molecular weight and subtracted molecular weight (860 Da/136 Da=6.32) are in close agreement with the proportion of peak wavelength shift observed for the added and subtracted material (0.082 nm/0.016 nm=5.14).

The results of this experiment confirm that a biosensor is capable of measuring small peptides (in this case, a 5-mer peptide) without labels, and even detecting the removal of 130 Da portions of a molecule through the activity of an enzyme.

EXAMPLE 14

Reaction Kinetics for Protein-Protein Binding Assays

Figure 42A:
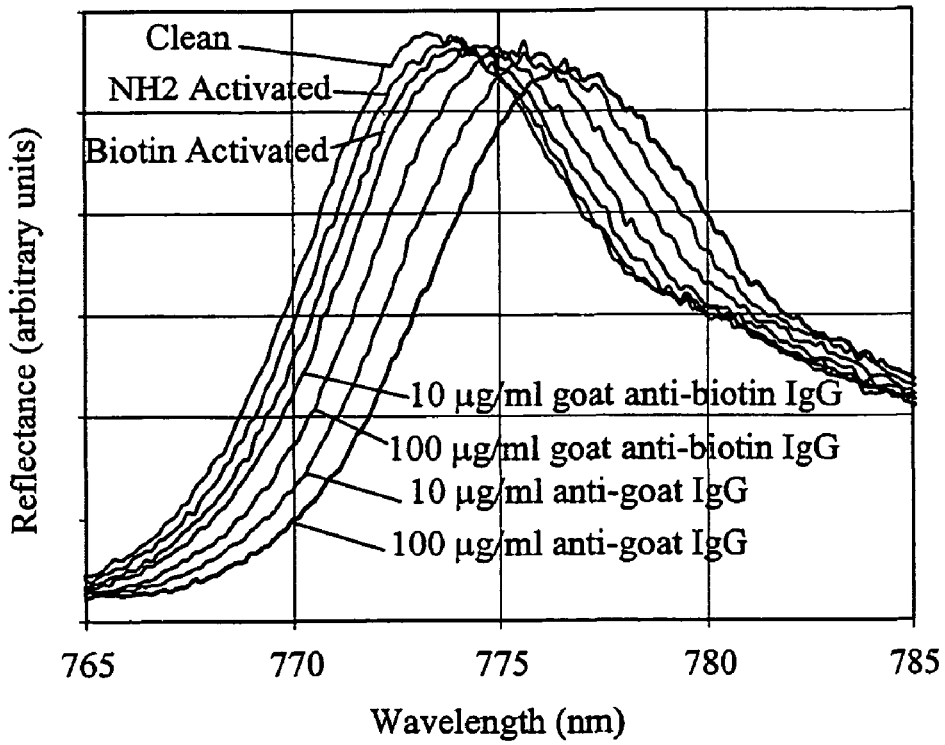
FIGS. 42A-B.
Figure 42B:
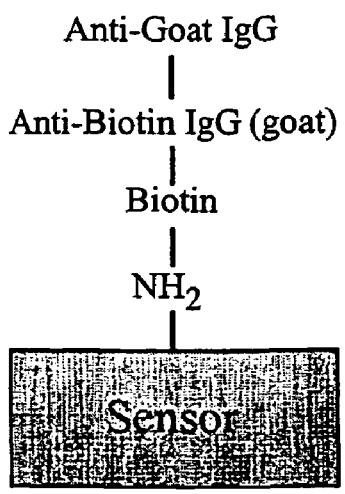

Because a biosensor of the invention can be queried continuously as a function of time while it is immersed in liquid, a biosensor can be utilized to perform both endpoint-detection experiments and to obtain kinetic information about biochemical reactions. As an example, FIG. 42 shows the results of an experiment in which a single biosensor location is measured continuously through the course of consecutively adding various binding partners to the surface. Throughout the experiment, a detection probe illuminated the biosensor through the back of the biosensor substrate, while biochemistry is performed on the top surface of the device. A rubber gasket was sealed around the measured biosensor location so that added reagents would be confined, and all measurements were performed while the top surface of the biosensor was immersed in buffer solution. After initial cleaning, the biosensor was activated with $NH_2$, and an NHS-Biotin linker molecule. As shown in FIG. 42, goat α-biotin antibodies of several different concentrations (1, 10, 100, 1000 µg/ml) were consecutively added to the biosensor and allowed to incubate for 30 minutes while the peak resonant wavelength was monitored. Following application of the highest concentration α-Biotin IgG, a second layer of protein was bound to the biosensor surface through the addition of α-goat IgG at several concentrations (0.1, 1, 10, and 100 µg/ml). Again, the resonant peak was continuously monitored as each solution was allowed to incubate on the biosensor for 30 minutes. FIG. 42 shows how the resonant peak shifted to greater wavelength at the end of each incubation period.

Figure 43A:
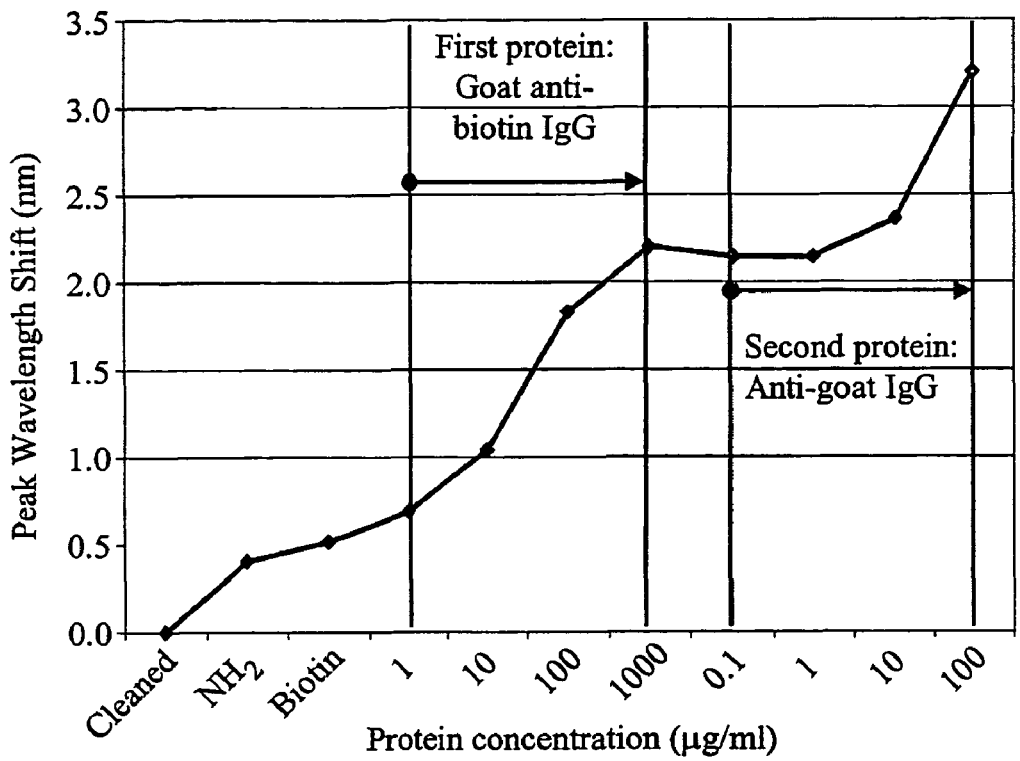
FIGS. 43A-B.
Figure 43B:
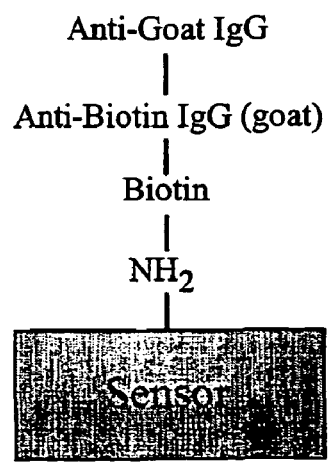
Figure 44A:
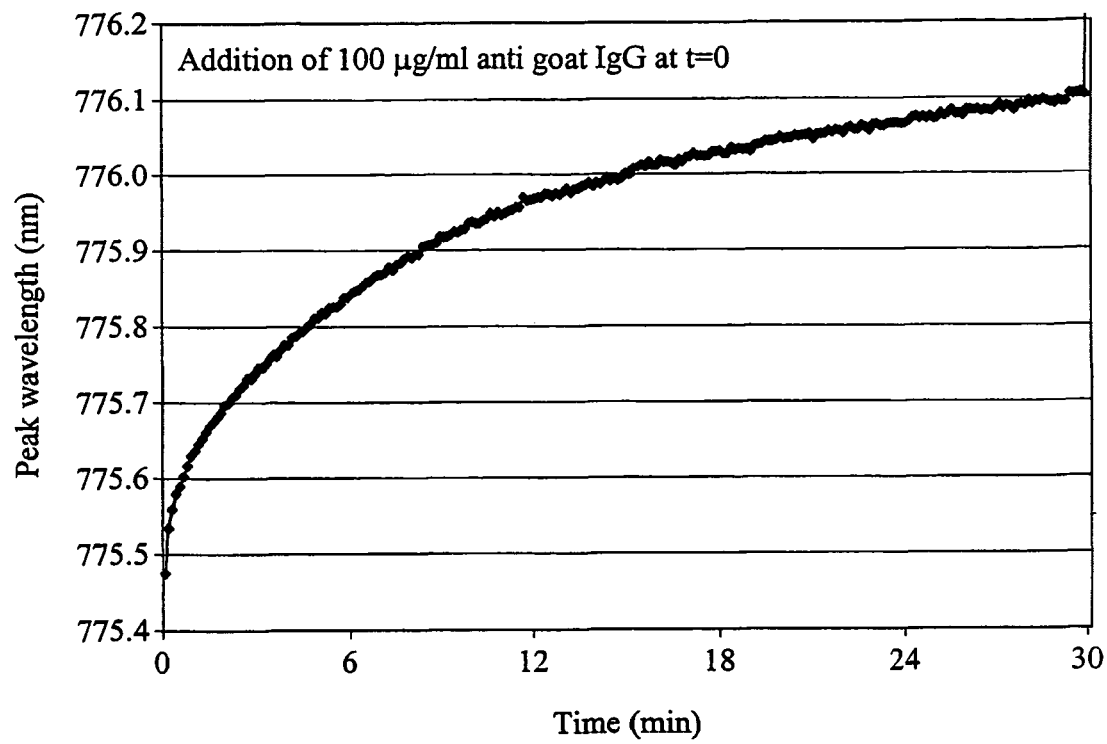
FIGS. 44A-B.
Figure 44B:
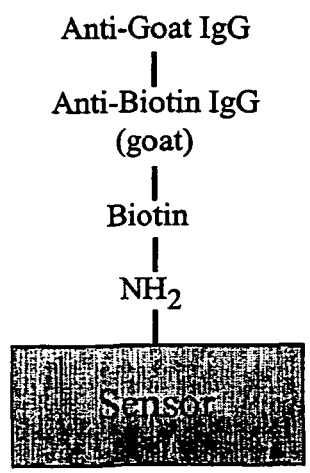

FIG. 43 shows the kinetic binding curve for the final resonant peak transitions from FIG. 42, in which 100 µg/ml of α-goat IgG is added to the biosensor. The curve displays the type of profile that is typically observed for kinetic binding experiments, in which a rapid increase from the base frequency is initially observed, followed by a gradual saturation of the response. This type of reaction profile was observed for all the transitions measured in the experiment. FIG. 44 shows the kinetic binding measurement of IgG binding.

Figure 45A:
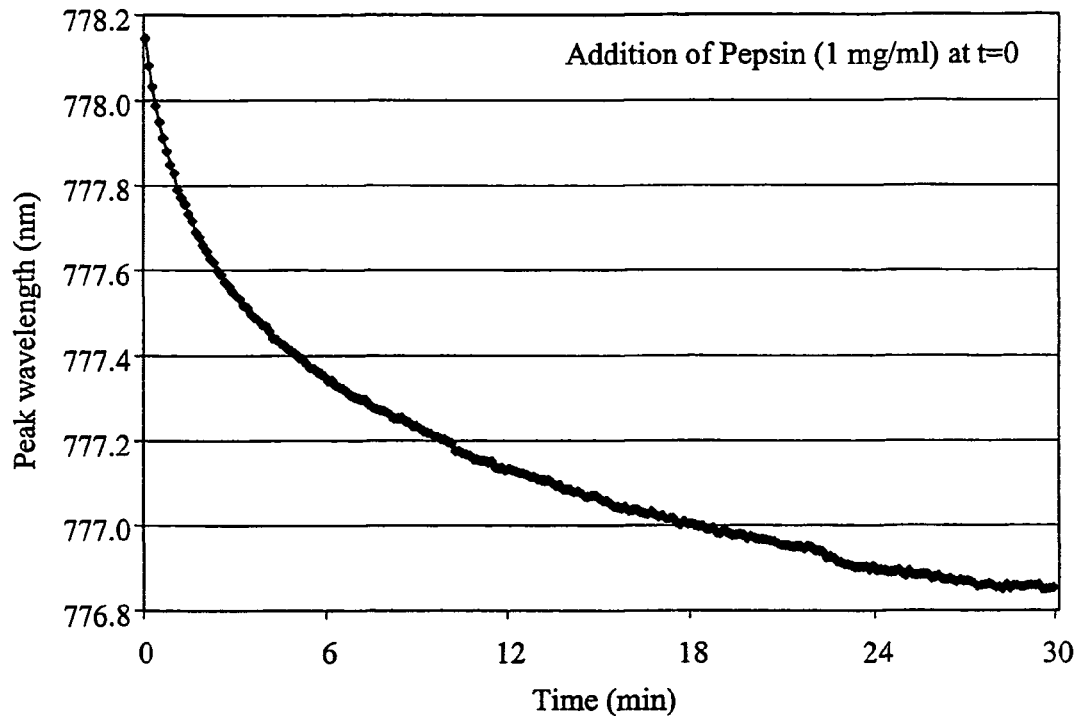
FIGS. 45A-B.
Figure 45B:
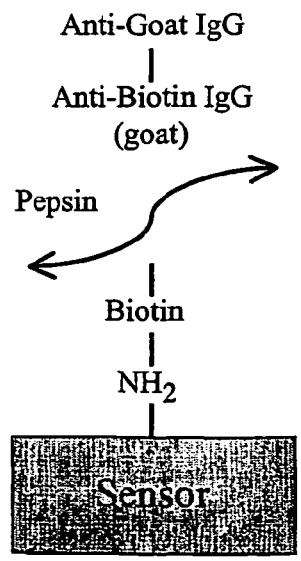

The removal of material from the biosensor surface through the activity of an enzyme is also easily observed. When the biosensor from the above experiment (with two protein coatings of goat anti-biotin IgG and anti-goat IgG) is exposed to the protease pepsin at a concentration of 1 mg/ml, the enzyme dissociates both IgG molecules, and removes them from the biosensor surface. As shown in FIG. 45, the removal of bound molecules from the surface can be observed as a function of time.

EXAMPLE 15

Proteomics Applications

Biosensors of the invention can be used for proteomics applications. A biosensor array can be exposed to a test sample that contains a mixture of binding partners comprising, for example, proteins or a phage display library, and then the biosensor surface is rinsed to remove all unbound material. The biosensor is optically probed to determine which distinct locations on the biosensor surface have experienced the greatest degree of binding, and to provide a quantitative measure of bound material. Next, the biosensor is placed in a "flow cell" that allows a small (e.g., <50 microliters) fixed volume of fluid to make contact to the biosensor surface. One electrode is activated so as to elute bound material from only a selected biosensor array distinct location. The bound material becomes diluted within the flow cell liquid. The flow cell liquid is pumped away from the biosensor surface and is stored within a microtiter plate or some other container. The flow cell liquid is replaced with fresh solution, and a new biosensor electrode is activated to elute its bound binding partners. The process is repeated until all biosensor distinct locations of interest have been eluted and gathered into separate containers. If the test sample liquid contained a mixture of proteins, protein contents within the separate containers can be analyzed using a technique such as electrospray tandem mass spectrometry. If the sample liquid contained a phage display library, the phage clones within the separate containers can be identified through incubation with a host strain bacteria, concentration amplification, and analysis of the relevant library DNA sequence.

EXAMPLE 16

Mathematical Resonant Peak Determination

This example discusses some of the findings that have been obtained from looking at fitting different types of curves to the observed data.

The first analytic curve examined is a second-order polynomial, given by $$y = ax^2 + bx + c$$

The least-squares solution to this equation is given by the cost function $$\phi = \sum_{i=1}^{n} (ax_i^2 + bx_i + c - y_i)^2,$$

the minimization of which is imposed by the constraints $$\frac{\partial \phi}{\partial a} = \frac{\partial \phi}{\partial b} = \frac{\partial \phi}{\partial c} = 0.$$

Solving these constraints for a, b, and c yields $$\begin{pmatrix} a \\ b \\ c \end{pmatrix} = \begin{pmatrix} \sum x_i^4 & \sum x_i^3 & \sum x_i^2 \\ \sum x_i^3 & \sum x_i^2 & \sum x_i \\ \sum x^2 & \sum x_i & n \end{pmatrix}^{-1} \cdot \begin{pmatrix} \sum x_i^2 y_i \\ \sum x_i y_i \\ \sum y_i \end{pmatrix}.$$

Figure 46:
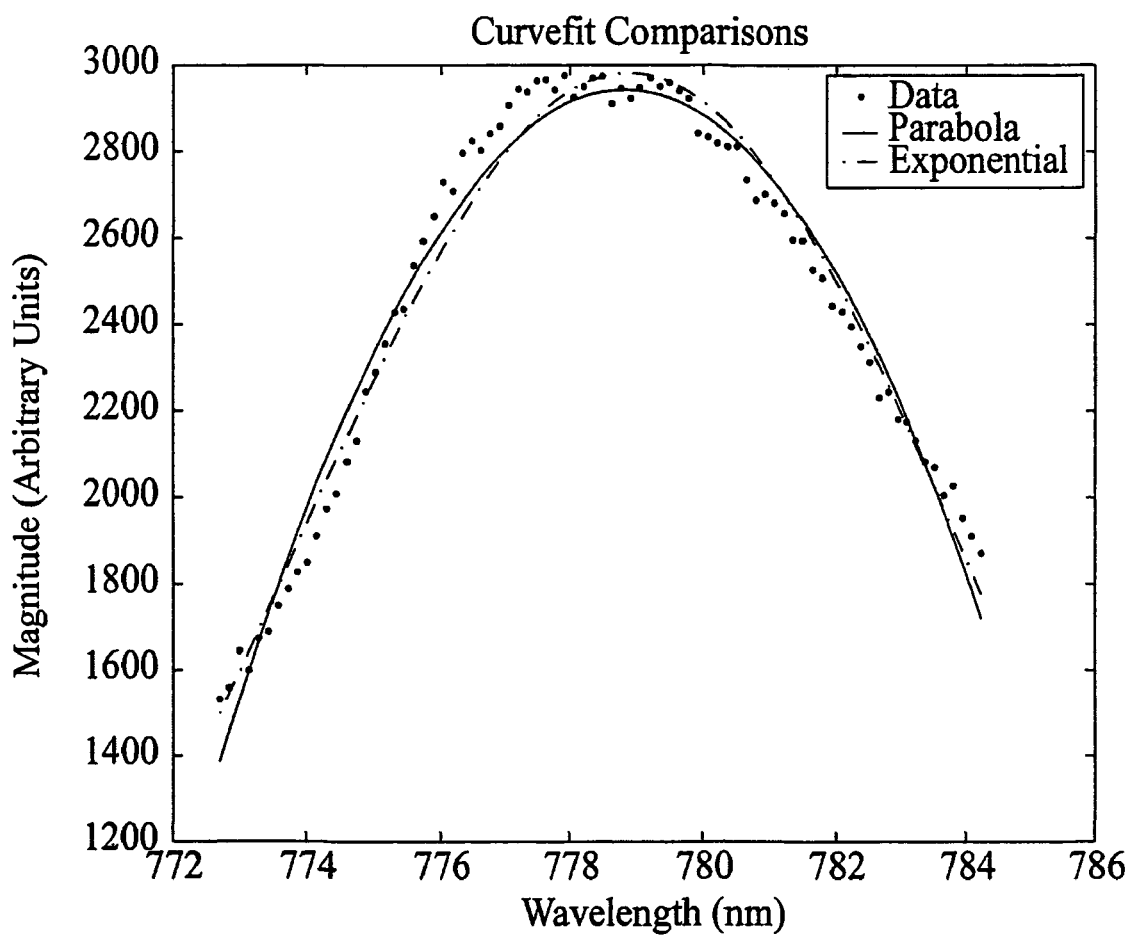
FIG. 46 shows comparison of mathematical fit of parabolic and exponential functions to spectrometer data from a resonant peak. The exponential curve fit is used to mathematically determine a peak resonant wavelength.

The result of one such fit is shown in FIG. 46; the acquired data are shown as dots and the $2^{nd}$-order polynomial curve fit is shown as the solid line.

Empirically, the fitted curve does not appear to have sufficient rise and fall near the peak. An analytic curve that provides better characteristics in this regard is the exponential, such as a Gaussian. A simple method for performing a Gaussian-like fit is to assume that the form of the curve is given by $$y = e^{ax^2 + bx + c},$$

in which case the quadratic equations above can be utilized by forming y', where y'=lny. FIG. 46 shows the result of such a fit. The visual appearance of FIG. 46 indicates that the exponential is a better fit, providing a 20% improvement over that of the quadratic fit.

Assuming that the exponential curve is the preferred data fitting method, the robustness of the curve fit is examined in two ways: with respect to shifts in the wavelength and with respect to errors in the signal amplitude.

To examine the sensitivity of the analytical peak location when the window from which the curve fitting is performed is altered to fall 10 sampling intervals to the left or to the right of the true maxima. The resulting shift in mathematically-determined peak location is shown in Table 3. The conclusion to be derived is that the peak location is reasonably robust with respect to the particular window chosen: for a shift of ~1.5 nm, the corresponding peak location changed by only <0.06 nm, or 4 parts in one hundred million sensitivity.

To examine the sensitivity of the peak location with respect to noise in the data, a signal free of noise must be defined, and then incremental amounts of noise is added to the signal and the impact of this noise on the peak location is examined. The ideal signal, for purposes of this experiment, is the average of 10 resonant spectra acquisitions.

Figure 47:
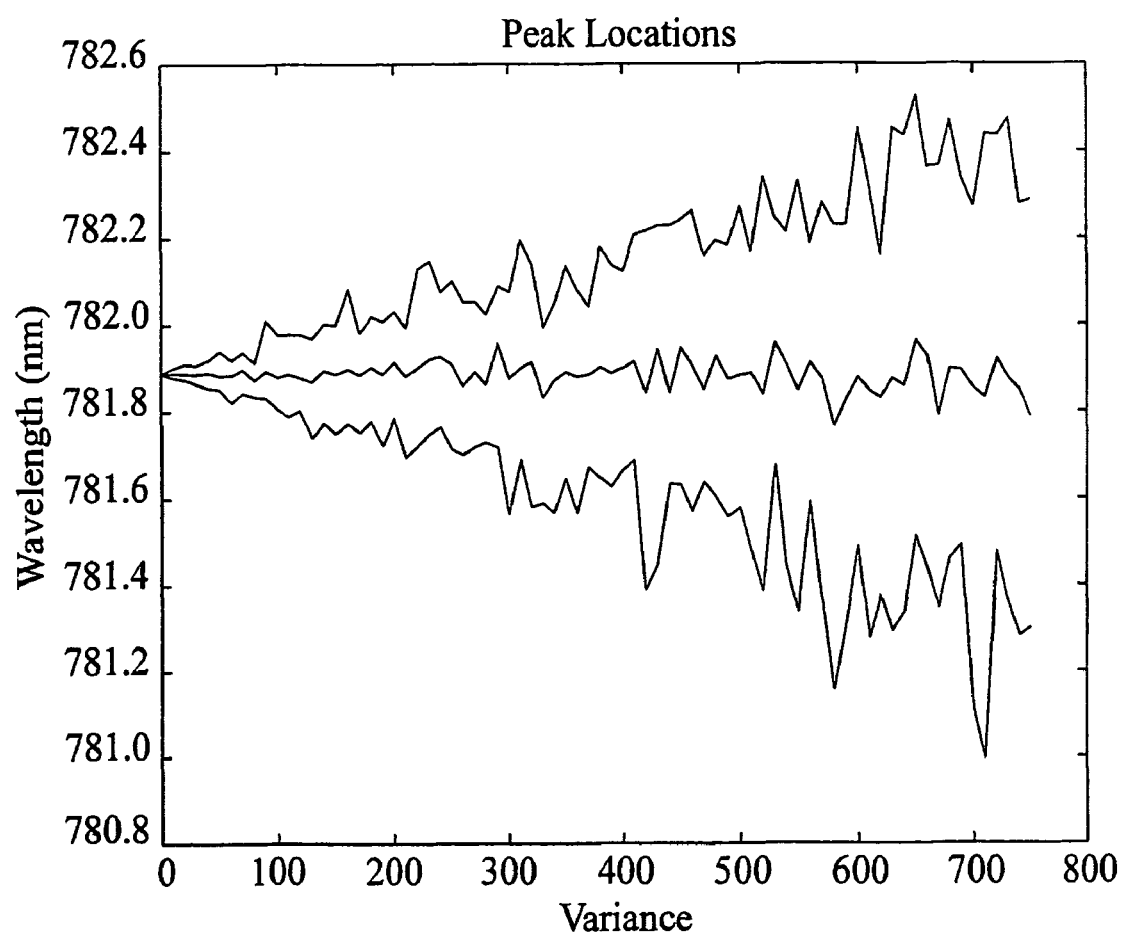
FIG. 47 shows sensitivity of the mathematically determined peak resonant wavelength to artificially added noise in the measured spectrum.

Gaussian noise of varying degrees is superimposed on the ideal signal. For each such manufactured noisy signal, the peak location is estimated using the $2^{nd}$-order exponential curve fit. This is repeated 25 times, so that the average, maximum, and minimum peak locations are tabulated. This is repeated for a wide range of noise variances—from a variance of 0 to a variance of 750. The result is shown in FIG. 47.

TABLE 3

Comparison of peak location as a function of window location

| Shift | Window | Peak Location |
|---|---|---|
| Δ = −10 bins | 771.25-782.79 nm | 778.8221 nm |
| Δ = 0 bins | 772.70-784.23 nm | 778.8887 nm |
| Δ = +10 bins | 774.15-785.65 nm | 7778.9653 nm |

The conclusion of this experiment is that the peak location estimation routine is extremely robust to noisy signals. The entire range of peak locations in FIG. 47 is only 1.5 nm, even with as much random noise variance of 750 superimposed—an amount of noise that is substantially greater that what has been observed on the biosensor thus far. The average peak location, despite the level of noise, is within 0.1 nm of the ideal location.

Based on these results, a basic algorithm for mathematically determining the peak location of a colorimetric resonant biosensor is as follows:

1. Input data $x_i$ and $y_i$, i=1, . . . ,n
2. Find maximum
    a. Find k such that $y_k \geq y_i$ for all i≠k
3. Check that maximum is sufficiently high
    a. Compute mean $\bar{y}$ and standard deviation σ of sample
    b. Continue only if $(y_k-\bar{y})/\sigma >$ User Threshold
4. Define curve-fit region of 2w+1 bins (w defined by the user)
    a. Extract $x_i$, k−w≦i≦k+w
    b. Extract $y_i$, k−w≦i≦k+w
5. Curve fit
    a. $g_i = \ln y_i$
    b. Perform $2^{nd}$-order polynomial fit to obtain $g_i$ defined on $x_i$, k−w≦i≦k+w
    c. Polynomial fit returns coefficients a,b,c of form $ax^2+bx+c$
    d. Exponentiate: $y'_i = e^{g'_i}$
6. Output
    a. Peak location p given by $x_p=-b/2a$
    b. Peak value given by $y'_p(x_p)$ In summary, a robust peak determination routine has been demonstrated; the statistical results indicate significant insensitivity to the noise in the signal, as well as to the windowing procedure that is used. These results lead to the conclusion that, with reasonable noise statistics, that the peak location can be consistently determined in a majority of cases to within a fraction of a nm, perhaps as low as 0.1 to 0.05 nm.

EXAMPLE 17

Homogenous Assay Demonstration

An SWS biosensor detects optical density of homogenous fluids that are in contact with its surface, and is able to differentiate fluids with refractive indices that differ by as little as $\Delta n = 4 \times 10^{-5}$. Because a solution containing two free non-interacting proteins has a refractive index that is different from a solution containing two bound interacting proteins, an SWS biosensor can measure when a protein-protein interaction has occurred in solution without any kind of particle tag or chemical label.

Three test solutions were prepared for comparison:
1. Avidin in Phosphate Buffer Solution (PBS), (10 µg/ml)
2. Avidin (10 µg/ml)+Bovine Serum Albumin (BSA) (10 µg/ml) in PBS
3. Avidin (10 µg/ml)+Biotinylated BSA (b-BSA) (10 µg/ml) in PBS A single SWS sensor was used for all measurements to eliminate any possibility of cross-sensor bias. A 200 µl sample of each test solution was applied to the biosensor and allowed to equilibrate for 10 minutes before measurement of the SWS biosensor peak resonant wavelength value. Between samples, the biosensor was thoroughly washed with PBS.

Figure 51:
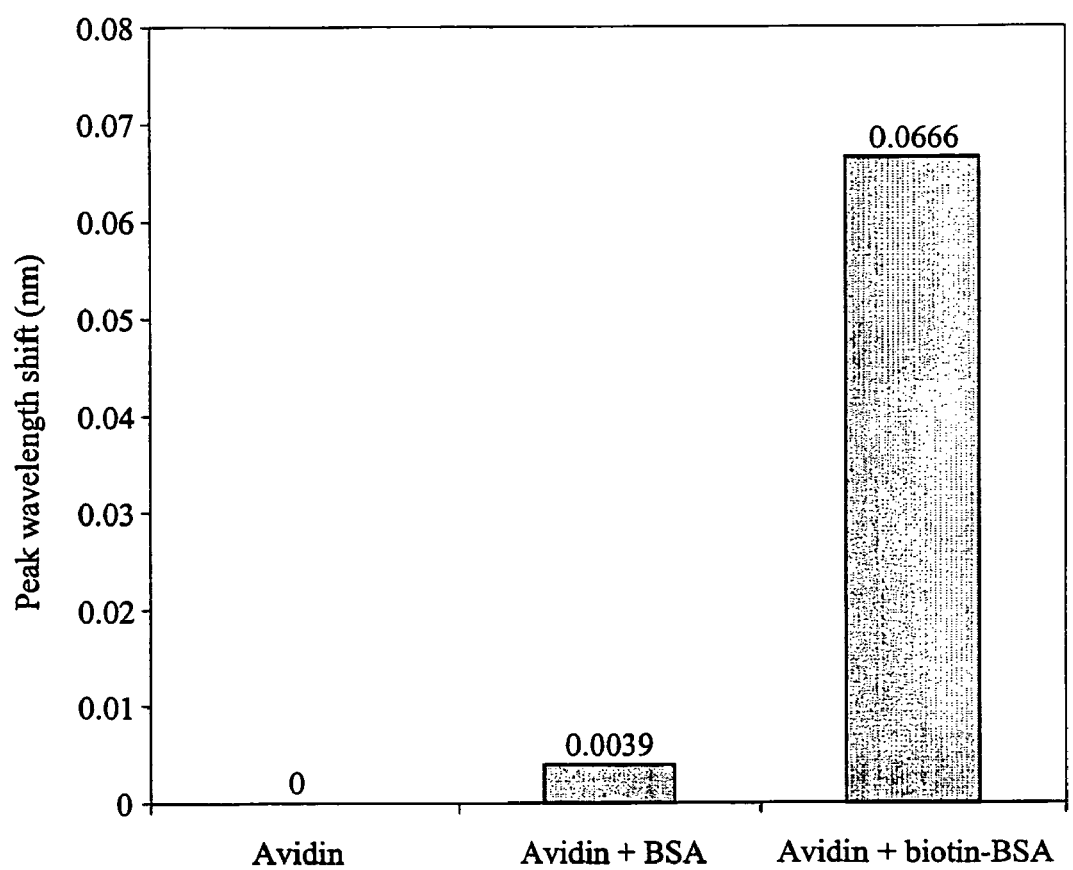
FIG. 51 shows a plot of the peak resonant wavelength values for test solutions. The avidin solution was taken as the baseline reference for comparison to the Avidin+BSA and Avidin+b-BSA solutions. Addition of BSA to avidin results in only a small resonant wavelength increase, as the two proteins are not expected to interact. However, because biotin and avidin bind strongly ($Kd=10^{-15}M$), the avidin+b-BSA solution will contain larger bound protein complexes. The peak resonant wavelength value of the avidin+b-BSA solution thus provides a large shift compared to avidin+BSA.

The peak resonant wavelength values for the test solutions are plotted in FIG. 51. The avidin solution was taken as the baseline reference for comparison to the Avidin+BSA and Avidin+b-BSA solutions. Addition of BSA to avidin results in only a small resonant wavelength increase, as the two proteins are not expected to interact. However, because biotin and avidin bind strongly (Kd=$10^{-15}$M), the avidin+b-BSA solution will contain larger bound protein complexes. The peak resonant wavelength value of the avidin+b-BSA solution thus provides a large shift compared to avidin+BSA.

The difference in molecular weight between BSA (MW=66 KDa) and b-BSA (MW=68 KDa) is extremely small. Therefore, the differences measured between a solution containing non-interacting proteins (avidin+BSA) and interacting proteins (avidin+b-BSA) are attributable only to differences in binding interaction between the two molecules. The bound molecular complex results in a solution with a different optical refractive index than the solution without bound complex. The optical refractive index change is measured by the SWS biosensor.

We claim:

1. A method of analyzing or identifying one or more molecules comprising:
    (a) contacting a sample comprising the one or more molecules with a colorimetric resonant reflectance optical sensor such that one or more of the one or more molecules become immobilized to the colorimetric resonant reflectance optical sensor;
    (b) detecting the one or more molecules immobilized to the colorimetric resonant reflectance optical sensor;
    (c) eluting the immobilized one or more molecules from the colorimetric resonant reflectance optical sensor; and
    (d) subjecting the one or more molecules to mass spectrometry analysis, wherein one or more molecules are analyzed or identified.

2. The method of claim 1, wherein the one or more molecules immobilized to the colorimetric resonant reflectance optical sensor are quantified.

3. The method of claim 1, wherein the one or more molecules immobilized to the colorimetric resonant reflectance optical sensor are detected by determining a first peak wavelength of the colorimetric resonant reflectance optical sensor prior to contacting the sample with the colorimetric resonant reflectance optical sensor; determining a second peak wavelength after contacting the sample with the colorimetric resonant reflectance optical sensor and comparing the first and second peak wavelengths, wherein a shift in peak wavelength indicates that the one or more molecules of the sample have immobilized to the colorimetric resonant reflectance optical sensor.

4. The method of claim 1, wherein analyzing or identifying the one or more molecules immobilized to the colorimetric resonant reflectance optical sensor comprises the use of a tag.

5. The method of claim 4, wherein the tag is biotin, succinimidyl-6-[a-methyl-a-(2-pyridyl-dithio) toluamido] hexanoate (SMPT), dimethylpimelimidate (DMP), or histidine.

6. The method of claim 1, wherein the one or more molecules are immobilized to the colorimetric resonant reflectance optical sensor by one or more specific binding substances on the surface of the colorimetric resonant reflectance optical sensor.

7. The method claim 6, wherein the one or more specific binding substances comprise a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, biological sample or a combination thereof.

8. The method of claim 1, wherein the colorimetric resonant reflectance optical sensor is coupled to a microfluidic channel.

* * * * *